US 6,626,879 B1

(12) United States Patent
Ashton et al.

(10) Patent No.: US 6,626,879 B1
(45) Date of Patent: Sep. 30, 2003

(54) DISPOSABLE ABSORBENT ARTICLE HAVING ARTICLE RETENTION ZONES

(75) Inventors: Gregory Ashton, Cincinnati, OH (US); Frederick Michael Langdon, Cincinnati, OH (US); Vijay Rajagopalan, Kobe (IN); David Joseph Kenneth Goulait, West Chester, OH (US); Julie Lyn Moore, Cincinnati, OH (US); Juan Carlos Velez, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/312,997

(22) Filed: May 17, 1999

(51) Int. Cl.[7] ................................. A61F 13/20
(52) U.S. Cl. .............................. 604/385.03; 604/385.01
(58) Field of Search ................................. 604/358, 373, 604/391, 367, 378, 365, 386, 387, 385.03, 385.01

(56) References Cited

U.S. PATENT DOCUMENTS

| | | | | |
|---|---|---|---|---|
| 5,246,433 A | * | 9/1993 | Hasse et al. ................. 604/358 |
| 5,769,838 A | * | 6/1998 | Buell et al. .................. 604/358 |
| 5,782,819 A | * | 7/1998 | Tanzer et al. ..................... 2/337 |
| 5,843,068 A | * | 12/1998 | Allen et al. ............ 604/385.22 |
| 5,858,013 A | * | 1/1999 | Kling .............................. 2/337 |
| 5,860,965 A | | 1/1999 | Lavash et al. |
| 6,075,179 A | | 6/2000 | McCormack et al. |
| 6,120,487 A | * | 9/2000 | Ashton ....................... 604/358 |
| 6,135,988 A | | 10/2000 | Turner et al. |
| 6,176,952 B1 | * | 1/2001 | Maugans et al. .......... 156/290 |

FOREIGN PATENT DOCUMENTS

| | | |
|---|---|---|
| CA | 2248628 | 4/1999 |
| EP | 0 641 552 A1 | * 3/1995 |
| WO | WO 00/37008 | 6/2000 |

* cited by examiner

Primary Examiner—Weilun Lo
Assistant Examiner—Linh Truong
(74) Attorney, Agent, or Firm—Michael P. Hayden; Ken K. Patel

(57) ABSTRACT

A disposable absorbent garment having an elastic waist panel that includes one or more localized retention zones for retention the garment in its initial, as-applied position on the body of a wearer. The retention zones includes materials that have a higher coefficient of static friction than does the major surface area that constitutes the inner, body-facing surface of the garment. The garment can also include localized areas having a lower coefficient of static friction than that of the major inner surface area of the garment to facilitate placement of the garment in a desired wearing position. Such lower coefficient of static friction areas can include the areas adjacent the leg openings and the area of the waistband that overlies the stomach of the wearer. Additionally, the garment can also include within the waistband, as well as within the side, hip engaging panels of the garment, areas wherein the coefficient of static friction varies from high to low to provide improved retention and comfort over a wide range of wearing conditions and a wide range of movements of the wearer.

42 Claims, 19 Drawing Sheets

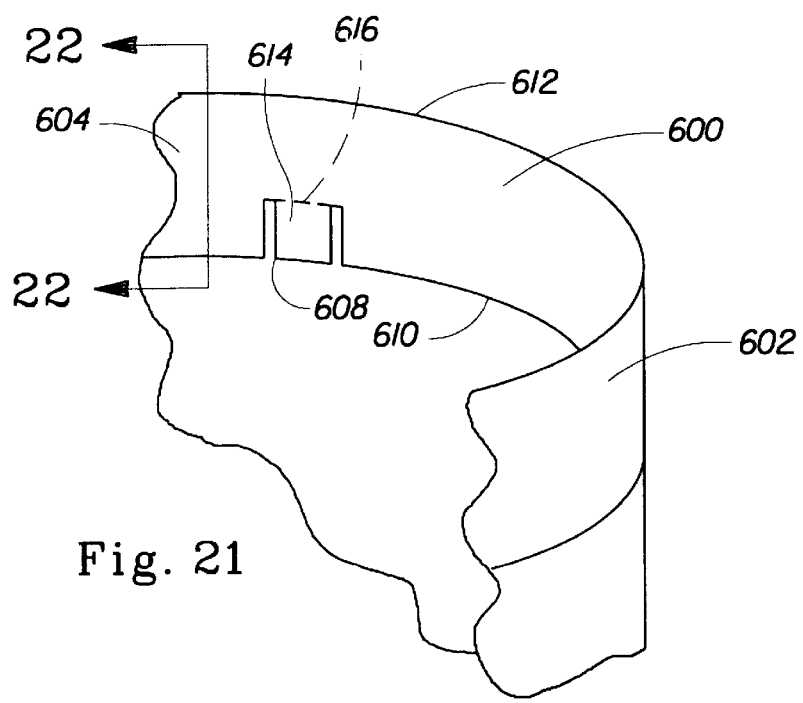
Fig. 21
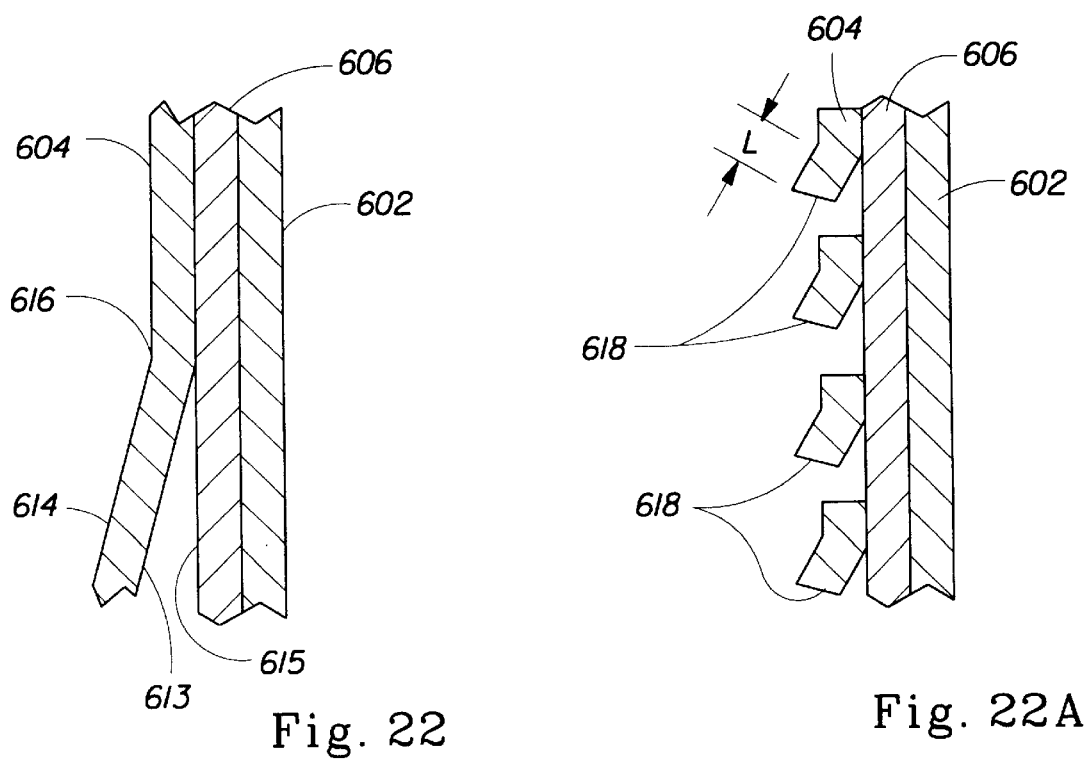
Fig. 22
Fig. 22A

DISPOSABLE ABSORBENT ARTICLE HAVING ARTICLE RETENTION ZONES

FIELD

The present invention relates to disposable absorbent articles, such as incontinence garments for infants, children, and adults, including disposable underwear, disposable diapers, disposable pull-on diapers, disposable training pants, and disposable panties for menstrual use. More specifically, the present invention relates to disposable absorbent articles that include retention zones for preventing slippage of the absorbent article relative to the body of a wearer during the time the article is worn.

BACKGROUND

Infants and others who are incontinent wear disposable absorbent articles such as diapers or other absorbent undergarments to receive and contain urine and other bodily exudates. Absorbent articles in the form of garments that are pre-assembled for slip-on application on the body of a wearer (e.g., training pants or pull-on diapers) have recently become popular. In order both to contain bodily exudates and also to fit a wide variety of body shapes and sizes, such garments must fit snugly about the waist and legs of the wearer without drooping, sagging, or sliding down from their position on the lower torso, and without causing unnecessary pressure on the skin by reason of the product being too tight for the wearer's comfort.

Many types of pull-on garments use conventional elastic elements secured in an elastically contractible condition in the waist and leg openings. For example, pull-on absorbent garments known as "balloon type" pants include elasticized bands in specific zones of the product that are in contracted form, while the remaining material tends to blouse. Examples of such pull-on garments are disclosed in U.S. Pat. No. 5,171,239 published on Dec. 15, 1992, U.S. Pat. No. 4,610,681 published on Sep. 9, 1986. Those garments will fit a range of waist and leg sizes because the elastic portions will expand to accommodate various size wearers. Nonetheless, the range of sizes is limited because the elastic elements, which enable this variation in size, have a limited degree of stretch. The narrow elastic bands used in the waist opening and the leg openings also tend to concentrate the fit forces in a narrow zone of the wearer's body leading to increased incidence of skin marking of the wearer.

Other types of pull-on, absorbent garments that employ waist elastics and side elastics are disclosed in U.S. Pat. No. 4,940,464, published on Jul. 10, 1990, U.S. Pat. No. 5,246,433, published on Sep. 21, 1993, U.S. Pat. No. 5,591,155, published on Jan. 7, 1997, EP publication 0 526 868 A1 published on Feb. 10, 1993, U.S. Pat. No. 5,545,158 published on Aug. 13, 1996; and EP publication 0 547 497 A2, published on Jun. 23, 1993.

Disposable, absorbent garments of the type identified above are generally held in position on the body of the wearer by an elasticized structure that is positioned in the waist area of the garment. The elasticized structure is preferably under tension to generate a hoop stress within the waist structure and cause it to engage with and to press against the waist area of the wearer. And to minimize downward slippage or drooping of such garments while they are worn, the hoop stress within the elasticized waist structure must be large enough to cause an inward force of sufficient magnitude to press against the skin at the wearer's waist. The inward force should be great enough to provide a normal force against the wearer's body to result in sufficient friction between the wearer's skin and the inner surface of the elastic waist structure to overcome those forces that act to tend to pull the garment down from the wearer's waist, away from garment's initial position when it was first applied to the wearer. In that regard, the downward forces acting on the garment to pull it down are caused, in part, by movements by the wearer, and they are also caused, in part, by an increase in the weight of the absorbent, exudate-receiving core, which results from the absorption and containment by the absorbent core of waste products in the form of urine and fecal material.

But in providing sufficient hoop stress within the elasticized waist structure to attempt to cause the garment to be retained in its initial position on the wearer's body, the inward force acting against the wearer's waist causes pressure and tightness to be exerted on the body of the wearer, which can cause wearer discomfort, and can also cause undesirable pressure marks, sometimes referred to as "red marks," on the wearer's skin about the wearer's waist. Such red marks are indicative of the relatively high inward forces that are imposed on the wearers waist, and they are undesirable both because they cause discomfort to the wearer and also because they cause anxiety to mothers of small children who wear such garments. The present invention is directed to minimizing such discomfort and the attendant red marking of the wearer's skin by providing increased surface static friction between the garment and the wearer's skin, which enables the hoop stress, and the resulting inward forces acting against the wearer's body, to be reduced. Additionally, because it enables lower pressure forces against the skin of a wearer, the present invention also serves to reduce skin abrasion resulting from relative movement of portions of such garments and the wearer's skin.

The broad notion of increasing the coefficient of friction of an interior surface of a disposable diaper is disclosed in U.S. Pat. No. No. 5,782,819, entitled "Article with Stay-In-Place Feature," which issued on Jul. 21, 1998, to Tanzer et al., and in International Patent Publication No. WO 95/22306, entitled "Absorbent Pant Diaper," which was published on Aug. 24, 1995, in the name of Kling et al. as inventors. However, the latter does not disclose particular values of coefficient of friction, and it teaches placement of a friction agent at the hip portions of the diaper, but not over the side seams and not in the back portions of the diaper. And the former discloses an arrangement wherein the dynamic coefficient of friction has a first value when movement occurs in a first direction, and a second value when movement occurs in the opposite direction.

It is an object of the present invention to provide a disposable absorbent article that includes a relatively high coefficient of static friction at selected portions of the skin-facing surfaces of the article, to retain the article in its desired wearing position during movements by the wearer.

It is another object of the present invention to provide a disposable absorbent article that includes a relatively low coefficient of static friction on selected portions of the structure to facilitate application of the article to the body of a wearer and also to facilitate removal therefrom.

SUMMARY

Briefly stated, in accordance with one aspect of the present invention, a disposable garment is provided that has a chassis that includes a topsheet, a backsheet joined with the topsheet, and an absorbent core interposed between the topsheet and the backsheet. The chassis has a front region, a back region, a crotch region between the front region and the back region, and side edges and end edges. A pair of side seams join portions of the side edges of the chassis at the front region to other portions of the respective side edges of the chassis at the back region to form a garment having pair of laterally spaced leg openings and a waist opening spaced from each of the leg openings. At least one retention zone is positioned interiorly of the garment at the waist opening and overlying a side seam. The retention zone has a coefficient of static friction that is at least about 200% greater than that of other body-contacting portions of the waistband, to assist in retention of the garment in a desired wearing position on the body of a wearer.

In accordance with another aspect of the present invention, the disposable garment includes slip zones within the interior, body-facing surface of the garment to facilitate application and removal of the garment from the body of a wearer. The slip zones have a relatively low coefficient of static friction, of the order of less than about 0.20. The slip zones can be positioned on the inner surface of the waistband at points between the retention zones, or on the portion of the waistband that overlies the wearer's stomach when the garment is worn, or they can be positioned around the interior surface adjacent the leg openings to reduce drag during application and removal of the garment. Moreover, zones of intermediate coefficient of static friction, within the range of from about 0.20 to about 1.5, can be positioned between the retention zones and the slip zones.

In accordance with a further aspect of the present invention, the inner surface of the waistband can include one or more pivotable flaps. In one position of the flaps an area of relatively high coefficient of static friction is covered and in a second, pivoted position of the flaps the high coefficient of static friction area is exposed to the skin of the wearer. The flap material that pivots about a pivot axis that is substantially parallel with the circumference of the waistband to expose an area having a coefficient of static friction of the order of from about 0.20 to about 1.5.

BRIEF DESCRIPTION OF THE DRAWINGS

FIG. 21 is a fragmentary perspective view of the interior waistband area of an absorbent, pull-on diaper that incorporates pivotable inner flaps.

FIG. 22 is a cross-sectional view taken along the line 22—22 of FIG. 21 showing a unitary pivotable flap.

FIG. 22a is a view similar to that of FIG. 22, but showing a plurality of shorter, parallel flaps

DETAILED DESCRIPTION

As used herein, "pull-on garment" refers to articles of wear which have a defined waist opening and a pair of leg openings and which are pulled onto the body of the wearer by inserting the legs into the leg openings and pulling the article up over the waist.

As used herein, "disposable" describes garments which are not intended to be laundered or otherwise restored or reused as a garment (i.e., they are intended to be discarded after a single use and, preferably, to be recycled, composted or otherwise disposed of in an environmentally compatible manner).

As used herein, a "unitary" pull-on garment refers to pull-on garments which are formed of separate parts united together to form a coordinated entity, but the ear panels are not separate elements joined to a separate chassis in that the ear panels are formed by at least one layer which also forms the central panel or chassis of the garment (i.e., the garment does not require separately manipulative panels such as a separate chassis and separate ear panels). The pull-on garment is also preferably "absorbent" to absorb and contain the various exudates discharged from the body. A preferred embodiment of the pull-on garment of the present invention is the unitary disposable absorbent pull-on garment, pull-on diaper 20, shown in FIG. 1.

As used herein, "pull-on diaper" refers to pull-on garments generally worn by infants and other incontinent individuals to absorb and contain urine and feces. It should be understood, however, that the present invention is also applicable to other pull-on garments such as training pants, incontinent briefs, feminine hygiene garments or panties, and the like.

As used herein, "joined" or "joining" encompasses configurations whereby an element is directly secured to the other element by affixing the element directly to another element, and configurations whereby the element is indirectly secured to the other element by affixing the element to intermediate member(s) which in turn are affixed to the other element.

As used herein, "longitudinal" refers to a line, axis, or direction in the plane of a pull-on diaper that is generally aligned with (e.g. approximately parallel with) a vertical plane which bisects a standing wearer into left and right halves when the pull-on diaper is worn.

As used herein, "transverse" and "lateral" are interchangeable and refer to a line, axis, or direction that lies within the plane of the diaper that is generally perpendicular to the longitudinal direction (which divides the wearer into front and back body halves).

Figure 1:
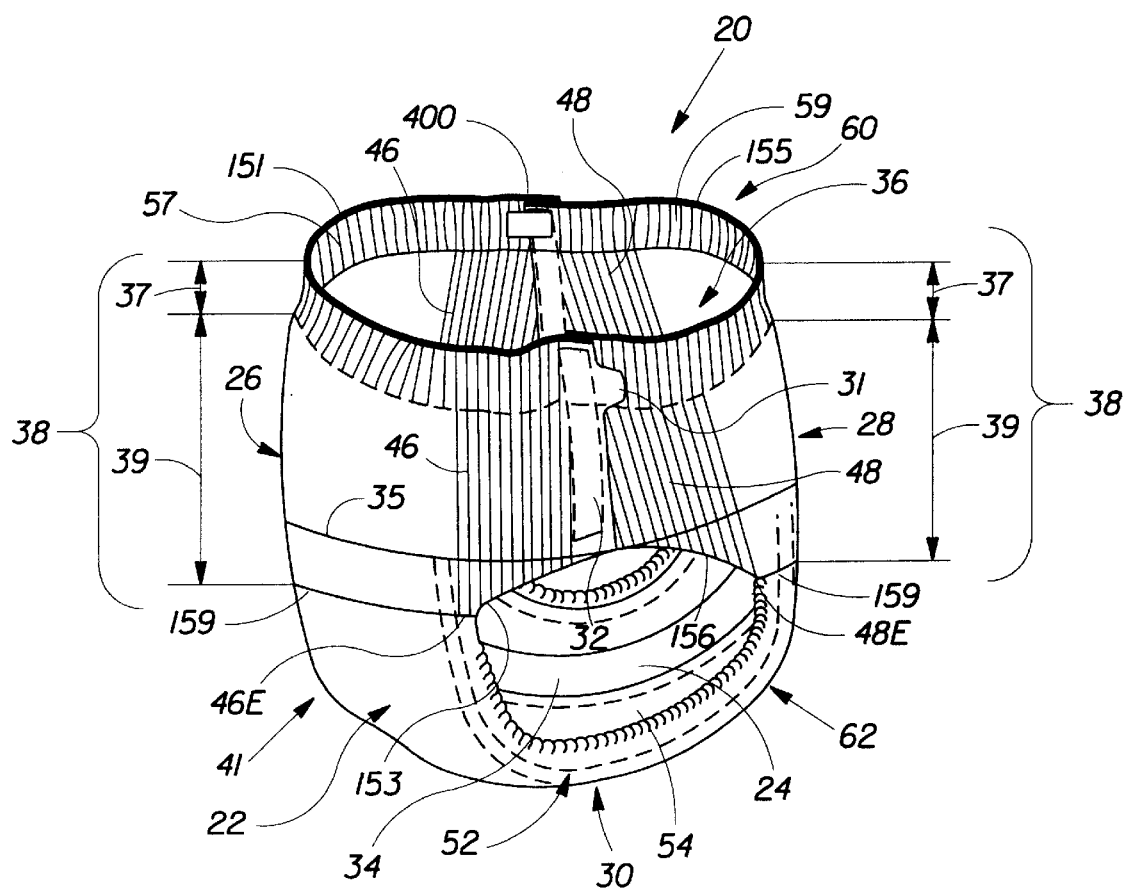
FIG. 1 is a side perspective view of a disposable, absorbent, pull-on garment in accordance with the present invention in assembled form and ready for use.
Figure 2:
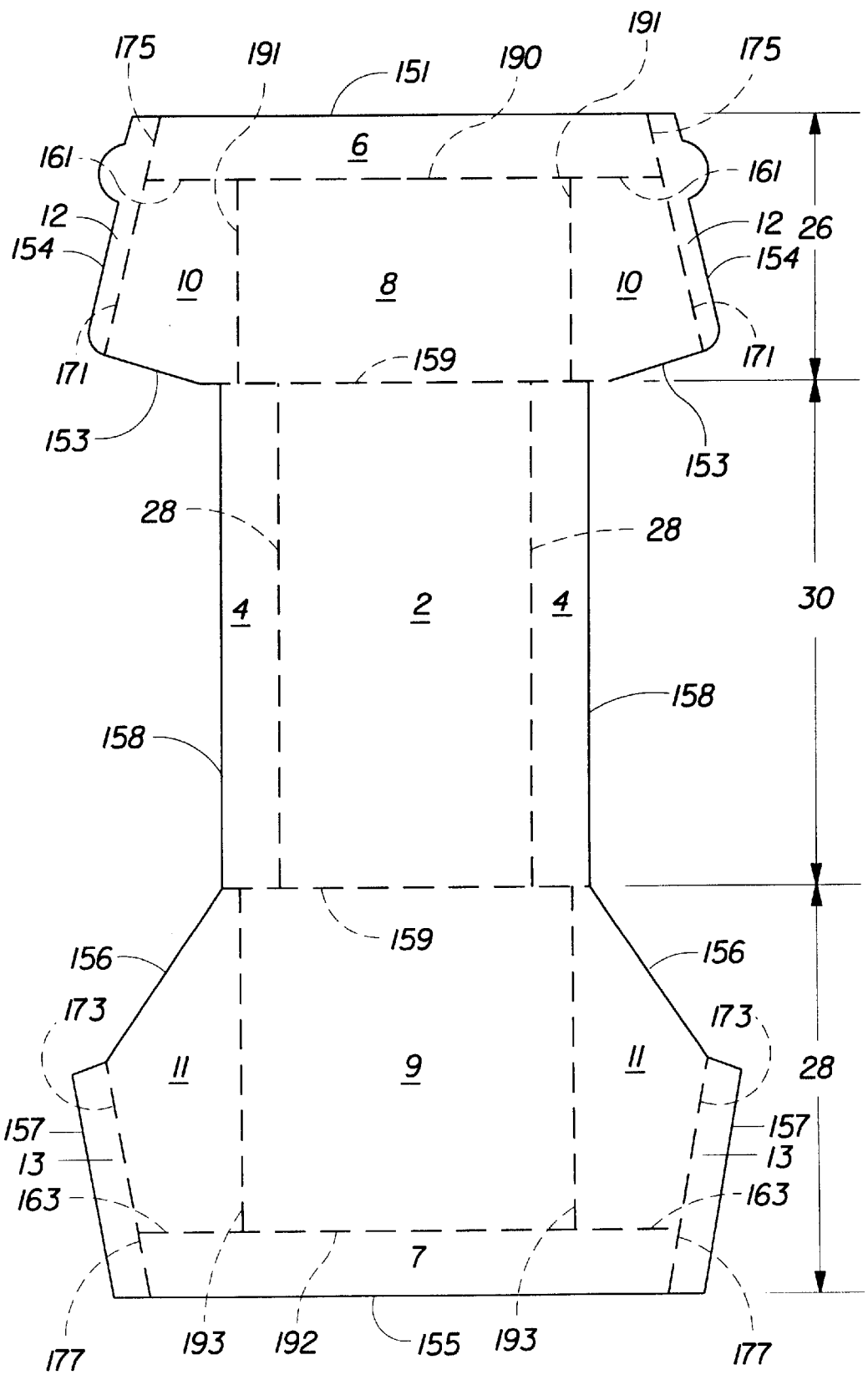
FIG. 2 is a plan view of the disposable garment of FIG. 1 in its flat, uncontracted, and unseamed condition and showing various panels and edges that define the several portions of the garment.
Figure 3:
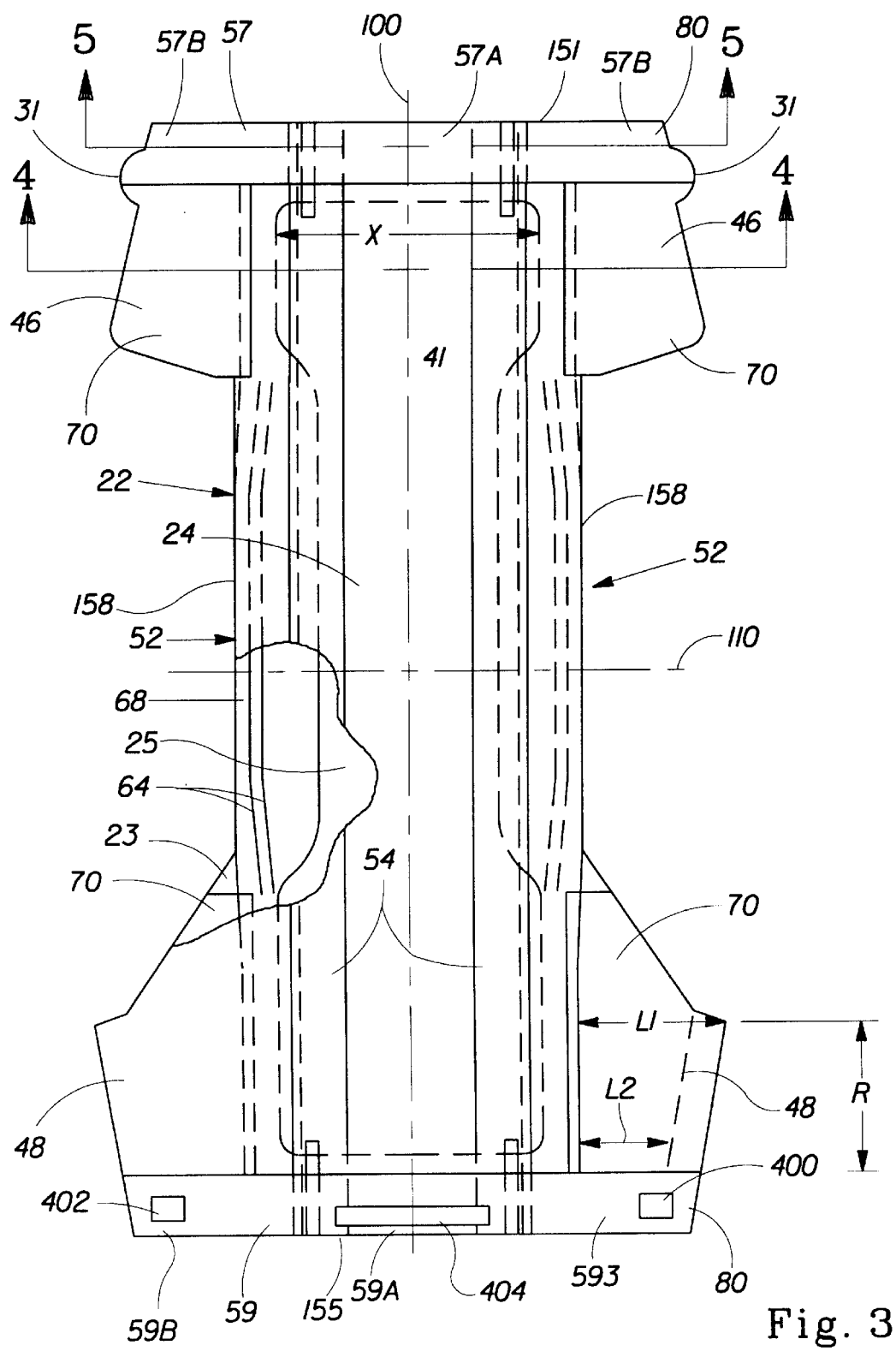
FIG. 3 is a plan view of the garment shown in FIG. 1 when it is in its flat, uncontracted, and unseamed condition and showing the relative positions of the several structural components of the garment.

Referring to FIGS. 1, 2, and 3, pull-on diaper 20 has a front region 26, a back region 28, and a crotch region 30 that is positioned between front region 26 and back region 28. Diaper 20 also has two centerlines, a longitudinal centerline 100, and a transverse centerline 110, and the component materials thereof have a body-facing surface which faces the skin of wearer in use and an outer-facing surface that faces away from the body-facing surface.

FIG. 2 is a plan view of the pull-on diaper 20 of FIG. 1 in its flat-out, uncontracted state showing the various panels that together define the diaper structure and their positions relative to each other. The term "panel" is used herein to denote an area or an element of the pull-on diaper or the belt. Although a panel is typically a distinct area or element, a panel can coincide or functionally correspond with an adjacent panel.

A shown in FIG. 2, diaper 20 has a crotch region 30 that includes a main panel 2 and a pair of elongated, generally rectangular leg flap panels 4 that are connected with main panel 2 along respective longitudinal edges 2B. A front region 26 comprising a central panel (medial panel) 8, a waistband panel 6, ear panels 10, and seam panels 12; and a back region 28 comprising a central panel (medial panel) 9, a waistband panel 7, ear panels 11, and seam panels 13. The crotch region 30 is the portion of the pull-on diaper 20 from which the continuous belt (the other panels) emanates. The absorbent core is generally positioned within the main panel 2 since exudates are typically discharged in this region although the absorbent core will typically extend into the medial panels 8 and 9 of the belt. A leg flap panel 4 extends generally laterally outwardly from and along each side edge 2B of the main panel 2. Each leg flap panel 4 generally forms at least a portion of the elastic leg feature.

The continuous belt zone (the front region 26 and the back region 28) extends generally longitudinally outwardly from and along each lateral edge 159 of the crotch region 30 (the main panel 2 and the leg flap panel 4). In the front region 26, the medial panel 8 (i.e., central panel) extends generally longitudinally outwardly from and along the lateral edge 159 of the crotch region 30. The medial panel 8 has a waist edge 190 and side edges 191.

The ear panels 10 each extend generally laterally outwardly from and along the side edge 191 of the medial panel 8 (i.e., central panel). The ear panel 10 has a waist edge 161 and a side edge 171. The waistband panel 6 extends generally longitudinally outwardly from and along the waist edge 190 of the medial pajel 8 (i.e., central panel) and the waist edge 161 of the ear panel 10. The waistband panel 6 has side edges 175.

The seam panels 12 each extend generally laterally outwardly from and along the side edge 171 of the ear panel 10 and the side edge 175 of the waistband panel 6. In the back region 28, the medial panel 9 (i.e., central panel) extends generally longitudinally outwardly from and along the other lateral edge 159 of the crotch region 30.

The medial panel 9 has a waist edge 192 and side edges 193. The ear panels 11 each extend generally laterally outwardly from and along the side edge 193 of the medial panel 9 (i.e., central panel). The ear panel 11 has a waist edge 163 and a side edge 173.

The waistband panel 7 extends generally longitudinally outwardly from and along the waist edge 192 of the medial panel 9 (i.e., central panel) and the waist edge 163 of the ear panel 11. The waistband panel 7 has side edges 177. The seam panels 13 each extend generally laterally outwardly from and along the side edge 173 of the ear panel 11 and the side edge 177 of the waistband panel 7. The front region 26, in addition to its panels, also has a waist edge 151, leg edges 153, and side edges 154. The back region 28, in addition to its panels, also has a waist edge 155, leg edges 156, and side edges 157. The crotch region 30 has leg edges 158.

Diaper 20 includes a chassis 41, a waist elastomeric material (not shown in FIGS. 1, 2, and 3), a side elastomeric material (not shown in FIGS. 1, 2, and 3), and seams 32. The pull-on diaper 20 can have tear open tabs 31, whose positioning is associated with the seams 32 and elasticized leg cuffs 52 including inner barrier cuffs 54. The side elastomeric material renders at least a part of the ear panel 10 and 11 extensible, thereby forming extensible ear 46 and 48. The waist elastomeric material renders at least a part of the waistband panel 6 and 7 extensible, thereby forming continuous extensible waistband 57 and 59. The side elastomeric material and the waist elastomeric material are separate elements to each other and disposed so as not to overlap to each other in the longitudinal direction of the pull-on diaper 20. This allows more independent behavior of the waist and side elastomeric materials to allow for adjustments in dimension extension, pressure, etc. The extensible ear 46 and 48 and continuous extensible waistband 57 and 59 are extensible at least in the lateral direction. The seam 32 joins the seam panel 12 in the front region 26 to the seam panel 13 in the back region 28, whereby the ear panel 10 is joined to the ear panel 11 and whereby one waist opening 36 and two leg openings 34 are formed. In the configuration where the ear panel 10 is joined to the ear panel 11, the continuous extensible waistband 57 and 59 forms a continuous extensible waist feature 60 about the waist opening 36. Further, a continuous belt zone 38 extends in the front region 26 and the back region 28.

Referring to FIG. 3, the chassis 41 comprises an absorbent core 25 and a plurality of layers disposed in association with the absorbent core 25, such as a topsheet 24 and a backsheet 22 associated with the topsheet 24. The absorbent core 25 is disposed between the topsheet 24 and the backsheet 22. The chassis 41 further can include one or more additional layers disposed associated with the absorbent core 25. The topsheet 24 has the body-facing surface that is positioned adjacent to the wearer's body during use. The backsheet 22 has the outer-facing surface that is positioned away from the wearer's body. Preferably, the backsheet 22 comprises an inner barrier film 68 and a nonwoven outer cover 23. Since the chassis 41 defines the front region 26, the back region 28, and crotch region 30, the chassis 41 also has corresponding regions and panels as previously defined. (For simplicity, these regions and panels are denoted in the drawings by the same reference numerals as the corresponding pull-on diaper regions and panels as shown in FIG. 2.)

The topsheet 24 and the inner barrier film 68 of the backsheet 22 have length and width dimensions generally larger than those of the absorbent core 25. The topsheet 24 and the inner barrier film 68 extend beyond the side edges and end edges of the absorbent core 25 to thereby form the periphery of the chassis 41. The topsheet 24 longitudinally extends between the waist edge 151 and 155 of the pull-on diaper 20. The topsheet 24 has waist end portions 24A and side portions 24B. The waist end portions 24A (i.e., end extended portion 24A) of the topsheet 24 extend into a portion of the waistband panel 6 and 7 of the pull-on diaper 20. The inner barrier film 68 has waist end portions 68A and side portions 68B. The inner barrier film 68 is a little shorter in the longitudinal direction than the topsheet 24 and a little wider in the lateral direction than the topsheet 24. The inner barrier film 68 has a nonuniform lateral width so as to form a first portion 94 in at least a portion of the crotch region 30 and a second portion 96 in at least a portion of the front or back region 26 and 28. The lateral width of the inner barrier film 68 gradually decreases towards the waist end portions 68A such that the second portion 96 has a lateral width dimension less than the lateral width dimension of the first portion 94. The inner barrier film 68 does not preferably extend into the ear panel 10 and 11 so as to increase the effective lateral extended length of the ear panel 10 and 11 and reduce bulkiness of the ear panel 10 and 11. The inner barrier film 68 also does not extend into the waistband panel 6 and 7 so as to reduce bulkiness of the waistband panel 6 and 7. In addition, since the inner barrier film 68 does not extend into both the ear panels 10 and 11 and the waistband panel 6 and 7, the inner barrier film 68 does not inhibit breathability in those areas. While the topsheet 24, the inner barrier film 68, and the absorbent core 25 can be assembled in a variety of well known configurations, exemplary chassis configurations are described generally in U.S. Pat. No. No. 3,860,003, entitled "Contractible Side Portions for Disposable Diaper," which issued to Kenneth B. Buell on Jan. 14, 1975; and in U.S. Pat. No. 5,151,092, entitled "Absorbent Article With Dynamic Elastic Waist Feature Having A Predisposed Resilient Flexural Hinge," which issued to Kenneth B. Buell et al., on Sep. 29, 1992.

Preferably, the nonwoven outer cover 23 covers almost all of the area of the outermost portion of the pull-on diaper 20. The nonwoven outer cover 23 can have generally the same shape as the pull-on diaper 20. The nonwoven outer cover 23 has waist end portions 23A and side portions 23B. The nonwoven outer cover 23 also has a side extended portion 23C in the front region 26 and a side extended portion 23D in the back region 28. The waist end portion 23A (i.e., end extended portion 23A) of the nonwoven outer cover 23 extends into the waistband panel 6 and 7, and the side extended portion 23C and 23D of the nonwoven outer cover 23 extends into the ear panel 10 and 11. Alternatively, the nonwoven outer cover 23 of the backsheet 22 can have generally same shape as the inner barrier film 68 such that the nonwoven outer cover 23 covers only the area of the inner barrier film 68. Alternatively, the nonwoven outer cover 23 can be eliminated, and the inner barrier film 68 can have generally the same shape as the pull-on diaper 20 and extend into both ear panel 10 and 11 and waistband panel 6 and 7.

The absorbent core 25 can be any absorbent member that is generally compressible, conformable, non-irritating to the wearer's skin, and capable of absorbing and retention liquids such as urine and other certain body exudates. The absorbent core 25 can be manufactured in a wide variety of sizes and shapes (e.g., rectangular, hourglass, "T"-shaped, asymmetric, etc.) and from a wide variety of liquid absorbent materials commonly used in disposable diapers and other absorbent articles such as comminuted wood pulp which is generally referred to as airfelt. Examples of other suitable absorbent materials include creped cellulose wadding; meltblown polymers including coform; chemically stiffened, modified or cross-linked cellulosic fibers; tissue including tissue wraps and tissue laminates; absorbent foams; absorbent sponges; superabsorbent polymers; absorbent gelling materials; or any equivalent material or combinations of materials.

The configuration and construction of the absorbent core 25 can vary (e.g., the absorbent core 25 can have varying caliper zones, a hydrophilic gradient, a superabsorbent gradient, or lower average density and lower average basis weight acquisition zones; or can comprise one or more layers or structures). Further, the size and absorbent capacity of the absorbent core 25 can also be varied to accommodate wearers ranging from infants through adults. However, the total absorbent capacity of the absorbent core 25 should be compatible with the design loading and the intended use of the diaper 20.

The absorbent core 25 in a preferred embodiment has an asymmetric, modified hourglass-shape having ears in the front and back waist regions 26 and 28. Other exemplary absorbent structures for use as the absorbent core 25 that have achieved wide acceptance and commercial success are described in U.S. Pat. No. No. 4,610,678, entitled "High-Density Absorbent Structures," which issued to Weisman et al. on Sep. 9, 1986; in U.S. Pat. No. No. 4,673,402, entitled "Absorbent Articles With Dual-Layered Cores," which issued to Weisman et al. on Jun. 16, 1987; in U.S. Pat. No. 4,888,231, entitled "Absorbent Core Having A Dusting Layer," which issued to Angstadt on Dec. 19, 1989; and in U.S. Pat. No. 4,834,735, entitled "High Density Absorbent Members Having Lower Density and Lower Basis Weight Acquisition Zones," which issued to Alemany et al. on Can 30, 1989.

Figure 4:
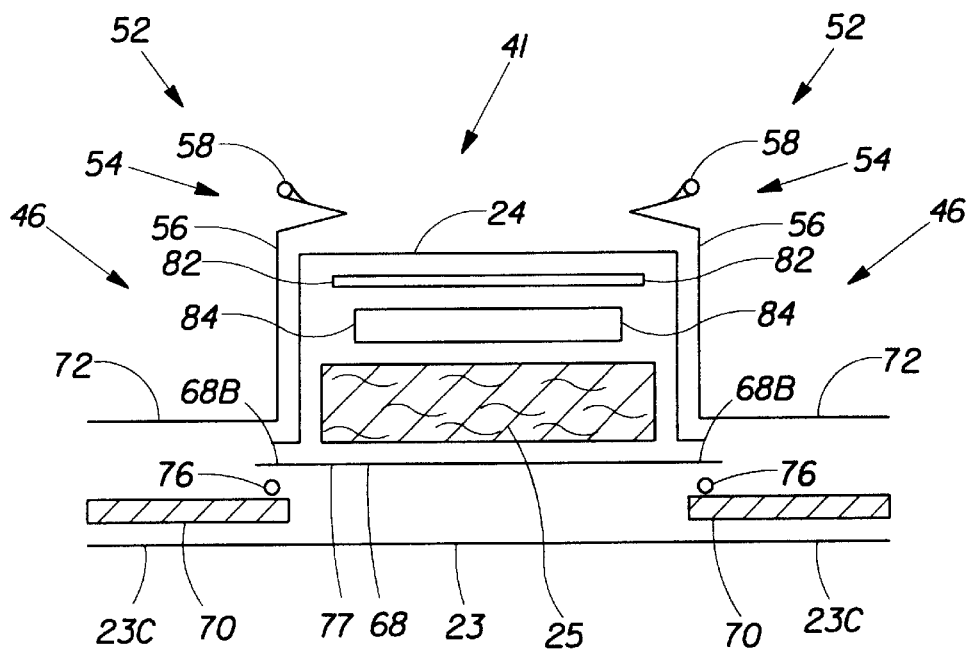
FIG. 4 is a cross-sectional view taken along the line 4—4 of FIG. 3.

The chassis 41, as shown in FIG. 4, can further include an acquisition/distribution core 84 of chemically stiffened fibers positioned over the absorbent core 25, thereby forming a dual core system. Preferred dual core systems are disclosed in U.S. Pat. No. 5,234,423, entitled "Absorbent Article With Elastic Waist Feature and Enhanced Absorbency," which issued to Alemany et al., on Aug. 10, 1993; and in U.S. Pat. No. 5,147,345, entitled "High Efficiency Absorbent Articles For Incontinence Management," which issued to Young et al. on Sep. 15, 1992. In a preferred embodiment, the acquisition/distribution core 84 comprise chemically treated stiffened cellulosic fiber material, available from Weyerhaeuser Co. (U.S.A.) under the trade designation of CMC.

Alternatively, the chassis 41 can further include an acquisition/distribution layer 82 between the topsheet 24 and the acquisition/distribution core 84 as shown in FIG. 4. The acquisition/distribution layer 82 is provided to help reduce the tendency for surface wetness of the topsheet 24. The acquisition/distribution layer 82 preferably comprises carded, resin bonded hiloft nonwoven materials such as, for example, available as Code No. FT-6860 from Polymer Group, Inc., North America (Landisiville, N.J., U.S.A.), which is made of polyethylene terephthalate fibers of 6 dtex, and has a basis weight of about 43 g/m$^2$.

The topsheet 24 is preferably compliant, soft feeling, and non-irritating to the wearer's skin. Further, the topsheet 24 is liquid pervious permitting liquids (e.g., urine) to readily penetrate through its thickness. A suitable topsheet 24 can be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can be comprised of natural fibers (e.g., wood or cotton fibers), synthetic fibers (e.g., polymeric fibers such as polyester, polypropylene, or polyethylene fibers) or from a combination of natural and synthetic fibers.

The topsheet 24 is preferably made from a hydrophobic material to isolate the wearers skin from liquids which have passed through the topsheet 24 and are contained in the absorbent core 25 (i.e., to prevent rewet). If the topsheet 24 is made of a hydrophobic material, it is preferable that at least the upper surface of the topsheet 24 is treated to be hydrophilic so that liquids will transfer through the topsheet more rapidly. This diminishes the likelihood that body exudates will flow off the topsheet 24 rather than flowing through the topsheet 24 and to the absorbent core 25. The topsheet 24 can be rendered hydrophilic by treating it with a surfactant. Suitable methods for treating the topsheet 24 with a surfactant include spraying the topsheet 24 material with the surfactant and immersing the material into the surfactant. A more detailed discussion of such a treatment and hydrophilicity is contained in U.S. Pat. No. 4,988,344, entitled "Absorbent Articles with Multiple Layer Absorbent Layers," which issued to Reising, et al on Jan. 29, 1991; and in U.S. Pat. No. 4,988,345, entitled "Absorbent Articles with Rapid Acquiring Absorbent Cores," which issued to Reising on Jan. 29, 1991. The topsheet 24 can be compatible with ventilation design/process preferably along the waistband panel 6 and 7 and other portions on the pull-on diaper 20.

In preferred embodiments, the topsheet 24 is a nonwoven web that can provide reduced tendency for surface wetness; and consequently facilitate maintaining urine absorbed by the absorbent core 25 away from the user's skin, after wetting. One of the preferred topsheet materials is a thermobonded, carded web that is available as Code No. P-8 from Fiberweb North America, Inc. (Simpsonville, S.C., U.S.A.). Another preferred topsheet material is available as Code No. S-2355 from Havix Co., Japan. This material is a bi-layer composite material, and made of two kinds of synthetic surfactant treated bicomponent fibers by using carding and air-through technologies. Yet another preferred topsheet material is a thermobonded, carded web that is available as Code No. Profleece Style 040018007 from Amoco Fabrics, Inc. (Gronau, Germany).

Another preferred topsheet 24 comprises an apertured formed film. Apertured formed films are preferred for the topsheet 24 because they are pervious to body exudates and yet non-absorbent and have a reduced tendency to allow liquids to pass back through and rewet the wearer's skin. Thus, the surface of the formed film that is in contact with the body remains dry, thereby reducing body soiling, and creating a more comfortable feel for the wearer. Suitable formed films are described in U.S. Pat. No. 3,929,135, entitled "Absorptive Structures Having Tapered Capillaries," which issued to Thompson on Dec. 30, 1975; in U.S. Pat. No. 4,324,246, entitled "Disposable Absorbent Article Having A Stain Resistant Topsheet," which issued to Mullane, et al. on Apr. 13, 1982; in U.S. Pat. No. 4,342,314, entitled "Resilient Plastic Web Exhibiting Fiber-Like Properties," which issued to Radel et al. on Aug. 3, 1982; in U.S. Pat. No. 4,463,045, entitled "Macroscopically Expanded Three-Dimensional Plastic Web Exhibiting Non-Glossy Visible Surface and Cloth-Like Tactile Impression," which issued to Ahr et al. on Jul. 31, 1984; and in U.S. Pat. No. 5,006,394, entitled "Multilayer Polymeric Film," which issued to Baird on Apr. 9, 1991.

The backsheet 22 preferably comprises an inner barrier film 68 and a nonwoven outer cover 23. The inner barrier film 68 is preferably impervious to liquids (e.g., urine) and is preferably manufactured from a thin plastic film. The inner barrier film 68 has a body-facing surface 79 and an outer-facing surface 77. More preferably the plastic film permits vapors to escape from the diaper 20. In a preferred embodiment, a microporous polyethylene film is used for the inner barrier film 68. A suitable microporous polyethylene film is manufactured by Mitsui Toatsu Chemicals, Inc., Nagoya, Japan and marketed in the trade as Espoir No. The backsheet 22 is preferably compatible with ventilation and side seaming design/process. A disposable tape can be further joined to the outer surface of the backsheet.

A suitable plastic film material for the inner barrier film 68 is a thermoplastic film having a thickness of from about 0.012 mm (0.5 mil) to about 0.051 mm (2.0 mils), preferably comprising polyethylene or polypropylene. Preferably, the plastic film has a basis weight of from about 5 g/m$^2$ to about 35 g/m$^2$. However, it should be noted that other flexible, liquid impervious materials can be used. Herein "flexible" refers to materials which are compliant and which will readily conform to the general shape and contours of the wearer's body. The plastic film can have moisture vapor transmission rate of between 3,000 and 4,000 g/m$^2$/24 hr, which is measured by a method set forth below.

The nonwoven outer cover 23 is joined with the outer-facing surface of the inner barrier film 68 to form a laminate (i.e., the backsheet 22). The nonwoven outer cover 23 is positioned at the outermost portion of the pull-on diaper 20 and covers at least a portion of the outermost portion of the diaper 20. The nonwoven outer cover 23 can be joined to the inner barrier film 68 by any suitable attachment means known in the art. For example, the nonwoven outer cover 23 can be secured to the inner barrier film 68 by a uniform continuous layer of adhesive, a patterned layer of adhesive, or an array of separate lines, spirals, or spots of adhesive. Suitable adhesives include a hotmelt adhesive obtainable from Nitta Findley Co., Ltd., Osaka, Japan as H-2128, and a hotmelt adhesive obtainable from H. B. Fuller Japan Co., Ltd., Osaka, Japan as JM-6064.

In a preferred embodiment, the nonwoven outer cover 23 is a carded nonwoven web, for example, obtainable from Havix Co., LTD., Gifu, Japan as E-2341. The nonwoven outer cover 23 is made of bi-component fibers of a polyethylene (PE) and a polyethylene terephthalate (PET). The ratio of PE/PET is about 40/60. The PE/PET bi-component fiber has the dimension of 2 decitex×51 mm. Another preferred carded nonwoven web is obtainable from Chisso Corp., Osaka, Japan. The nonwoven outer cover 23 is also made of bi-component fibers of a polyethylene (PE) and a polyethylene terephthalate (PET). The ratio of PE/PET is about 30/70.

In another preferred embodiment, the nonwoven web is a spunbonded nonwoven web, for example, obtainable from Mitsui Petrochemical Industries, Ltd., Tokyo, Japan. The nonwoven web is made of bi-component fibers consisting of a polyethylene (PE) sheath and a polypropylene (PP) core. The ratio of PE/PP is about 80/20. The PE/PP bi-component fiber has the thickness of approximately 2.3 decitex.

The backsheet 22 is preferably positioned adjacent the outer-facing surface of the absorbent core 25 and is preferably joined thereto by any suitable attachment means known in the art. For example, the backsheet 22 can be secured to the absorbent core 25 by a uniform continuous layer of adhesive, a patterned layer of adhesive, or an array of separate lines, spirals, or spots of adhesive. Adhesives that have been found to be satisfactory are manufactured by H. B. Fuller Company of St. Paul, Minn. and marketed as HL-1258. An example of a suitable attachment means comprising an open pattern network of filaments of adhesive is disclosed in U.S. Pat. No. 4,573,986 entitled "Disposable Waste-Containment Garment", which issued to Minetola et al. on Mar. 4, 1986. Another suitable attachment means comprising several lines of adhesive filaments swirled into a spiral pattern is illustrated by the apparatus and methods shown in U.S. Pat. No. 3,911,173, which issued to Sprague, Jr. on Oct. 7, 1975; in U.S. Pat. No. 4,785,996, which issued to Ziecker, et al. on Nov. 22, 1978; and U.S. Pat. No. 4,842,666, which issued to Werenicz on Jun. 27, 1989. Alternatively, the attachment means can comprise heat bonds, pressure bonds, ultrasonic bonds, dynamic mechanical bonds, or any other suitable attachment means or combinations of these attachment means as are known in the art.

In an alternative embodiment, the absorbent core 25 is not joined to the backsheet 22, and/or the topsheet 24 in order to provide greater extensibility in the front region 26 and the back region 28.

The elasticized leg cuffs 52 provides improved containment of liquids and other body exudates. The elasticized leg cuffs 52 can comprise several different embodiments for reducing the leakage of body exudates in the leg regions. (The leg cuff can be and is sometimes also referred to as leg bands, side flaps, barrier cuffs, or elastic cuffs.) U.S. Pat. No. 3,860,003 describes a disposable diaper which provides a contractible leg opening having a side flap and one or more elastic members to provide an elasticized leg cuff (gasketing cuff). U.S. Pat. No. 4,909,803 entitled "Disposable Absorbent Article Having Elasticized Flaps" issued to Aziz et al. on Mar. 20, 1990, describes a disposable diaper having "stand-up" elasticized flaps (barrier cuffs) to improve the containment of the leg regions. U.S. Pat. No. 4,695,278 entitled "Absorbent Article Having Dual Cuffs" issued to Lawson on Sep. 22, 1987; and U.S. Pat. No. 4,795,454 entitled "Absorbent Article Having Leakage-Resistant Dual Cuffs" issued to Dragoo on Jan. 3, 1989, describe disposable diapers having dual cuffs including a gasketing cuff and a barrier cuff. U.S. Pat. No. 4,704,115 entitled "Disposable Waist Containment Garment" issued to Buell on Nov. 3, 1987, discloses a disposable diaper or incontinence garment having side-edge-leakage-guard gutters configured to contain free liquids within the garment.

Figure 5:
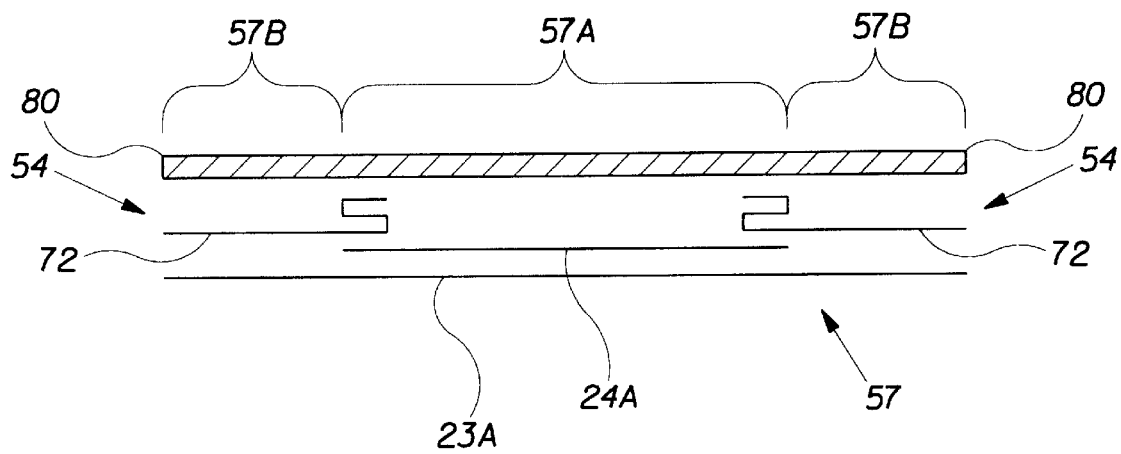
FIG. 5 is a cross-sectional view taken along the line 5—5 of FIG. 3.

While each elasticized leg cuff 52 can be configured so as to be similar to any of the leg bands, side flaps, barrier cuffs, or elastic cuffs described above, it is preferred that each elasticized leg cuff 52 comprises inner barrier cuffs 54 each comprising a barrier flap 56 and a spacing means 58 (as shown in FIG. 5) as described in the above-referenced U.S. Pat. No. 4,909,803. The inner barrier cuffs 54 can have an insert element that is highly impermeable, but preferably breathable. In a preferred embodiment, the elasticized leg cuff 52 additionally comprises an elastic gasketing cuff 62 with one or more elastic strands 64, positioned outboard of the barrier cuff 54 such as described in the above-referred U.S. Pat. Nos. 4,695,278 and 4,795,454. The elastic strands 64 are generally disposed in the leg flap panel 4 and are joined thereto by any means, such as hot melt glue under a prestrained condition. The elastic strands 64 can be prestrained, before being joined, up to between 30% and 200%, preferably between 50% and 150%. A preferred elastic strand 64 is manufactured by Fulflex International Company under the designation 9312.

The pull-on diaper 20 has the front extensible ear 46 and the back extensible ear 48. Referring to FIG. 4, the extensible ear 46 and 48 preferably comprises a side elastic member 70 having a side elastomeric material 124 (shown in FIG. 6), the side extended portion 23C of the nonwoven outer cover 23, and an extended portion 72 of the inner barrier cuff 54 (although FIG. 4 shows only the structures in the front region 26, preferably the structures in the back region 28 are the same or similar to those in the front region 26). Preferably at least one of the front and back extensible ears 46 and 48 is elastically extensible in at least the lateral direction. More preferably, both the front and tie back extensible ears 46 and 48 are elastically extensible in at least the lateral direction. In an alternative embodiment, the front and back extensible ear 46 and 48 is elastically extensible both in the lateral and longitudinal directions. Herein "extensible" refers to materials that are capable of extending in at least one direction to a certain degree without undue rupture. Herein "elasticity" and "elastically extensible" refer to extensible materials that have the ability to return to approximately their original dimensions after the force that extended the material is removed. Herein any material or element described as "extensible" can also be elastically extensible unless otherwise provided. The extensible ear 46 and/or 48 provides a more comfortable and contouring fit by initially conformably fitting the diaper to the wearer and sustaining this fit throughout the time of wear well past when the diaper has been loaded with exudates since the extensible ear 46 and/or 48 allows the sides of the diaper to expand and contract.

The extensible ear 46 and 48 preferably has breathability. The moisture vapor transmission rate of the ear panel in conjunction with the overall vapor transmission rate of the rest of the pull-on diaper is important in reducing the incidence of heat rash and other skin problems associated with high heat humidity conditions. In order to reduce humidity and heat humidity within the pull-on diaper, the extensible ear 46 and 48 preferably has a weighed average mass vapor transmission rate of at least about 2,000 g/m$^2$/24 hr, more preferably at least 4,000 g/m$^2$/24 hr. Preferably, the entire pull-on diaper has a weighed average mass vapor transmission rate of from at least 2,000 g/m$^2$/24 hr to about 8,000 g/m$^2$/24 hr.

The moisture vapor transmission rate is measured by the method set forth below. A known amount of CaCl$_2$ is put into a flanged cup. A sample is placed on the top of the cup and held securely by a retention ring and gasket. The assembly is then weighed and recorded as the initial weight. The assembly is placed in a constant temperature (40° C.) and humidity (75% RH) chamber for 5 hours. The assembly is then removed from the chamber and allowed to equilibrate for at least 30 minutes at the temperature of the room where the balance is located. The assembly is then weighed and recorded as the final weight. The mass vapor transmission rate (MVTR) is calculated and expressed in g/m$^2$/24 hr using the following formula.

$$MVTR = \frac{(Final\ weight - initial\ weight) \times 24.0}{Area\ of\ sample\ in\ meters \times 5.0\ (time\ in\ chamber)}$$

Referring to FIG. 3, the extensible ear 46 comprising the side elastic member 70 has a higher end edge 46A, a lower end edge 46B, an inner side edge 46C, and an outer side edge 46D. The back extensible ear 48 comprising the side elastic material 70 has a higher end edge 48A, a lower end edge 48B, an inner side edge 48C, and an outer side edge 48D. Although a configuration of each element, portion, part, etc. in the front region 26 can be different from that in the back region 28 (such as configuration of the front extensible ear 46 and configuration of the back extensible ear 48, or configuration of the lower end edge 46B and configuration of the lower end edge 48B), those elements, portions, parts, etc. which correspond to each other in the front region 26 and in the back region 28 can be described concurrently for ease of description.

In a preferred embodiment, the ear panel 10 and 11 is rendered extensible in the entire area of the ear panel 10 and 11 to form the extensible ear 46 and 48 by the side elastic material 70. In the embodiment shown in FIG. 3, the side elastic material 70 extends into a part of the seam panel 12 and 13 so that the front extensible ear 46 and the back extensible ear 48 are anchored each other at the seam 32, and the side elastic material 70 in the front region 26 and the side elastic material 70 in the back region 28 are anchored at the seam 32 (FIG. 4 also shows the side elastic member 70 which extends into the seam panel 12 and 13, though the seam panel 12 and 13 is not shown in FIG. 4). Alternatively, the ear panel 10 and 11 can be rendered extensible only in a portion of the area in the ear panel 10 and 11. The extensible ear 46 and 48 is the part of the ear panel 10 and 11 rendered extensible by joining the side elastic member 70 and being subjected to mechanical stretching.

In a preferred embodiment, the inner side edge 46C and 48C extends generally along the longitudinal centerline 100 of the pull-on diaper 20. The outer side edge 46D and 48D is non-parallel to the inner side edge 46C and 48C and is non-parallel to the longitudinal centerline 100. The outer side edge 46D and 48D projects laterally outwardly proximate the lower end edge 46B and 48B. Therefore, the outer side edges 46D and 48D remote from the inner side edge 46C and 48C proximate the lower end edge 46B and 48B.

The extensible ear 46 and 48 has a lateral width L1 between the inner side edge 46C and 48C and the outer side edge 46D and 48D proximate the lower end edge 46B and 48B, and a lateral width L2 between the inner side edge 46C and 48C and the outer side edge 46D and 48D proximate the higher end edge 46A and 48A. The lateral width between the inner side edge and the outer side edge is the width between the inner side edge 46C and 48C and the outer side edge 46D and 48D in the lateral direction perpendicular to the longitudinal center line 100. Therefore, the lateral width between the inner side edge and the outer side is available in the range R where the inner side edges 46C and 48C and the outer side edge 46D and 48D co-extend in the longitudinal direction.

The lateral width L1 is greater than the lateral width L2, therefore, the available elastomeric material quantity in the lateral direction of the extensible ear 46 and 48 is greater proximate the lower end edge 46B and 48B than proximate the higher end edge 46A and 48A. Because the outer side edge 46D and 48D projects laterally outwardly proximate the lower end edge 46B and 48B, available elastomeric material quantity proximate the lower end edge 46B and 48B is enhanced without reducing available elastomeric material quantity proximate the higher end edge 46A and 48A. Further, the available elastomeric material quantity changes in the direction from the higher end edge 46A and 48A toward the lower end edge 46B and 48B because the lateral width of the extensible ear 46 and 48 gradually changes in that direction. This results in change of forces or force gradient over the extensible ear allowing for custom fit. The inner side edge 46C and 48C also can be non-parallel to the longitudinal center line 100 and project laterally inwardly proximate the lower end edge 46B and 48B such that the lateral width L1 becomes further greater than the lateral width L2. Alternatively, the inner side edge 46C and 48C can project a little laterally outwardly proximate the lower end edge 46B and 48B such that the lateral width L1 is still greater than the lateral width L2.

The extensible ear 46 and 48 can be formed by unitary elements of the pull-on diaper 20 (i.e., they are not separately manipulative elements secured to the pull-on diaper 20, but rather are formed from and are extended portions of one or more of the various layers of the pull-on diaper). In a preferred embodiment, the extensible ear 46 and 48 is a projected member of the chassis 41. Preferably, the extensible ear 46 and 48 comprises at least one unitary element or a continuous sheet material that forms a part of the chassis 41 and continuously extends to the extensible ear 46 and 48. Alternatively, the extensible ear 46 and 48 can be discrete members that do not have any unitary element that forms a part of the chassis 41. The extensible ear 46 and 48 can be formed by joining the discrete members to the side portions of the chassis 41.

The side elastic member 70 is interposed between the extended portion 72 of the inner barrier cuff 54 and the side extended portion 23C and 23D of the nonwoven outer cover 23 in the region of the extensible ear 46 and 48. The side elastic member 70 is operatively joined to at least one of the extended portion 72 of the inner barrier cuff 54 and the side extended portion 23C and 23D of the nonwoven outer cover 23. Preferably, the side elastic member 70 is operatively joined to both the extended portion 72 of the inner barrier cuff 54 and the side extended portion 23C and 23D of the nonwoven outer cover 23 while in a substantially untensioned (zero strain) condition.

The side elastic member 70 can be operatively joined to the inner barrier cuff 54 and the nonwoven outer cover 23, by using either an intermittent bonding configuration or a substantially continuous bonding configuration. Herein an "intermittently" bonded laminate web means a laminate web wherein the plies are initially bonded to one another at discrete spaced points or a laminate web wherein the plies are substantially unbonded to one another at discrete spaced areas. Conversely, a "substantially continuously" bonded laminate web means a laminate web wherein the plies are initially bonded substantially continuously to one another throughout the areas of interface. Because it is preferred that the stretch laminate be bonded over all or a significant portion of the stretch laminate so that the inelastic webs (i.e., nonwoven webs of the inner barrier cuff 54 and the nonwoven outer cover 23) elongate or draw without causing rupture, and the layers of the stretch laminates are preferably bonded in a configuration that maintains all of the layers of the stretch laminate in relatively close adherence to one another after the incremental mechanical stretching operation, the side elastic member and the other plies of the stretch laminate are substantially continuously bonded together using an adhesive.

In a particularly preferred embodiment, the adhesive selected is applied in a spiral pattern (such as is shown in U.S. Pat. No. 3,911,173 (Sprague, Jr.) and U.S. Pat. No. 4,842,666 (Werenicz)) at a basis weight of about 0.116 g/m². The spirals have a width of about 1.9 cm (0.75 in) and either are positioned just next to each other or overlap slightly (less than 2 mm). The adhesive is preferably an adhesive such as is available from Findley Adhesives under the designation H2120. Alternatively, the side elastic member and any other components of the stretch laminates can be intermittently or continuously bonded to one another using heat bonding, pressure bonding, ultrasonic bonding, dynamic mechanical bonding, or any other method as is known in the art.

After the side elastic member 70 is operatively joined to the extended portion 72 of the inner barrier cuff 54 and the side extended portion 23C and 23D of the nonwoven outer cover 23, at least a portion of the resultant composite stretch laminate is then subjected to mechanical stretching sufficient to permanently elongate the non-elastic components which are, for example, the extended portion 72 of the inner barrier cuff 54 and the side extended portion 23C and 23D of the nonwoven outer cover 23. The composite stretch laminate is then allowed to return to its substantially untensioned condition. The extensible ear 46 and 48 is thus formed into "zero strain" stretch laminates. (Alternatively, the side elastic member 70 could be operatively joined in a tensioned condition and then subjected to mechanical stretching.) Herein "zero strain" stretch laminate refers to a laminate comprised of at least two plies of material which are secured to one another along at least a portion of their coextensive surfaces while in a substantially untensioned ("zero strain") condition; one of the plies comprising a material which is stretchable and elastomeric (i.e., will return substantially to its untensioned dimensions after an applied tensile force has been released) and a second ply which is elongatable (but not necessarily elastomeric) so that upon stretching the second ply will be, at least to a degree, permanently elongated so that upon release of the applied tensile forces, it will not fully return to its original undeformed configuration. The resulting stretch laminate is thereby rendered elastically extensible, at least up to the point of initial stretching, in the direction of initial mechanical stretching.

Particularly preferred methods and apparatus used for making stretch laminates utilize meshing corrugated rolls or plates to mechanically stretch the components and are disclosed in U.S. Pat. No. 5,167,897, which issued to Weber et al. on Dec. 1, 1992; in U.S. Pat. No. 5,156,793, which issued to Buell et al. on Oct. 20, 1990; in U.S. Pat. No. 5,143,679, which issued to Weber et al. on Sep. 1, 1992 and in European Patent Application No. 98108290.2, entitled "Method and Apparatus for Activating a Moving Web," filed on Can 7, 1998 (Christoph J. Schmitz et al.).

The side elastic member 70 is preferably joined to, more preferably directly secured to, the side portions 68B of the inner barrier film 68 through an adhesive 76 as shown in FIG. 4. In a preferred embodiment, the side elastic member 70 is joined to the side portions 68B of the inner barrier film 68 at the outer-facing surface 77. In an alternative embodiment, the side elastic member 70 can be joined to the side portions 68B of the inner barrier film 68 at the body-facing surface 79. Preferably, the adhesive 76 is applied as a bead. The adhesive 76 can be applied as a spiral. In a preferred embodiment, the adhesive 76 is a flexible adhesive with an amorphous and crystallizing component. Such a preferred adhesive is supplied by the Findley Adhesive Company under the designation #H9224. Alternatively, the side elastic member 70 can be joined to the side portions 68B of the inner barrier film 68 by any other bonding means known in the art which comprise heat bonds, pressure bonds, ultrasonic bonds, dynamic mechanical bonds, or combinations of these attachment means.

Figure 6:
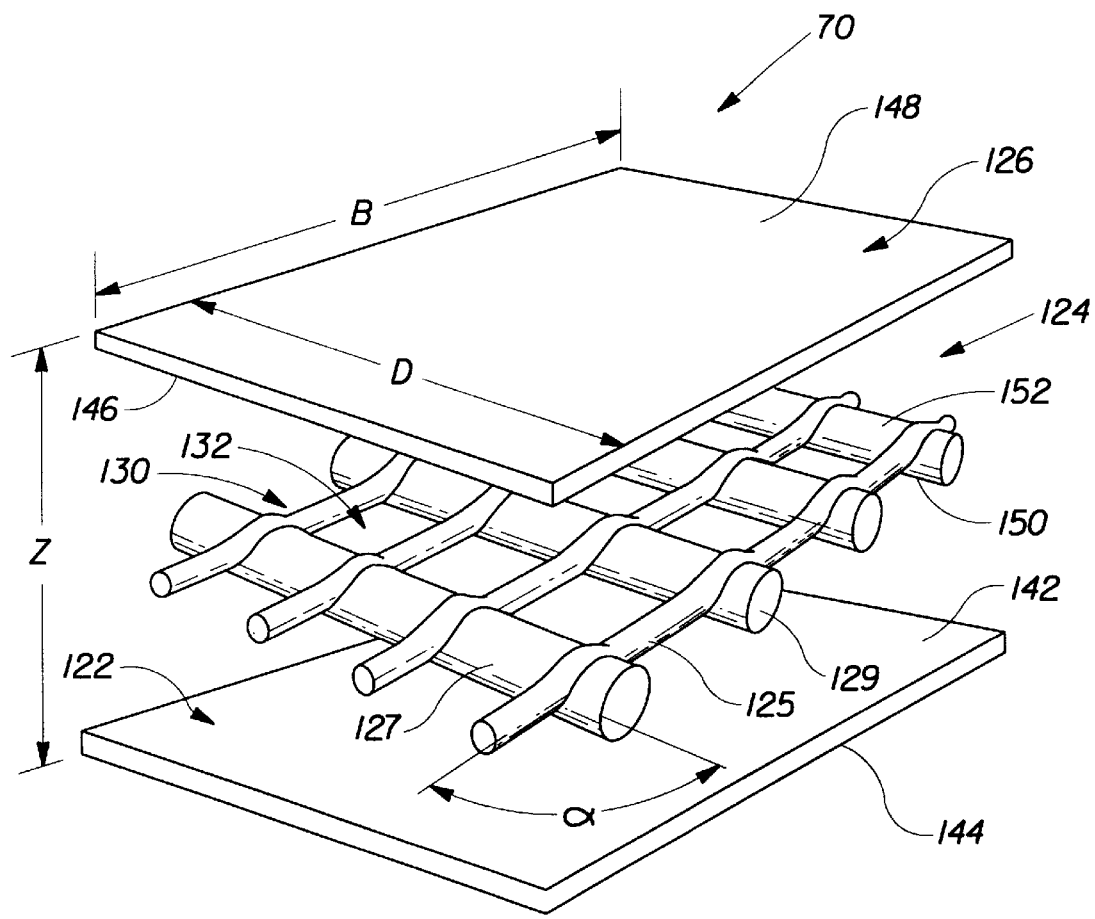
FIG. 6 is an enlarged, fragmentary perspective view in exploded form showing the structure of an elastic component of the garment.

The side elastic member 70 used for extensible ear 46 and 48, referring to FIG. 6, comprises the side elastomeric material 124. The side elastic material 70 can further include one of, preferably both of a first coverstock layer 122 and a second coverstock layer 126. Alternatively, the side elastic material 70 can not include any additional layer.

The side elastomeric material 124 has a first surface 150 and a second surface 152 opposing the first surface 150, and a first coverstock layer 122 which is joined to the first surface 150 of the side elastomeric material 124. In a preferred embodiment, the first coverstock layer 122 is joined to the first surface 150 of the side elastomeric material 124 by an adhesive. More preferably, the side elastic member 70 further comprises a second coverstock layer 126 which is joined to the second surface 152 of the side elastomeric material 124 by an adhesive 164. The side elastomeric material 124 provides a good fitness by generating the optimal retention (or sustained) force at the side area of the wearer. Preferably, the side elastomeric material 124 is extensible in at least one direction, preferably in a direction having a vector component in the lateral direction to generate a retention (or sustained) force that is optimal to prevent the pull-on diaper 20 from drooping, sagging, or sliding down from its position on the torso without causing undesired red marking on the skin of the wearer.

The side elastomeric material 124 can be formed in a wide variety of sizes, forms, and shapes. In a preferred embodiment, the side elastomeric material 124 is in the form of a continuous plane layer. Preferred forms of continuous plane layer include a scrim, a perforated (or apertured formed) film, an elastomeric woven or nonwoven, and the like. In an alternative embodiment, the side elastomeric material 124 is in the form of strands (or strings) which are not connected each other to form a continuous plane layer. The continuous plane layer can take any shape that can be suitably provided in the ear panels. Preferred shapes of continuous plane layer include a quadrilateral including a rectangle and a square, a trapezoid, and the other polygons.

Elastomeric materials which have been found to be especially suitable for the side elastomeric material 124 are styrenic block copolymer based scrim materials, perforated (or apertured) elastic films, strands, preferably with a thickness of from about 0.05 mm to about 1.0 mm (0.002 inch–0.039 inch). Other suitable elastomeric materials for the side elastomeric material 124 include "live" synthetic or natural rubber, other synthetic or natural rubber foams, elastomeric films (including heat shrinkable elastomeric films), elastomeric woven or nonwoven webs; elastomeric composites, or the like.

The extensibility properties of the side elastomeric material 124 such as the First Cycle Extension Force at 100% Extension (FCEF100%), the First Cycle Extension Force at 200% Extension (FCEF200%), the Second Cycle Recovery Force at 50% Extension (SCRF50%) and sustained load at 50% after 10–12 hours are important considerations in the performance of disposable garments. The side elastomeric material 124 preferably has extensibility properties within the ranges defined herein. The FCEF100% and the FCEF200% are measures of the overall perceived "stretchiness" during application/removal of disposable garments. These two properties also affect the ability of the applicator to achieve a suitable degree of application stretch. A side elastomeric material 124 with a relatively high FCEF100% and FCEF200% can cause difficulty in applying the disposable garment onto the wearer. On the other hand, a side elastomeric material 124 with a relatively low FCEF100% and FCEF200% can not achieve a suitable level of body fitting/conformity. The SCRF50% also closely relates to the body fitting/conformity of disposable garments for the wearer. A side elastomeric material 124 with a relatively high SCRF50% tends to cause red marking on the skin of the wearer and can be uncomfortable for the wearer during usage. A side elastomeric material 124 with a relatively low SCRF50% can not provide enough elastic force to keep the diaper in place on tie wearer or can not provide good body fit. The sustained load at 50% evaluates the force decay over time. This should be limited or substantial sagging will result. The values of FCEF100%, FCEF200%, and SCRF50% can be measured by using a tensile tester. The tensile tester comprises an upper jaw and a lower jaw that is located below the upper jaw. The upper jaw is movable and is connected to an extension force measuring means. The lower jaw is fixed on a desk (or floor). A test specimen (i.e., the elastomeric material to be measured) which has about 2.54 cm (1.0 inch) in width and about 12.75 cm (5 inches) in length is prepared and clamped between the upper jaw and the lower jaw so that the effective specimen length (L) (i.e., gauge length) is about 2.54 cm (1.0 inch). The extension force is applied to the test specimen through the upper jaw. When no extension force is applied to the test specimen, the test specimen is in its untensioned length. A tensile tester suitable for use herein is available from Instron Corporation (100 Royall Street, Canton, Mass. 02021, U.S.A.) as Code No. Instron 5564.

In preferred embodiments, the FCEF100% of the side elastomeric material 124 is at least about 100 grams/inch. More preferably, the FCEF100% is between about 120 to about 220 grams/inch, most preferably between about 150 grams/inch and 190 grams/inch. The FCEF200% is preferably between about 160 grams/inch and about 450 grams/inch, more preferably between about 180 grams/inch and about 300 grams/inch, and yet more preferably between about 200 grams/inch and about 240 grams/inch. The SCRF50% of the side elastomeric material 124 is preferably between about 40 grams/inch and about 130 grams/inch, more preferably between about 65 grams/inch and about 105 grams/inch, and yet more preferably between about 75 grams/inch and about 95 grams/inch. The sustained load at 50% is preferably between about 40 grams/inch and about 130 grams/inch, more preferably between about 65 grams/inch and about 105 grams/inch, and yet more preferably between about 75 grams/inch and about 95 grams/inch.

In the preferred embodiment shown in FIG. 6, the elastomeric scrim 124 has a plurality of first strands 125 and a plurality of second strands 127. The plurality of first strands 125 intersect the plurality of second strands 127 at nodes 130 at a predetermined angle α, forming a net-like open structure having a plurality of apertures 132. Each aperture 132 is defined by at least two adjacent first strands and at least two adjacent second strands, so that the apertures 132 are substantially rectangular in shape. Other configurations of the apertures 132, such as parallelograms, squares, or circular arc segments, can also be provided. Preferably, the first and second strands 125 and 127 are substantially straight and substantially parallel to one another. Preferably, the first strands 125 intersect the second strands 127 at nodes 130 such that the angle α is about 90 degrees. The first and second strands 125 and 127 are preferably joined or bonded at nodes 130. A preferred elastomeric scrim 124 is manufactured by the Conwed Plastics Company under the designation XO2514. This material has about 12 elastic strands per inch in the structural direction B (i.e., the first strands 125) and about 7 elastic strands per inch in the structural direction D (i.e., the second strands 127).

In another embodiment elastomeric material 124 can include a porous, macroscopically-expanded, three-dimensional elastomeric apertured web. The detail of such a structure and the method to manufacture is disclosed in U.S. patent application Ser. No. 08/816,106, filed Mar. 14, 1997. A preferred porous elastomeric material is manufactured by Tredegar Film Products under the designation X-25007. The apertures can have any desired shape. Preferably, the apertures have a shape having a major axis and a minor axis perpendicular to each other, such as an oval shape, and the major axis is preferably oriented generally orthogonal to applied strain-induced stresses.

In the embodiment shown in FIG. 6, the side elastic member 70 comprises first and second coverstock layers 122 and 126, and side elastomeric material 124 disposed in the first and second coverstock layers 122 and 126. The first coverstock layer 122 has an inner surface 142 and an outer surface 144. The inner surface 142 of the first coverstock layer 122 is the surface that is positioned faging the side elastomeric material 124. The second coverstock layer 126 also has an inner surface 146 and an outer surface 148. The inner surface 146 of the second coverstock layer 126 is the surface that is positioned facing the side elastomeric material 124. The side elastomeric material 124 also has two planar surfaces, first surface 150 and second surface 152, each of which is substantially parallel with the planes of the first and second coverstock layers 122 and 126. The first surface 150 is that planar surface of the side elastomeric material 124 that is most closely adjacent with the inner surface 142 of first coverstock layer 122. The second surface 152 is that planar surface of side elastomeric material 124 that is most closely adjacent to the inner surface 146 of the second coverstock layer 126.

Since the side elastic member 70 will be subjected to mechanical stretching before and during use, the first and second coverstock layers 122 and 126 preferably has a relatively high elongation at breaking, and are more preferably stretchable or elongatable, yet more preferably drawable (but not necessarily elastomeric), without undue and preferably without any, tearing or ripping. Further, the first and second coverstock layers 122 and 126 are preferably compliant, soft feeling, and non-irritating to the wearer's skin and give the article the feel and comfort of a cloth garment. Suitable materials for the first and second coverstock layers 122 and 126 can be manufactured from a wide range of materials such as plastic films, apertured plastic films, woven or nonwoven webs of natural fibers (e.g., wood or cotton fibers), synthetic fibers (e.g., polyolefins, polyamides, polyester, polyethylene, or polypropylene fibers), or a combination of natural and/or synthetic fibers, or coated woven or nonwoven webs.

Preferably, each of the first and second coverstock layers 122 and 126 is an identical nonwoven material. An exemplary preferred nonwoven material is manufactured by the FiberWeb Company under the designation DAPP-S tex having a basis weight in the range of 18–35 g/m$^2$. The nonwoven can be consolidated or not consolidated.

Preferably, the nonwoven is consolidated for the use of a coverstock layer for an elastomeric scrim. This material has a basis weight in the range of 18–35 g/m² before consolidation and a basis weight in the range of about 40–70 g/m² after consolidation. As used herein, "basis weight" is the weight per unit area of planar web material, one square meter in this instance. Alternatively, highly strainable nonwoven materials can be used. Alternatively, the first and second coverstock layers 122 and 126 need not be of identical materials, as long as the desired performance requirements, such as elastic performance, softness, flexibility, breathability and durability, are met. As used herein, "consolidated nonwoven material" refers to a nonwoven material that has been gathered or necked under mechanical tension in the structural direction D so that the material can elongate in the structural direction D under low force.

Referring to FIG. 1, the pull-on diaper 20 further has the continuous extensible waist feature 60. The continuous extensible waist feature 60 improved fit, ease of application and containment. The continuous extensible waist feature 60 is that portion or zone of the pull-on diaper 20 which is intended to be elastically extensible and contract to dynamically fit the wearers waist. The continuous extensible waist feature 60 extends along the waistband panel 6 and 7. Preferably, the continuous extensible waist feature 60 comprises two separate elements; one continuous extensible waistband 57 positioned in the front region 26, and the other continuous extensible waistband 59 positioned in the back region 28, although other pull-on diapers can be constructed with a single continuous extensible waistband.

Referring to FIG. 5 as well, the continuous extensible waistband 57 and 59 preferably comprises a waist elastic member 80 having the waist elastomeric material 200 (shown in FIG. 6) and an extended portion of at least one of the plurality of layers disposed associated with the absorbent core 25, such as the topsheet 24 and the backsheet 22 (although FIG. 5 shows only the structures in the front region 26, preferably the structures in the back region 28 are the same or similar to those in the front region 26). Preferably the continuous extensible waistband 57 and 59 is elastically extensible in at least the lateral direction, more preferably both in the lateral and longitudinal directions. In a preferred embodiment, the waistband panel 6 and 7 is rendered extensible at least in the entire lateral length of the waistband panel 6 and 7 to form the continuous extensible waistband 57 and 59 by the waist elastic member 80.

In the embodiment shown in FIG. 3, the waist elastic member 80 can extend into the seam panel 12 and 13 so that the continuous extensible waistband 57 and the continuous extensible waistband 59 are anchored each other at the seam 32, and the waist elastic material 80 in the front region 26 and the elastic material 80 in the back region 28 are anchored at the seam 32 (FIG. 5 also shows the waist elastic member 80 which extends into the seam panel 12 and 13, though the seam panel 12 and 13 is not shown in FIG. 5). The continuous extensible waistband 57 and 59 forms one continuous extensible waist feature 60 in an assembled configuration of the pull-on diaper 20 as shown in FIG. 1.

The continuous extensible waistband 57 and 59 can be formed by unitary elements of the pull-on diaper 20 (i.e., they are not separately manipulative elements secured to the pull-on diaper 20, but rather are formed from and are extended portions of one or more of the various layers of the pull-on diaper). In a preferred embodiment, each of the continuous extensible waistband 57 and 59 comprises a projected member of the chassis 41. Preferably, the continuous extensible waistband 57 and 59 comprises at least one unitary element or a continuous sheet material that forms a part of the chassis 41 and continuously extends into the continuous extensible waistband 57 and 59. Alternatively, the continuous extensible waistband 57 and 59 can be discrete members that do not have any unitary element that forms a part of the chassis 41. The continuous extensible waistband 57 and 59 can be formed by joining the discrete members to the waist portions of the chassis 41.

The continuous extensible waistband 57 and 59 comprises the waist elastic member 80 and an extended portion of at least one of the plurality of layers disposed associated with the absorbent core 25, such as the topsheet 24 and the backsheet 22. If an additional layer, such as the inner barrier cuff 54 or an additional liquid absorbing tissue layer, is added associated with the absorbent core 25, the additional layer can form a part of the continuous extensible waistband 57 and 59. In a preferred embodiment shown in FIG. 7, the side portion 57B of the continuous extensible waistband 57 comprises a lamination of an extended portion 72 of the inner barrier cuff 54, the end extended portion 23A of the nonwoven outer cover 23, and a side part of the waist elastic member 80. The central portion 57A of the extensible waistband 57 comprises a lamination of the end extended portion 24A of the topsheet 24, the end extended portion 23A of the nonwoven outer cover 23, and a center part of the waist elastic member 80 (although FIG. 5 shows only the structures in the front region 26, preferably the structures in the back region 28 are the same or similar to those in the front region 26). However, in the embodiment, the inner barrier film 68 does not extend into the continuous extensible waistband 57. Alternatively, the inner barrier cuff 54, the topsheet 24, and/or the nonwoven outer cover 23 can not extend into the continuous extensible waistband 57. The extended portion 72 of the inner barrier cuff 54 also can not extend into the continuous extensible waistband 57. If both of the topsheet 24 and the nonwoven outer cover 23 do not extend into the continuous extensible waistband 57, the continuous extensible waistband 57 can comprise an extended portion of the inner barrier film 68 and the waist elastic member 80.

The waist elastic member 80 overlies a portion of the body-facing surface of the pull-on diaper 20. The waist elastic member 80 can be operatively joined to the extended portions 72 of the inner barrier cuffs 54, the end extended portion 23A of the nonwoven outer cover 23, and the end extended portion 24A of the topsheet 24. The waist elastic member 80 can be operatively joined thereto, by using either an intermittent bonding configuration or a substantially continuous bonding configuration. In a particularly preferred embodiment, the adhesive selected is applied in a spiral pattern (such as is shown in U.S. Pat. No. 3,911,173 (Sprague, Jr.) and U.S. Pat. No. 4,842,666 (Werenicz)) at a basis weight of about 0.116 g/m². The spirals have a width of about 1.9 cm (0.75 in) and either are positioned just next to each other or overlap slightly (less than 2 mm). The adhesive is preferably an adhesive such as is available from Findley Adhesives under the designation H2120. Alternatively, the waist elastic member and any other components of the stretch laminates can be intermittently or continuously bonded to one another using heat bonding, pressure bonding, ultrasonic bonding, dynamic mechanical bonding, or any other method as is known in the art.

The entire unstrained length of the waist elastic member 80 is preferably prestrained in the lateral direction before operatively joined to the extended portions 72 of the left and right inner barrier cuffs 54, the end extended portion 24A of the topsheet 24, and the end extended portion 23A of the nonwoven outer cover 23. The entire unstrained length of the waist elastic member 80 is prestrained in the lateral direction up to at least the original length of the waistband panel 6 and 7 of the chassis 41. The entire unstrained length of the waist elastic member 80 can be further prestrained to extend into a part of the seam panel 12 and 13. In the embodiment, the waistband panel 6 and 7 of the chassis 41 comprises the extended portions 72 of the left and right inner barrier cuffs 54, the end extended portion 24A of the topsheet 24, and the end extended portion 23A of the nonwoven outer cover 23.

Herein "original length" refers to the length of a single material or a composite material before being rendered elastically extensible and before being permanently mechanically stretched. Herein "prestrained entire length" refers to the entire length of an elastic material under a condition where a part of or the entire length of the elastic material is prestrained in the lateral direction.

In the embodiment, the original length of the waistband panel 6 and 7 is generally the same as the combined length of the extended portions 72 of the left and right inner barrier cuffs 54 and the end extended portion 24A of the topsheet 24 under an assembled configuration before the waist elastic member 80 is joined thereto. The original length of the waistband panel 6 and 7 is also generally the same as the length of the end extended portion 23A of the nonwoven outer cover 23 before the waist elastic member 80 is joined thereto. The waist elastic member 80 is preferably prestrained in range of from 20 to 100% of its unstrained (i.e. untensioned) length. More preferably, the waist elastic member 80 can be prestrained in range of from 40 to 80%. After the prestrained waist elastic member 80 is jkined, the waist elastic member 80 is then allowed to return to their substantially untensioned condition with the other components, such as the extended portions 72 of the inner barrier cuffs 54, the end extended portion 24A of the topsheet 24, and the end extended portion 23A of the nonwoven outer cover 23, joined to the waist elastic member 80. Thus the continuous extensible waistband 57 and 59 is formed that is extensible, from the untensioned length of the waist elastic member 80 at least to the original length of the waistband panel 6 and 7 of the chassis 41.

Alternatively, only a part of the waist elastic member 80 can be prestrained before operatively joined to the extended portion of at least one of the plurality of layers, such that the prestrained entire length of the waist elastic member 80 in a condition where a part of the waist elastic member 80 is prestrained is generally the same as the original length of the waistband panel 6 and 7 of the chassis 41. Preferably, only a part of the waist elastic material 80, which extends along the lateral width X (shown in FIG. 3) of the absorbent core 25 adjacent to the waist elastic material 80, can be prestrained.

Examples of extensible materials are disclosed in U.S. Pat. No. 2,075,189, which issued to Galligan on Mar. 30, 1937; in U.S. Pat. No. 3,025,199, which issued to Harwood on Mar. 13, 1962; in U.S. Pat. Nos. 4,107,364 and 4,209, 563, which issued to Sisson on Aug. 15, 1978, and on Jun. 24, 1980, respectively; in U.S. Pat. No. 4,834,741, which issued to Sabee on May 30, 1989; and in U.S. Pat. No. 5,151,092, which issued to Buell et al., on Sep. 29, 1992.

The continuous extensible waistband 57 and 59 is formed to be extensible, from the untensioned length of the waist elastic member 80 at least up to the original length of the waistband panel 6 and 7 of the chassis 41. However, the waist elastic member 80 is usually joined to the extended portion of at least one of the plurality of layers disposed associated with the absorbent core 25, such as the topsheet 24 and the backsheet 22 which are substantially non-elastic. Therefore, the waist elastic member 80 can extend only between the untensioned length of the waist elastic member 80 and the original length of the waistband panel 6 and 7 of the chassis 41, and can not extend beyond the original length of the waistband panel 6 and 7 of the chassis 41. This restricts the upper limit of the extension range of the continuous extensible waistband 57 and 59 (i.e., continuous extensible waist feature 60), even if the waist elastomeric material 80 itself is capable of extending beyond the original length of the waistband panel 6 and 7 of the chassis 41 or the prestrained entire length of the waist elastomeric material 80. This restriction in the upper limit of the extension range does not allow enough extensibility for the continuous extensible waistband 57 and 59. Therefore, when the pull-on diaper 20 is extended for application to the wearer, the pull-on diaper 20 can not provide enough size of waist opening or the applicator must apply much high force to the pull-on diaper 20 to seek extensibility from other extensible materials in the pull-on diaper 20 to obtain enough size of waist opening. This can cause difficulty in applying the pull-on diaper to the wearer.

Therefore, the continuous extensible waistband 57 and 59 is rendered elastically extensible to provide greater range of extensibility (i.e., extension range) beyond the original length of the waistband panel 6 and 7 of the chassis 41 or the prestrained entire length of the waist elastic member 80. Namely, after the waist elastic member 80 is operatively joined under a prestrained (tensioned) condition to the inner barrier cuff 54, the topsheet 24 and the nonwoven outer cover 23 and before returning to their substantially untensioned condition, at least a portion of, preferably the entire of the resultant composite stretch laminate (i.e., continuous extensible waistband 57 and 59) is then subjected to mechanical stretching sufficient to permanently elongate the non-elastic components which are the extended portions 72 of the left and right inner barrier cuffs 54, the end extended portion 24A of the topsheet 24, the end extended portion 23A of the nonwoven outer cover 23, and the coverstock layers (if any) constituting a part of the waist elastic member 80. The composite stretch laminate is then allowed to return to its substantially untensioned condition. Therefore, the waist elastic member 80 is extensible from the untensioned length beyond the original length of the waistband panel 6 and 7 of the chassis 41 at least up to the permanently elongated length of the non-elastic components. This provides wider extension range for the continuous extensible waistband 57 and 59, thereby providing a benefit of ease of application. Alternatively the waist elastic member 80 can be joined to the inner barrier cuffs 54, the topsheet 24 and the nonwoven outer cover 23 in a substantially untensioned (zero strain) condition so as to form a "zero strain" stretch laminate. Preferred apparatus and methods are disclosed in U.S. Pat. No. 5,167,897 issued to Weber et al. on Dec. 1, 1992; U.S. Pat. No. 5,156,793 issued to Buell et al. on Oct. 20, 1990; U.S. Pat. No. 5,143,679 issued to Weber et al. on Sep. 1, 1992 and European Patent Application No. 98108290.2 titled "METHOD AND APPARATUS FOR ACTIVATING A MOVING WEB" filed on Can 7, 1998 (Christoph J. Schmitz et al.).

The waist elastic member 80 comprises the waist elastomeric material 200, which can use the same material/ structure as the side elastomeric material 124. Alternatively, the waist elastomeric material 200 can use material/structure different from the side elastomeric material 124. The waist elastic member 80 can further include one of, or both of a first coverstock layer 202 and a second coverstock layer 204. The structure of the waist elastic member 80 can be the same or similar to that of the side elastic member 70. The structure, materials and/or properties of the coverstock layers 202 and 204 can be the same or similar to those of the coverstock layers 122 and 126, or can be different from those. Further, the method to join the waist elastomeric material 200 to the coverstock layers 202 and 204 can be the same or similar to the method of those described for the ear panel member 70 above, or can be different from those. In a preferred embodiment, the waist elastic member 80 comprises the waist elastomeric material 200 and one layer of the coverstock layer 202 or 204. In such a case, the waist elastomeric material 200 is disposed facing the inner barrier cuffs 54 and the topsheet 27, and the coverstock layer 202 or 204 is disposed so as to face and contact the wearer's body. such that the wearer's skin is not directly pressed by the waist elastomeric material 200 thereby reducing the incidence of red marking on the skin.

In one embodiment, the waist elastic member 80 can comprise the waist elastomeric material 200 and one layer of the coverstock layer 202 or 204. In one case, the waist elastomeric material 200 is disposed facing the inner barrier cuffs 54 and the topsheet 24, and the coverstock layer 202 or 204 is disposed facing the nonwoven outer cover 23. This disposition of the coverstock layer tends to inhibit the waist elastomeric material 200 is seen through from the outside because one layer (coverstock layer) is added to interpose between the waist elastomeric material 200 and the nonwoven outer cover 23. In another case, the waist elastomeric material 200 is disposed facing the nonwoven outer cover 23, and the coverstock layer 202 or 204 is disposed facing the inner barrier cuffs 54 and the topsheet 27. This disposition of the coverstock layer tends to reduce the incidence of red marking on the skin because one layer (coverstock layer) is added to interpose between the waist elastomeric material 200 and the skin of the wearer. In both cases, because one of the coverstock layers is eliminated (compared with two layers of the coverstock layers), bulkiness in the continuous extensible waistband 57 reduces. Further, breathability at the continuous extensible waistband 57 enhances because of less material therein, In addition, the continuous extensible waistband 57 becomes to have more available extensibility. The continuous extensible waistband 57 is formed by the waist elastic member 80 comprising the waist elastomeric material 200 which is prestrained and then returned to the original untensioned condition in a preferred embodiment. When the waist elastomeric material 200 returns to its original untensioned condition, the other components joined to the waist elastomeric material 200 tends to inhibit the waist elastomeric material 200 to return its original untensioned length. Therefore, the waist elastomeric material 200 can not utilize the whole extensibility. However, in the embodiment described above, since bulkiness in the continuous extensible waistband 57 reduces, the waist elastomeric material 200 can return as close as its original untensioned length. Therefore, the waist elastomeric material 200 becomes to have more available extensibility.

Alternatively, the waist elastic member 80 can comprise one layer of the waist elastomeric material 200 without any coverstock layers. In the side portions 57B of the extensible waistband 57, the waist elastomeric material 200 is interposed and joined directly between the extended portions 72 of the inner barrier cuffs 72 and the end extended portion 23A of the nonwoven outer cover 23. In the central portion 57A, the waist elastomeric material 200 is interposed and joined directly between the end extended portion 24A of the topsheet 24 and the nonwoven outer cover 23. This structure is also useful to reduce bulkiness, to enhance breathability, and to have more available extensibility, in the extensible waistband 57.

The side elastic member 70 and the waist elastic member 80 consist of separate elements and both members 70 and 80 are preferably disposed not to overlap to each other in the longitudinal direction. However, both members 70 and 80 are preferably disposed without a substantial gap therebetween such that the members 70 and 80 form a composite elastomeric network in the extensible ears 46 and 48.

Herein "composite elastomeric network" refers to a zone or area where two or more separate elastomeric materials substantially continue with no gap between the elastomeric materials or with a predetermined interval thereby exhibiting a behavior of extensibility like a single elastomeric material.

Preferably, both members 70 and 80 are disposed with no gap. Therefore, it is perceived that the extensible ear 46 and 48 and the side portion 57B and 59B of the continuous extensible waistband 57 and 59 comprise a continuous single elastomeric material between the waist opening 36 and the leg openings in an assembled configuration of the pull-on diaper 20. The side elastic member 70 and the waist elastic member 80 consist of separate elements; therefore the side elastomeric material 124 and the waist elastomeric material 200 also consist of separate elements.

The separated structure allows the design of the side elastomeric material 124 and the waist elastomeric material 200 using different materials in each components, so this allows different properties of extensibility such as force versus extension curve for different parts of the pull-on diaper 20. The separated structure also allows use of the side elastomeric material 124 and the waist elastomeric material 200 in different conditions, such as in a prestrained (tensioned) condition or untensioned condition. This allows differentiation of the force required to extend different parts of the pull-on diaper 20 up to the same length or equalize force required to extend different parts up to the different length, thereby adjusting the pressure applied to the skin of the wearer. For example, the pull-on diaper 20 can have a waist elastomeric material 200 provided with high extensibility at low force such that the continuous extensible waist feature 60 is extended easily by low force applied by the applicator for ease of application of the pull-on diaper 20 while the pull-on diaper 20 can have a side elastomeric material 124 generating force required for sustained fit at the extensible ear 46 and 48, but the force can not give red marking to the skin. In one embodiment, the continuous extensible waist feature 60 comprising the waist elastomeric material 200 is designed to have extensibility of at least 100% while the extensible ear 46 and 48 comprising the side elastomeric material 124 is designed to have force between 40 g/inch and 130 g/inch when the extensible ear 46 and 48 is extended up to 50% (more concretely, at SCRF50%).

Both the side elastic member 70 and the waist elastic member 80 are disposed not to overlap to each other in the longitudinal direction; therefore, the side elastomeric material 124 and the waist elastomeric material 200 also do not overlap. Because the side elastic member 70 and the waist elastic member 80 are not structurally overlapped, each member 70 and 80 comprises a single material of extensibility; therefore it has substantially homogeneous property of extensibility. This allows the applicator to extend the pull-on diaper 20 smoothly without feeling the change of force applied during extending for application of the pull-on diaper.

The seams 32 each joins the seam panels 12 and 13, thereby joining the corresponding portions of the extensible ears 46 and 48, and thereby forming two leg openings 34 and one waist opening 36. The front and back extensible ears 46 and 48 are seamed, preferably, along the outer side edges 46D and 48D, in an overlapped manner to make an overlapped seam structure. Alternatively, the front and back extensible ears 46 and 48 can be seamed in a butt seam manner (not shown) known to those skilled in the art. The bonding of the seams 32 can be performed by any suitable means known in the art appropriate for the specific materials employed in the front and back extensible ears 46 and 48. Thus, sonic sealing, heat sealing, pressure bonding, adhesive or cohesive bonding, sewing, autogeneous bonding, and the like can be appropriate techniques. Preferably, the seam panels 12 and 13 are joined by a predetermined pattern of heat/pressure or ultrasonic welds which withstands the forces- and stresses generated on the pull-on diaper 20 during wear. The seams 32 also connect the continuous extensible waistbands 57 and 59 to form the continuous extensible waist feature 60 about the waist opening 36. When the side elastic member 70 and the waist elastic member 80 extend into the seam panel 12 and 13, the seams 32 anchor the side elastic member 70 in the front region 26 to the side elastic member 70 in the back region 28 and anchor the waist elastic member 80 in the front region 26 to the waist elastic member 80 in the back region 28. Examples of seams are disclosed in U.S. Pat. No. 5,569,234 issued to Buell, et al. on Oct. 29, 1996, U.S. Pat. No. 5,607,537 issued to Johnson et al. on Mar. 4, 1997, U.S. Pat. No. 5,662,638 issued to Johnson et al. on Sep. 2, 1997, and U.S. Pat. No. 5,685,874 issued to Buell et al. on Nov. 11, 1997. Preferable seams are disclosed in European Patent Application No. 96118654.1 titled "Thermal Joining of Webs" filed on Nov. 21, 1996 (Christoph J. Schmitz).

In a preferred embodiment, the outer side edge 46D and 48D is non-parallel to the inner side edge 46C and 48C and is non-parallel to the longitudinal centerline 100. The outer side edge 46D and 48D projects laterally outwardly proximate the lower end edge 46B and 48B. The extensible ear 46 and 48 has a lateral width L1 between the inner side edge 46C and 48C and the outer side edge 46D and 48D proximate the lower end edge 46B and 48B greater than a lateral width L2 between the inner side edge 46C and 48C and the outer side edge 46D and 48D proximate the higher end edge 46A and 48A. Therefore, the available elastomeric material quantity in the lateral direction of the extensible ear 46 and 48 is greater proximate the lower en edge 46B and 48B than proximate the higher end edge 46A and 48A. The extensibility proximate the lower end edge 46B and 48B is enhanced. In addition, because both extensible ear 46 and extensible ear 48 have greater lateral width (i.e., available elastomeric material quantity) proximate the lower end edge 46B and 48B, lateral width (i.e., available elastomeric material quantity) further becomes greater proximate the lower end edge 46 B and 48B by combining the extensible ear 46 and the extensible ear 48. Because of the configuration being greater in width proximate the lower end edge 46B and 48B, the pull-on diaper has more elastomeric material quantity available about the leg openings while the pull-on diaper maintains elastomeric material quantity about the waist opening. Therefore, the pull-on diaper does not give too high pressure to the skin causing the negative skin incidence about the leg openings while maintaining a sustained fit about the waist opening.

Further, as explained hereinabove, the waist elastic member 80 is joined to the waistband panel 6 and 7 of the chassis 41 in a tensioned (prestrained) condition and allowed to return to the substantially untensioned condition while the side elastic member 70 is joined to the extensible ear 46 and 48 in an untensioned condition. Therefore, the circumference of the pull-on diaper 20 about the continuous extensible waist feature 60 further becomes smaller under an untensioned condition than the circumference of the pull-on diaper 20 through a portion of the extensible ear 46 and 48. This configuration further improves a sustained fit about the waist opening while reducing the skin incidence about the leg openings. Herein "circumferential direction" refers to a direction along the waist opening in an assembled configuration of the pull-on diaper. Herein "circumference" refers to a length of the pull-diaper along the circumferential direction.

The continuous belt zone 38 is formed by the front and back extensible ears 46 and 48, a part of the chassis 41, and the continuous extensible waist feature 60 as shown in FIG. 1. The continuous belt zone is that portion or a belt-like zone of the pull-on diaper that is extensible such that the circumference of the continuous belt zone is extended for application of the pull-on diaper 20. When the pull-on diaper 20 is applied to the wearer, the pull-on diaper 20 must be extended to secure wider waist opening and wider leg opening for ease of application of the pull-on diaper 20. The continuous belt zone 38 is that portion capable of being extended. The continuous belt zone 38 is, in an assembled configuration shown in FIG. 1, encompassed by the waist edge 151 and 155 of the pull-on diaper 20, the leg edge 153 and 156, the lateral edge 159 of the crotch region 30 in the front region 26 and the back region 28. The continuous belt zone 38 has the least height typically at the ear panels. In the embodiment shown in FIG. 1, the least height of the continuous belt zone 38 is measured along the seams 32. The continuous belt zone 38 also has a continuous lowermost line 35, which is not interrupted by the leg openings 34, but is the closest to the leg openings 34. The continuous belt zone 38 has two portions, a continuous waist belt zone 37 in which the continuous extensible waist feature 60 extends, and a continuous lower belt zone 39 in which the extensible ears 46 and 48 and a part of the chassis 41 extend. In a preferred embodiment, the continuous waist belt zone 37 conforms with the continuous extensible waist feature 60.

In one preferred embodiment where the pull-on diaper shown in FIG. 3 becomes an assembled configuration as shown in FIG. 1, the initial circumference of the continuous belt zone 38 along the waist edge 151 and 155 can be from 200 mm to 500 mm in an untensioned condition, preferably from 250 mm to 400 mm. The circumference of the continuous belt zone 38 along the waist edge 151 and 155 extends up to at least 650 mm, preferably at least 700 mm, more preferably at least 750 mm (extended circumference). The circumference of the continuous belt zone 38 along the line 35 can be from 300 mm to 550 mm, preferably from 350 mm to 500 mm. The least height of the continuous belt zone 38 measured along the seams 32 can be from 50 mm to 150 mm, preferably from 80 mm to 120 mm. The height of the continuous waist belt zone 37 (i.e., continuous extensible waist feature 60) can be from 5 mm to 40 mm, preferably from 15 mm to 30 mm. The combined lateral length of the extensible ears 46 and 48 in one side of the pull-on diaper 20 along the line 35 is from 50 mm to 120 mm, preferably from 60 mm to 100 mm.

The pull-on diaper having a configuration shown in FIG. 3, when it becomes an assembled configuration, lowers the pressure to the skin of the wearer locally especially about the leg openings 34 because the extensible ear 46 and 48 has greater lateral width (available extensibility in the lateral direction) proximate the lower end edge 46B and 48B. If necessary, the side elastomeric material 124 can use a material having lower SCRF50% force to further lower the pressure about the leg openings 34. However, lowering the SCRF50% force about the leg openings 34 can result in losing sustained fit for the whole pull-on diaper. Therefore, raising the pressure about the waist opening 36 can be necessary to achieve a sustained fit for the whole pull-on diaper. This can be achieved by prestraining only the waist elastomeric material 200 before joining to the waistband panel 6 and 7. In addition, the waist elastomeric material 200 can use a material having a higher SCRF50% force to further raise the pressure about the waist opening 36. These combinations of force distributions allow the pull-on diaper to achieve a sustained fit about the waist opening with less incidence of red marking on the skin about the leg openings. Alternatively, the pull-on diaper having a configuration shown in FIG. 3, when it becomes an assembled configuration, can provide a sustained fit about the leg openings and less incidence of red marking on the skin about the waist opening. This can be achieved, for example, using a material having lower SCRF50% force for the waist elastomeric material 200 to lower the pressure about the waist opening 36. The side elastorneric material 124 can use a material having a lower SCRF50% force. Further, the side elastomeric material 124 can be prestrained before joining to the ear panel 6 and 7.

The continuous belt zone 38 contributes to dynamically create fit force in the pull-on diaper 20 when positioned on the wearer, to maintain the pull-on diaper 20 on the wearer. Although higher fit force generated by the continuous belt zone 38 is preferable for sustained fit for the pull-on diaper, the continuous belt zone 38 generating the higher fit force causes difficulty in applying the pull-on diaper to the wearer because the applicator of the pull-on diaper must apply higher force to the pull-on diaper to extend the continuous belt zone 38 such that the wider waist opening and wider leg openings are secured. Because the continuous belt zone 38 comprises the side elastomeric material 124 and the waist elastomeric material 200, both elastomeric materials must be extended during the process of pulling on the pull-on diaper. Therefore, the property of extensibility of the continuous belt zone 38 including the side and waist elastomeric materials are more important than those of a solo continuous extensible waist feature 60 and/or those of a solo extensible ear 46 and 48, though the property of extensibility of a solo continuous extensible waist feature 60 and/or a solo extensible ear 46 and 48 are still important. U.S. Pat. No. 5,601,547, which issued on Feb. 11, 1997, to Kato, et al. discloses a waist elastic system with improved modulus of elasticity for a child's training pant providing a more comfortable fit and improved ease of use. However, that patent is directed only to improvement of the waist elastic system.

The continuous belt zone 38 is extensible in the extension range from an initial extension (i.e., 0%). The extension is calculated from the equation:

((extended circumference−initial circumference)/initial circumference)×100 and expressed in the unit of % (percent). The initial circumference of the continuous belt zone 38 is the circumference under an untensioned condition of the continuous belt zone 38. The extended circumference is the circumference under an extended condition of the continuous belt zone 38. The wider extension range allows securing the wider waist opening and the wider leg openings for application of the pull-on diaper 20. The wider extended circumference allows securing the wider space between the extended pull-on diaper and the body of the wearer for application of the pull-on diaper 20. The circumference of the continuous belt zone 38 is the circumference measured along the waist border of the continuous belt zone 38 (i.e., the waist edges 151 and 155 of the continuous extensible waist feature 60).

In order to provide a benefit of ease of application of the pull-on diaper (i.e., wider waist opening and wider leg openings), the initial circumference of the continuous belt zone 38 of the pull-on diaper can be between about 220 mm and about 500 mm, and the extended circumference of the continuous belt zone 38 of the pull-on diaper is at least about 650 mm. More specifically, the initial circumference of the continuous belt zone 38 of the pull-on diaper designed to fit toddlers weighing from about 7 kg to about 10 kg is between about 220 mm and about 460 mm, preferably about 250 mm and about 360 mm. The initial circumference of the continuous belt zone 38 of the pull-on diaper designed to fit toddlers weighing from about 9 kg to about 14 kg is between about 240 mm and about 480 mm, preferably about 270 mm and about 380 mm. The initial circumference of the continuous belt zone 38 of the pull-on diaper designed to fit toddlers weighing about 13 kg or above is between about 260 mm and about 500 mm, preferably about 290 mm and about 400 mm. The extended circumference of the continuous belt$zone 38 of the pull-on diaper designed to fit toddlers weighing from about 7 kg to about 10 kg is at least about 650 mm, preferably about 700 mm. The extended circumference of the continuous belt zone 38 of the pull-on diaper designed to fit toddlers weighing from about 9 kg to about 14 kg is at least about 700 mm, preferably about 750 mm. The extended circumference of the continuous belt zone 38 of the pull-on diaper designed to fit toddlers weighing about 13 kg or above is at least about 750 mm, preferably about 800 mm. The pull-on diaper has the extension range up to at least the extension of about 125%, preferably about 135%, more preferably about 150%.

The continuous belt zone 38 also has a force versus extension curve in the extension range and a modulus of extensibility in the extension range. The force versus extension curve represents a relationship of a force required to extend the continuous belt zone 38 and an extension of the continuous belt zone 38. The modulus of extensibility represents a rate of force change to extension change and is expressed in the unit of g/% extension (grams/percent extension). The method to obtain the modulus of extensibility is set forth below. The higher modulus of extensibility means higher rate of force change to extend the continuous belt zone 38. When modulus of extensibility becomes dramatically high, the applicator recognizes that part as a limitation of extension. Conversely, the lower modulus of extensibility means lower rate of force change to extend the continuous belt zone 38. This allows the applicator to extend the continuous belt zone 38 without adding higher force, and the applicator can not recognize the limitation of extension. Therefore, it is preferable the continuous belt zone 38 has lower modulus of extensibility at the extended circumference for application of the pull-on diaper. In addition, the lower force to extend the pull-on diaper up to the extended circumference for application of the pull-on diaper is preferable. In order to provide a benefit of ease of application of the pull-on diaper (i.e., lower force to obtain the extension for application of the pull-on diaper and lower modulus of extensibility at the extension for application of the pull-on diaper), the modulus of extensibility at the extension of 125% is not greater than about 150 g/% extension, preferably not greater than about 120 g/% extension, more preferably not greater than about 100 g/% extension. The modulus of extensibility in the extension range up to the extension of 125% is preferably not greater than about 150 g/% extension, more preferably not greater than about 120 g/% extension. The modulus of extensibility at the extension of 135% is not greater than about 200 g/% extension, preferably not greater than about 175 g/% extension, more preferably not greater than about 150 g/% extension. The modulus of extensibility in the extension range up to the extension of 135% is preferably not greater than about 200 g/% extension, more preferably not greater than about 175 g/% extension. The modulus of extensibility at the extension of 150% is preferably not greater than about 300 g/% extension, more preferably not greater than about 250 g/% extension. The force to obtain the extension of 125% is preferably not greater than about 5,000 g, more preferably not greater than about 4,500 g. The force to obtain the extension of 135% is preferably not greater than about 6,000 g, more preferably not greater than about 5,500 g. The force to obtain the extension of 150% is preferably not greater than about 9,000 g, more preferably not greater than about 8,000 g.

Figure 7:
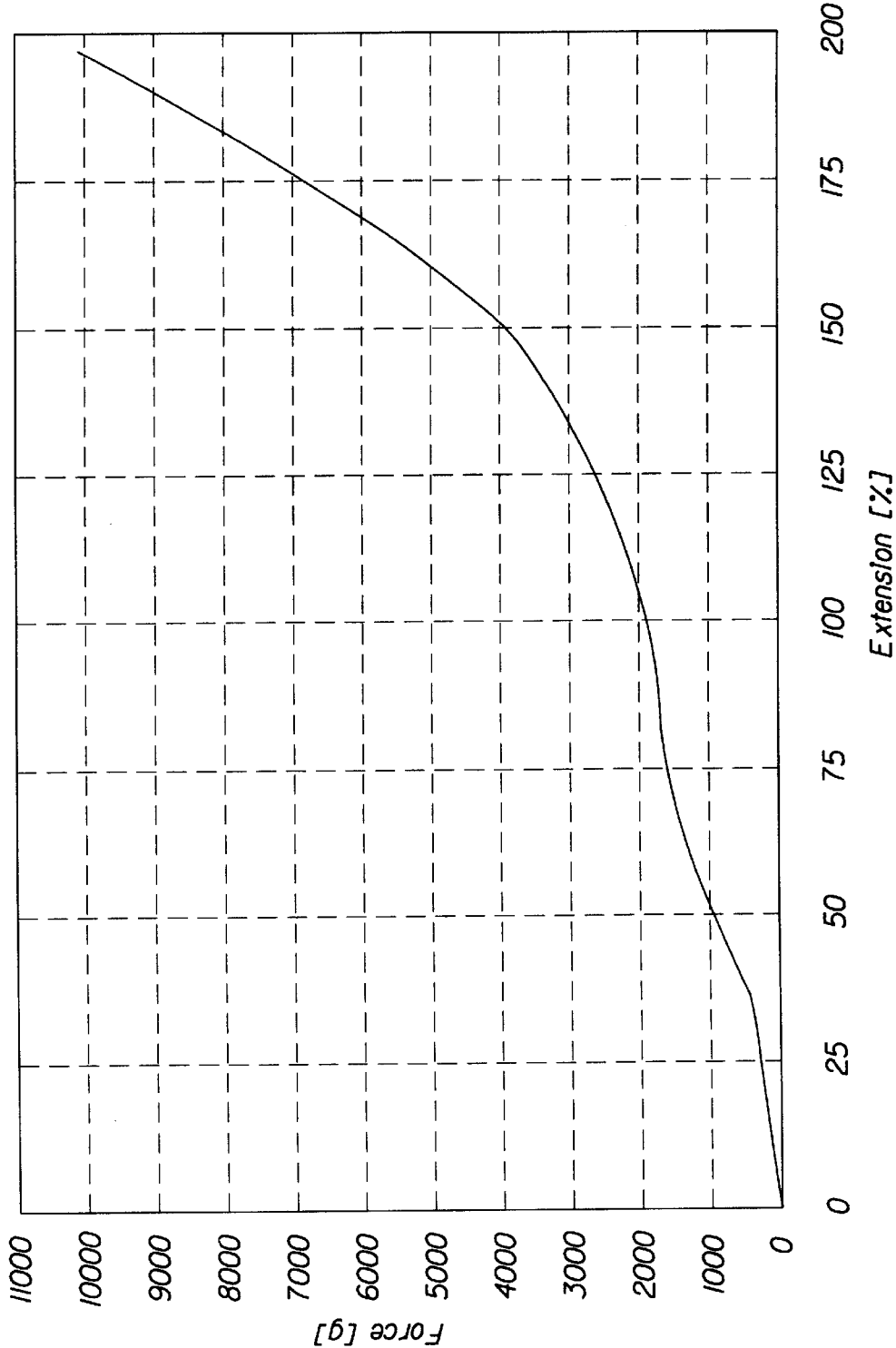
FIG. 7 is a graph of force plotted against percent extension for the continuous belt zone of a garment in accordance with the present invention.
Figure 8:
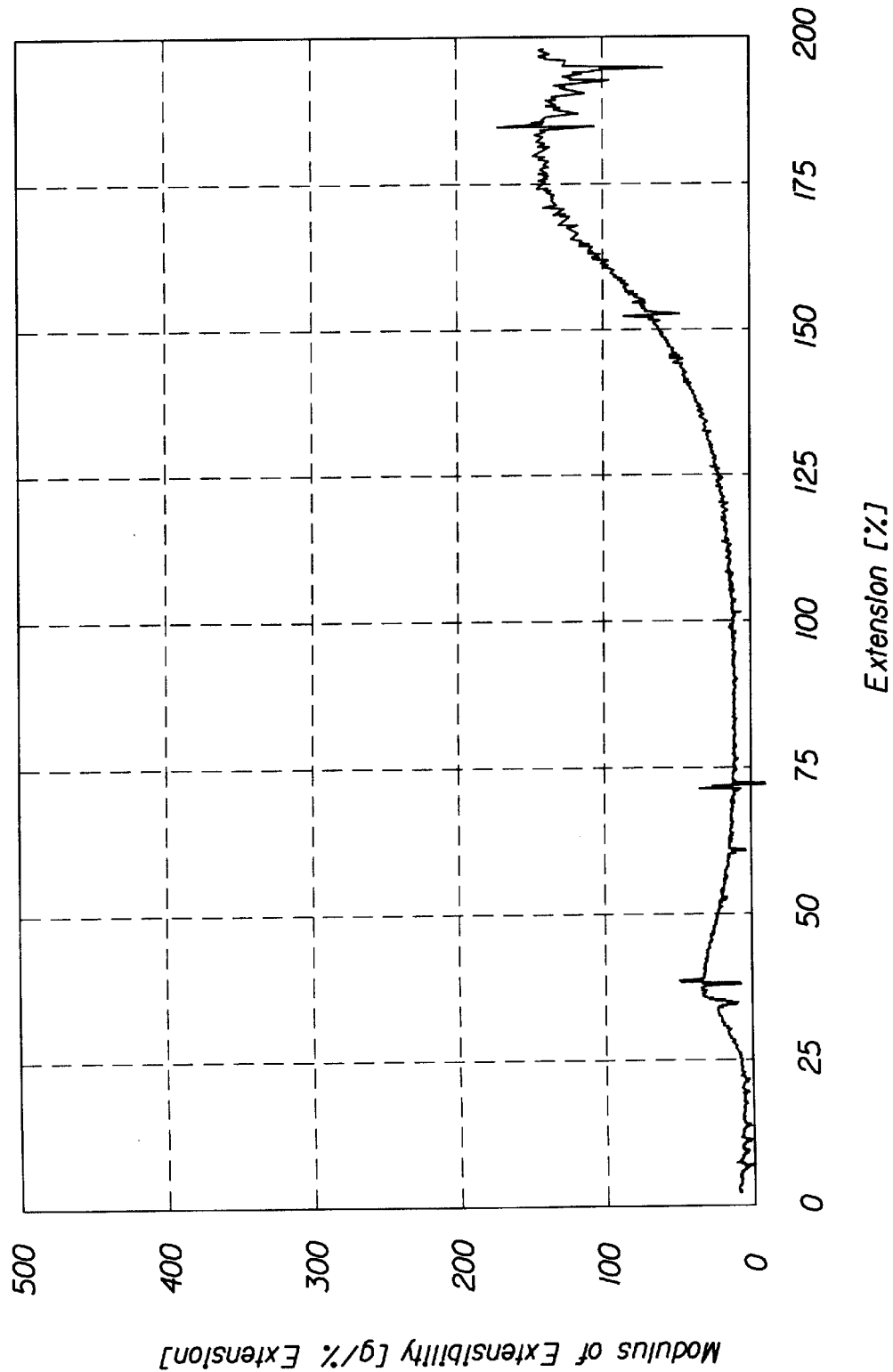
FIG. 8 is a graph of modulus of extensibility plotted against percent extension corresponding with the data shown in FIG. 7.

FIG. 7 shows one preferred example of the force versus extension curves of the continuous belt zone 38 of the pull-on diaper. FIG. 8 shows the modulus of extensibility versus extension curve of the example shown in FIG. 7. The methods to obtain a force versus extension curve of the continuous belt zone 38 and a modulus of extensibility versus extension curve are set forth below.

The methods to obtain a force versus extension curve of the continuous belt zone and a modulus of extensibility versus extension curve are set forth below. This method is a modified ultimate tensile test method contained within the "Sintech TestWorks" software package for measuring a force versus extension curve. This measurement is basically designed to simulate the applicator habit in putting a pull-on diaper on the wearer by using the Instron force tester and two horizontal bars in the place of the jaws starting from 0 g force to 10,000 g force or when the diaper breaks, which represents the ultimate force applied to the continuous belt zone. The method gives "force versus extension" curve from the untensioned condition up to the ultimate tensile of the diaper. The force versus extension data generated as described above can then be converted to "modulus of extensibility versus extension."

This test method requires sample preparation as described below.
(1) The sample diaper to be tested should be taken from the bag
(2) Measure the diaper inside circumference at the waist edge of the diaper using measuring tape without stretching diaper during the measurement (Untensioned Diaper Circumference)

This test method involves the following equipment below.

| | |
|---|---|
| (1) Tensile/Cycle Tester | Instron Model 5564 |
| (2) Operation Software | Sintech TestWorks version 3.0 |
| (3) Loadcell | Instron Static Loadcell 100N |
| (4) Jaw | 20 mm diameter × 150 mm length Teflon coated bar mounted horizontally to upper and lower jaws |

This test method is performed with the setting below.

(1) Test Method: Tensile
(2) Travel Speed: 20 inch/minute
(3) Gauge Length: distance of the center of the upper bar and the lower bar is calculated as below (Gauge Length)=(Untensioned Diaper Circumference)/2−30 mm (4) # of Cycle: 1 cycle
(5) Break Sensitivity: 75%
(6) Load Limit: 10,000 g
(7) Calculation Input: Untensioned Diaper Circumference, Load Point at 500 g, 1,000 g, 2,000 g, 3,000 g, 4,000 g, 5,000 g, 6,000 g
(8) Calculation Results Diaper Circumference at 0 g (=untensioned), extension at load point at 500 g, at 1,000 g, at 2,000 g, at 3,000 g, at 4,000 g, at 5,000 g, at 6,000 g, at peak load, Load at Peak, circumference at peak load Diaper circumference at certain load point is calculated as below (Diaper Circumference)=(Untensioned Diaper Circumference)+(extension)×2

Extension at certain load point is calculated as below.

(Extension)=(Extended Diaper Circumference−Untensioned Diaper Circumference)/(Untensioned Diaper Circumference)

The test method is executed as below.
(1) Prepare sample diapers and measurement data
(2) Set up the Instron Loadcell and Jog following the Instron Setting above then calibrate the Loadcell
(3) Log in to the TestWorks system
(4) Choose tensile test method from the method list tool bar, then let Control Panel, Load Meter, Extension Meter, and Handset show up on the screen
(5) Enter the Untensioned Diaper Circumference data into gauge length in the calculation input
(6) Set up the Gauge Length using a ruler following the Gauge Length Setting described above (Example: Untensioned Diaper Circumference=380 mm→Gauge Length=380/2−30=160 mm)

(7) Reset the Load in the Load Meter and Extension in the Extension Meter
(8) Measure the product weight by putting a product to be test on the upper bar then reset the load again
(9) Put the sample diaper on the Jog with checking the cuff/leg elastic does not stick on the bar
(10) After putting the diaper on the jog, do not reset the Load Meter
(11) Click the "Run" to start the measurement
(12) When the measurement has been done, the jog returns to the original position
(13) Click "File" to save the data and remove the diaper
(14) Repeat the step 6–13 for other sample
The data are evaluated as follows:
(1) After completion for all samples, export the data into an appropriate spreadsheet program (i.e. Microsoft Excel)
(2) "Force versus extension curve" is obtained by plotting the force in grams against diaper extension in percent
(3) "Modulus of extensibility" is obtained by dividing the force difference between two successive data points by the extension difference between the two same points
(4) "Modulus of extensibility versus extension curve" is obtained by plotting the modulus of extensibility obtained in the step of (3) against diaper extension in percent As stated above, the continuous belt zone 38 creates fit force in the pull-on diaper 20 when positioned on the wearer, to maintain the pull-on diaper 20 on the wearer. The continuous belt zone 38 further includes a zone of extensibility that comprises elastic materials such as the side elastomeric material 124 and the waist elastomeric material 200. The zone of extensibility can further include a leg elastomeric material. The leg elastomeric material comprises elastomeric material such as the elastic strands 64 as shown in FIG. 3. The leg elastomeric material can comprise the material used for the side elastomeric material 124 or the waist elastomeric material 200. Herein "zone of extensibility" refers to a continuous area or a continuous zone of the pull-on diaper rendered extensible by an elastomeric material having the form of a continuous plane layer with or without apertures, or the form of strands that are not connected to each other. The zone of extensibility is that portion in the continuous belt zone 38 which substantially generates the skin contact pressure in the continuous belt zone 38. The skin contact pressure generated by the zone of extensibility contributes to maintaining the pull-on diaper on the wearer (sustained fit of the pull-on diaper). The skin contact pressure in the zone of extensibility can not be uniform everywhere. For example, the skin contact pressure of the zone of extensibility between about the waist opening and about the leg openings can be different from each other. Additionally, the skin contact pressure can vary around the radial circumference of the diaper or the leg circumference of the diaper.

In the zone of extensibility, the elastic component of the elastomeric material (such as a plurality of first strands 125 and a plurality of second strands 127 of the elastomeric scrim 124 shown in FIG. 6) pressing on the skin usually generates higher skin contact pressure than the remainder of the area of the zone of extensibility (such as a plurality of apertures 132 of the elastomeric scrim shown in FIG. 6). Therefore, lower skin contact pressure of the elastomeric material pressing on the skin leads to a reduction of the local skin incidence.

The skin contact pressure of the elastomeric material (either the side elastomeric material and/or the waist elastomeric material) pressing on the skin should be not less than about 0.1 psi in order to maintain the pull-on diaper 20 on the wearer, preferably not less than about 0.2 psi, more preferably not less than about 0.3 psi. The skin contact pressure of the elastomeric material (either the side elastomeric material and/or the waist elastomeric material) pressing on the skin should be not greater than about 0.75 psi in order not to cause skin marking in the zone of extensibility, preferably not greater than about 0.65 psi, more preferably not greater than about 0.55 psi. Any combination selected from the above ranges of the skin contact pressure of the elastomeric material pressing on the skin is effective in providing a pull-on diaper with a reduced risk of drooping, sagging or sliding down from the position on the wearer, with a reduced risk of skin incidence in the zone of extensibility, and with a reduced risk of skin incidence by the elastomeric material. The skin contact pressure of the elastomeric material (leg elastomeric material) pressing on the skin should be not less than about 0.1 psi to maintain the pull-on diaper 20 on the wearer, preferably not less than about 0.2 psi, more preferably not less than about 0.3 psi. The skin contact pressure of the elastomeric material (leg elastomeric material) pressing on the skin should be not greater than about 0.75 psi not to cause the skin incidence in the zone of extensibility, preferably not greater than about 0.65 psi, more preferably not greater than about 0.55 psi. The method to obtain the skin contact pressure of the elastomeric material pressing on the skin is set forth below.

The skin contact pressure of the elastomeric material pressing on the skin within the zone of extensibility about the waist opening can be higher than the skin contact pressure of the elastomeric material pressing on the skin at the remainder of the area within the zone of the extensibility to provide a sustained fit of the pull-on diaper about the waist opening. The skin contact pressure of the elastomeric materiel pressing on the skin within the zone of extensibility about the leg openings can be higher than the skin contact pressure of the elastomeric material pressing on the skin at the remainder of the area of the zone of the extensibility to provide a sustained fit of the pull-on diaper about the leg openings. The skin contact pressure of the elastomeric material pressing on the skin about the waist opening and about the leg openings within the zone of extensibility can be higher than the skin contact pressure of the elastomeric material pressing on the skin at the remainder of the area within the zone of the extensibility. The difference between the highest skin contact pressure of the elastomeric material pressing on the skin within the zone of extensibility and the lowest skin contact pressure of the elastomeric material pressing on the skin should be less than about 0.65 psi, preferably less than about 0.45 psi, more preferably less than about 0.25 psi. As the difference becomes closer to zero, the skin contact pressure of the elastomeric material pressing on the skin within the zone of extensibility becomes closer to uniform everywhere. This further contributes to reduce a skin incidence which have caused by the different pressure.

The pull-on diaper 20 further comprises additional elastomeric material such as the spacing means 58 of the inner barrier cuff 54. It is preferable that these additional elastomeric materials incorporated in the pull-on diaper 20 gives skin contact pressure of the additional elastomeric material pressing on the skin of the wearer of not greater than about 0.75 psi. Preferably, the skin contact pressure of the additional elastomeric material pressing on the skin of the wearer is not greater than about 0.65 psi, more preferably not greater than about 0.55 psi.

The method to measure the skin contact pressure of the elastomeric material pressing on the skin within the zone of extensibility is set forth below. The method entitled "AMI Air-pack Type Contact Surface Pressure Measurement System" is commercially supplied by AMI Co., Ltd. to measure the surface contacting pressure generated between soft materials. This method is modified to measure the contacting pressure between the diaper and wearer's body. Air pressure indicated represents the force of contact surface from which the force absorbed by ductility of the material has been deducted. The sensing part is composed of an air pack made of a very soft thin film, of a tube introducing to the main unit and the measured value is converted into DC output (10 mV=1 gf/cm$^2$).

This test method requires sample preparation below.
(1) The sample diaper to be tested should be taken from the bag
(2) Measure the width of the actual elastomeric component of the elastomeric material (i.e. elastic strands) under the 50% stretched condition and calculate the percent area of the elastomeric component This test method entitled "AMI Air-pack Type Contact Surface Pressure Measurement System" involves the following equipment below.

| | |
|---|---|
| (1) Air-pack | AMI Co., Ltd. Model Ø15 mm |
| (2) Main Unit | AMI Co., Ltd. AMI 3037-2 |
| (3) Option Unit | AMI Co., Ltd. AMI 3037-2B |
| (4) Air Cylinder | AMI Co., Ltd. |
| (5) Calibration Set | AMI Co., Ltd. |
| (6) Data Collector | ANRITSU METER Co., Ltd. AM-7052 |
| (7) Data Converting Software | ANRITSU METER Co., Ltd. DATA COLLECTOR System AMS7006WIN ver. 2.0 for Windows |

Figure 9:
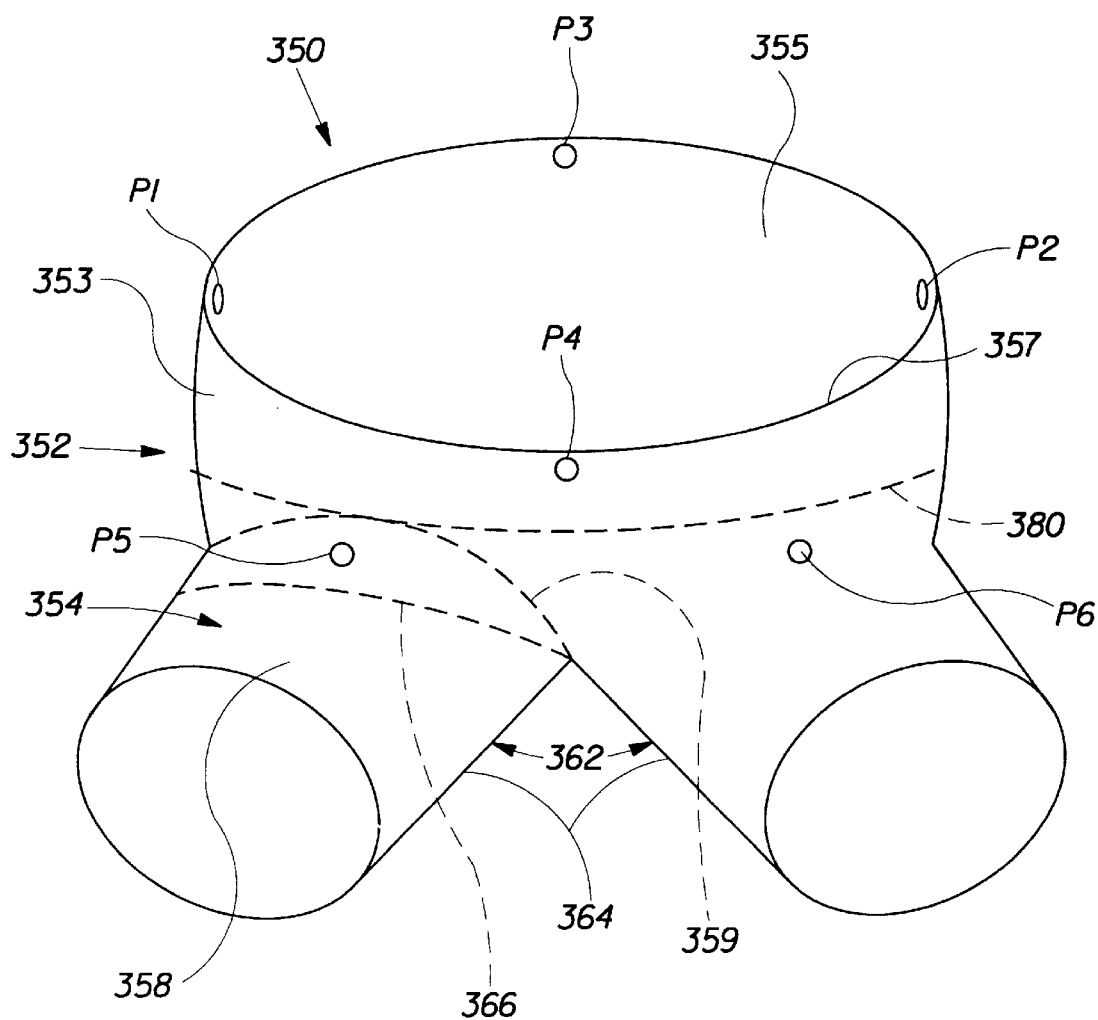
FIG. 9 is a perspective view of a standard mannequin used to measure skin contact pressure.
Figure 10:
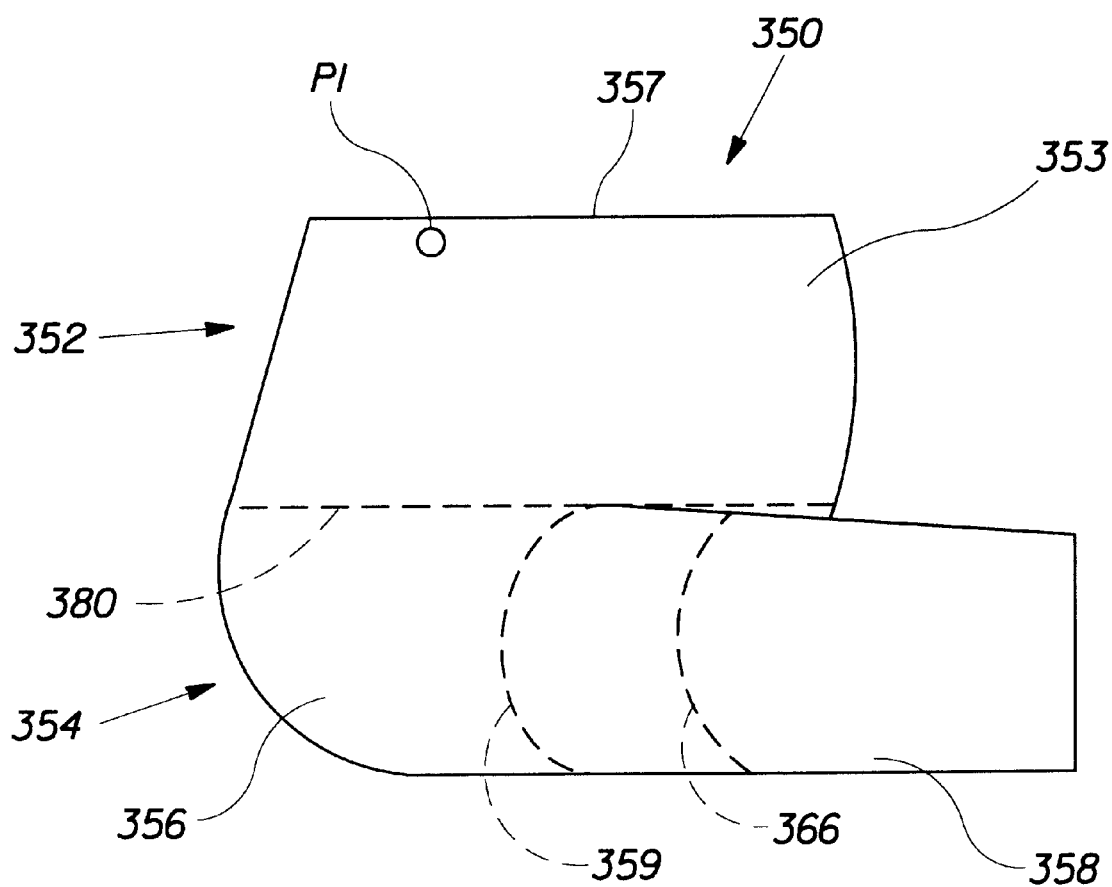
FIG. 10 is a side view of the standard mannequin shown in FIG. 9.
Figure 11:
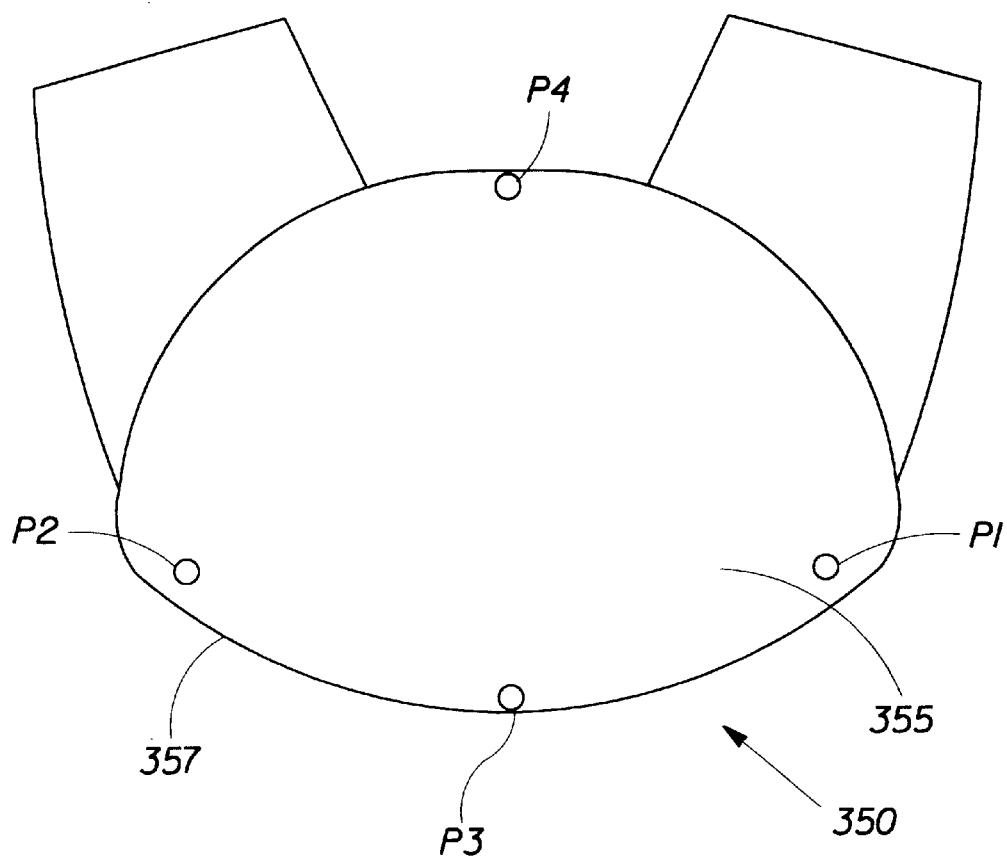
FIG. 11 is a top view of the standard mannequin shown in FIG. 9.

This test equipment described above requires the setting below.
(1) Connect the output cable to the output connector of the main unit and connect the opposite side of the output cable to the data collector
(2) Turn on the power
(3) Use the gear, push the head of air cylinder to the end in the shortest length
(4) Connect the air pack to the air cylinder
(5) Insert the pin into the blue head on the gear, turn the gear until the pin comes to the end, wait 3 seconds
(6) Press the release lever for making air cylinder pressure to be the same with and ambient pressure, wait 3 seconds
(7) Insert the pin into the hole of the gear whose color is the same with the air pack, turn the gear until the pin comes to the end
(8) Remove the air pack from the air cylinder, turn the gear until the pin comes to the end
(9) Check if the output signal from the main unit is close to zero with allowance of 5 mV (0.5 gf/cm$^2$)
(10) Connect the air pack to the main unit (connection should be made in one action. If you renew connection, inside volume of air pack must be changed)
(11) Press the air pack by hand flat or finger for removing all the air from the air pack, check the output signal transmitted from the main unit, be careful that this is the maximum measurement value and that the system can not measure any values exceeding the maximum measurement value. If the contact surface is bent too much, and if output signal from the main unit exceeds +20 mV (2 gf/cm$^2$), connect the air cylinder and press the release lever
(12) Prepare at least 2 air-packs for standard measurement This method utilizes a standard mannequin 350 having the form shown in FIGS. 9 and 10 and is modeled after the body shape in a sitting posture of a wearer. The shape and the dimension of the standard mannequin 350 should be based on the body dimension data taken from the actual diaper users. The standard mannequin 350 has an upper portion 352 and a lower portion 354. The upper portion 352 and the lower portion 354 are divided by the lower torso line 380. The lower torso line 380 is the circumferential line through the upper portion of the pubic bone. The upper portion 352 includes a torso portion 353. The torso portion 353 has an upper surface 355 (shown in FIG. 11) surrounded by the waist line 357 which is the circumference line about the top waist of the torso portion 353. The torso portion 353 has a height defined by the height between the waist line 357 and the lower torso line 380. The circumference of the torso portion 353 gradually increases from the waistline 357 toward the lower torso line 380. The lower portion 354 includes a hip portion 356 at the back of the lower portion 354, and the leg portions 358 protruding from the hip portion 356 at the front of the lower portion 354. The hip portion 356 and the leg portions 358 are divided by the crotch crease line 359 along the fat fold at the front of the body. The two leg portions 358 have a crotch angle 362 that is the angle subtended between the inner thighs 364. The leg portion 358 has a thigh line 366 that is the circumferential line about the thigh of the leg portion 358. The upper surface 355 has a shape surrounded by the waistline 357 that comprises straight lines and curve lines. FIG. 11 shows one preferred example of the shape of the upper surface 355, which is determined, based on the actual wearer dimension. The standard mannequin is made of vinyl chloride.

The actual dimension of the standard mannequin for a diaper designed to fit the wearer weighing from about 7.0 kg to about 10.0 kg is shown below.

| | |
|---|---|
| Circumference at the waistline: | 460 mm |
| Circumference at the lower torso line: | 470 mm |
| Circumference at the crotch crease line: | 310 mm |
| Circumference at the thigh line: | 275 mm |
| Height of the torso: | 75 mm |
| Crotch angle: | about 60 degrees |

The actual dimension of the standard mannequin for a diaper designed to fit the wearer weighing from about 9.0 kg to about 14.0 kg is shown below.

| | |
|---|---|
| Circumference at the waistline: | 495 mm |
| Circumference at the lower torso line: | 505 mm |
| Circumference at the crotch crease line: | 330 mm |
| Circumference at the thigh line: | 290 mm |
| Height of the torso: | 80 mm |
| Crotch angle: | about 60 degrees |

The actual dimension of the standard mannequin for a diaper designed to fit the wearer weighing from about 13.0 kg or above is shown below.

| | |
|---|---|
| Circumference at the waistline: | 520 mm |
| Circumference at the lower torso line: | 530 mm |
| Circumference at the crotch crease line: | 350 mm |
| Circumference at the thigh line: | 305 mm |
| Height of the torso: | 85 mm |
| Crotch angle: | about 60 degrees |

The measurement points for the waist elastomeric material and the side elastomeric material are determined as below.

Point P1 is the point of the minimum radius of the waist curvature line at the right side of the torso portion. Point P2 is the point of the minimum radius of the waist curvature line at the left side of the torso portion. Point P3 is the point at the center of the back of the torso portion. Point P4 is the point at the center of the front of the torso portion. The measurement points P1, P2, P3, and P4 should be mounted about 10 mm below the waistline and should be fully covered by the waist material of the sample diaper. Point P5 is the point at the front of the right leg portion and point P6 is the point at the front of the left leg portion. The Air-packs for the measurement point P5 and P6 should be mounted right under the elastomeric material contacting the mannequin's leg portion.

The measurement points for the leg elastomeric material are the points where the elastomeric material presses on the skin of the standard mannequin.

This method is executed as below.
(1) Set up the pressure measurement system following the setting above (2) Prepare sample diapers and mount the diaper on the standard mannequin
(3) Place two Air-packs at the point P1 and P2 and measure the pressure
(4) Record the pressure measurement data and check if the pressure signal recovers close to zero with allowance of 5 mV (0.5 gf/cm$^2$)
(5) Place two Air-packs at the point P3 and P4 and measure the pressure
(6) Record the pressure measurement data and check if the pressure signal recovers close to zero with allowance of 5 mV (0.5 gf/cm$^2$)
(7) Place two Air-packs at the point P5 and P6 and measure the pressure
(8) Record the pressure measurement data and check if the pressure signal recovers close to zero with allowance of 5 mV (0.5 gf/cm$^2$)
(9) Repeat the step 2 to 8 for 1 sample diaper
The data are evaluated as below.
(1) "Local average skin contact pressure within the zone of extensibility" is obtained by converting the measured voltage into psi (10 mV=1 gm/cm$^2$)
(2) "Skin contact pressure of the elastomeric material pressing on the skin" is then obtained in psi by dividing the "local average skin contact pressure within the zone of extensibility" obtained above by the percent area of the elastomeric component.

The materials employed in making presently-commercially-available disposable diapers, pull-on diapers, and similar disposable absorbent articles, generally have a coefficient of static friction on their skin-facing surfaces of from about 0.15 to about 0.23. Coefficient of static friction values at those relatively low levels facilitate application of the diaper to the body of the wearer, but they also dictate relatively high skin contact pressures between the diaper inner surface and the body of the wearer, of the order of about 1 psi. That level of skin contact pressure is particularly advantageous in the waistband area, to maintain the diaper in its preferred wearing position for optimum effectiveness. It is those relatively higher skin-contact pressures that lead to red marking of the skin of the wearer. Such skin red-marking can be both pressure-induced marking as well as abrasion-induced marking, the latter occurring when surfaces of the diaper move relative to the skin of the wearer as the wearer moves his or her body.

In accordance with the present invention, reduction of the contact pressure of a disposable diaper against the skin of a wearer provides increased wearer comfort. Additionally, reduction of the diaper-to-skin contact pressure also reduces pressure-induced and abrasion-induced red marking of the skin of the wearer. However, excessive reduction of the skin contact pressure of the diaper, particularly in the waistband area of the diaper, can result in slippage of the diaper on the wearer's body, with resultant undesirable drooping-or sagging of the diaper. It has been found that such undesirable consequences of contact pressure reduction can be overcome by increasing the coefficient of static friction at selected areas within the interior of the diaper. By "interior" is meant the surface of the diaper that contacts the skin of the wearer.

An increase in the coefficient of static friction of the skin-facing surface of a disposable diaper can be selectively provided at strategic areas on interior, skin-facing surfaces of the diaper with beneficial results. Referring to FIGS. 1 and 3, pull-on diaper 20 includes a pair of retention zones 400, 402 (only one of which is visible in FIG. 1), one on each side of the diaper, within the interior of the waistband area and at positions that substantially overlie the hipbone of the wearer when the diaper is worn. Retention zones 400, 402 can be provided by a material that has a higher coefficient of static friction than does the body-facing surface of topsheet 24, or the body-facing surface of front extensible ear 46, or the body-facing surface of back extensible ear 48, diaper inner surfaces that together define the major portion of the interior, body-facing surfaces of the diaper.

Positioning the retention zones at substantially the hip-contacting areas of the inner surfaces of waistband 57, 59 minimizes the skin abrasion effect of slippage forces that come into play when the wearer of the garment moves his body. In that regard, at the hip-contacting areas of the diaper there is less relative movement between the diaper inner surface and the skin of the wearer, as compared with some other areas of the diaper, such as the stomach-contacting area, for example, where significant relative movement between the diaper and the wearer can occur. Additionally, because the hip-contacting surfaces of the diaper are generally the surfaces that are gripped and spread apart to enlarge the circumference of the waistband during application of the diaper, positioning the retention zones at those areas serves to minimize the contact of the retention zones with the skin of the wearer as the garment is being applied to the body of the wearer. Thus, the higher-friction, hip-contacting surfaces of the diaper are held away from the wearer's body during application of the diaper, and consequently a higher coefficient of static friction in those areas does not operate to impede application of the diaper.

In addition to the hip-contacting surfaces of the diaper, other interior, skin-facing surfaces of the diaper that can have a locally higher coefficient of static friction can include the back-contacting area of waistband 59. A higher coefficient of static friction on that surface further improves the position-retention characteristics of the diaper, and thereby further minimizes the likelihood of downward slippage of the diaper when in use. As shown in FIG. 3, such a back retention zone 404 can be provided on the inner surface of waistband 59 as an elongated rectangular strip of a high coefficient of friction material. Alternatively, retention zone 404 can also be defined by a series of narrow, spaced, substantially parallel strips, or by a series of spaced spots positioned along the inner surface of waistband 59 of the diaper. Advantageously, such a back retention zone 404 can be employed in addition to hip-contacting retention zones 400, 402, if desired. However, the sizes and positioning of other higher coefficient of static friction surfaces within the interior of the diaper, and at points spaced from the hip-contacting surfaces, must be carefully selected so that those non-hip-contacting surfaces do not unduly impede application of the diaper.

Hip-contact-area retention zones 400, 402 preferably have as small an area as possible, consistent with their diaper position retention purpose, to reduce the overall cost of the garment while still providing the benefits of the present invention. In that regard, hip-area retention zones 400, 402 can each have an aggregate area of from about 0.01 in$^2$ to about 16 in$^2$ per side, preferably from about 0.25 in$^2$ to about 10 in$^2$ per side, and most preferably from about 1 in$^2$ to about 3.5 in$^2$ per side. And in addition to hip-contacting retention zones that are unitary, continuous areas having a relatively high coefficient of static friction, such as the generally rectangular form of retention zones 400, 402 as shown in FIG. 1, the respective retention zones can alternatively be provided in the form of several thin, substantially parallel strips (see FIG. 20), or in the form of closely spaced spots that can be of any convenient geometric form, such as circles, rectangles, ovals, and the like, with intervening areas that do not exhibit a higher coefficient of static friction.

When provided in the form of spaced spots, the total area over which the spots can be provided, whether in the hip-contacting areas or in the waist-contacting areas, is preferably about 3.5 in$^2$ per side for the hip-contact areas, and preferably about 3.5 in$^2$ per waist-contact area, but the aggregate areas of the individual high coefficient of static friction spots should preferably be within the ranges specified above. As a further alternative, retention zones 400, 402 can be in the form of one or more thin, elongated areas that have their major axes substantially parallel with the transverse centerline of the diaper, or they can be one or more thin, elongated areas that have their major axes substantially parallel with the longitudinal centerline of the diaper.

Suitable ways of providing retention zones that can be employed to provide the desired increased coefficient of friction can include coatings or patches of relatively high coefficient of static friction materials. Coatings can include, but are not limited to, coatings of pressure-sensitive materials or of tacky materials. Patches can be in the form of thin films, or the like, that are adhered to or otherwise connected with the interior surface of the waistband in either or both the hip-contacting area and the rear waist area of the garment. Examples of suitable coating materials are polymeric materials, such as hot melt resealable adhesives that are flexible when cooled; rubber-based materials, including solid rubber and rubber-based foams; and any latex or hot melt material that has sufficient frictional properties to hold a diaper in position on the body of a wearer during use. More specifically, coatings made from the following materials are suitable:

- ethylene vinyl acetate copolymers—could be applied as a hot melt or as a water based coating—the best candidates have at least 28% vinyl acetate;
- polyvinyl acetate—normally used in water-based emulsions;
- styrene-butadiene—applied in an emulsion or as a hot melt;
- cellulose acetate butyrate—normally hot melt coatings;
- ethyl cellulose—normally blended with a plasticizer and a resin and applied as a hot melt;
- acrylics-normally emulsion systems that are not blended;
- synthetic rubber hot melt-Kraton® block copolymers having elastomeric and styrenic blocks, rubber, resin, and plasticizer blends; and
- other hot melts-polyethylenes (alone or blended), polyamides, and the like.

Typical suitable coating compositions are the ethylene-vinyl acetate copolymers, acrylic terpolymers of methacrylic acids, acrylic copolymers, ethylene-vinyl acetate/resin latex emulsions, ethylene-vinyl acetate hot-melt adhesives, synthetic rubber (block copolymers with elastomeric and styrenic components) hot melt adhesives, and polyvinyl acetate/resin emulsions. Such materials are available from H. B. Fuller Company, E. I. DuPont, and Findley Adhesives, among others, and have been used as hot-melt and water-based coatings for barrier coatings for nonwovens and/or papers. Those skilled in the art will appreciate that other coating materials are also available for locally raising the coefficient of static friction on interior surfaces of disposable diapers.

When applied as a coating, the materials are preferably applied in such a manner as to provide a coating of substantially uniform thickness, overlying the innermost, skin-facing surface of a portion of the diaper waistband, and having an area of the magnitude identified above. Additionally, from the standpoint of additional comfort to the wearer, the coatings employed to provide the retention zone of the present invention preferably are breathable or are made to be porous, such as by providing a plurality of small, spaced apertures throughout the coated retention zone.

High coefficient of static friction coating materials can be applied using a number of methods that are known to those skilled in the art. Methods for coating include, but are not limited to, extrusion coating, slot coating, gravure printing, and screen printing. Additionally, known application methods can be employed to deposit in desired areas materials in loose fiber form that exhibit high coefficient of static friction properties. Examples of suitable materials include a melt-blown or spunbond application of fibers of any of the fibrous polymeric materials previously identified.

Coatings can be applied either at the raw material supplier's facility (i.e., the supplier of the nonwoven material contained within the diaper waistband or side panels) or they can be applied on-line during manufacture of the diaper.

Coatings can also be applied either before or after activation of the elastic laminate material forming part of the waistband or the side panel structure.

Retention zones 400, 402 can be provided in the form of patches that are separately formed and thereafter suitably secured to the interior waistband or side panels of the diaper. When applied as patches, the retention zones can be made from a number of different materials that are thin, flexible, and that can be adhered or otherwise firmly attached to the innermost, skin-facing surface of the diaper waistband or side panels. Examples of materials from which such patches can be made are polymeric films, such as polyvinylidene chloride, apertured polymeric films, fibrous nonwoven sheets, scrims, scrim nettings, or fibrous flocked substrates, either with or without the addition of surface-based tackifier materials for enhancing the coefficient of static friction of the underlying base material. The patches are preferably porous or breathable, and they can be formed from porous films of the type disclosed in U.S. Pat. No. 3,989,867, entitled "Absorptive Devices Having Porous Backsheet," which issued on Nov. 2, 1976, to Sisson, the disclosure of which is hereby incorporated by reference to the same extent as if fully rewritten.

A patch formed from a nonwoven web can be any rubbery composition containing elastomeric components such as natural rubber and isobutylene, polymerized or blended with other polymers that are provided to control the degradation, melting point and flexibility of the elastomers. The nonwoven web can include microfibers including at least about ten percent (10%) by weight of an A—B—A' block copolymer, where A and A' are each a thermoplastic end block that includes a styrenic moiety, and where B is an elastomeric poly(ethylene-butylene) midblock, and from greater than zero percent (0%) by weight, up to about ninety percent (90%) by weight, of a polyolefin, which, when blended with the A—B—A' block copolymer and subjected to a combination of elevated temperature and elevated pressure conditions, is adapted to be extruded, in blended form, with the A—B—A' block copolymer. The polyolefin material can be selected from the group consisting of polyethylene, polypropylene, polybutene, ethylene copolymers, propylene copolymers, butane copolymers, and blends of at least two of those materials. U.S. Pat. Nos. 4,663,220, 4,692,371, 4,741,949, 4,789,699, and 4,803,117 describe extrudable compositions and methods of forming such compositions, especially elastomeric nonwoven webs, and the disclosures of those patents are hereby incorporated by reference to the same extent as if fully rewritten.

Further, a patch of nonwoven material can include A—B—A' block copolymers with polybutadiene or poly-acetate midblocks and polystyrene end blocks, polystyrene/ polyethylenebutylene/polystyrene block copolymer resins, and blends of such resins with materials to control their flexibility and degradation. It should be noted that such compositions should be readably extrudable and should be capable of easily being formed into fibrous webs.

In providing the retention zones described herein, the higher coefficient of static friction at those zones of the garment is preferably of the order of at least about 500% greater than the coefficient of friction of the major portion of the body-facing surfaces of the diaper. Included within those body-facing surfaces is topsheet 24 and the major portions of the elastically extensible side panels, such as the body-facing surface of front extensible ear 46 and the body-facing surface of back extensible ear 48, each defining a portion of the interior, skin-facing surface of the diaper. Advantageously, the higher coefficient of static friction at the retention zones can range from greater than about 0.3 to about 4.0, preferably from about 0.4 to about 2.0, and most preferably from about 0.7 to about 1.5. When such retention zones are provided in such a garment, the waistband hoop stress that is necessary to maintain the garment in substantially its initially-applied position on the body of the wearer can be reduced significantly. In that regard, the usual range of pressure of the garment inner surface against the skin of the wearer for maintaining disposable, pull-on absorptive garments in the desired position on the body of the wearer is from about 0.05 psi to about 0.8 psi. At the higher of those pressure levels some wearers, because of their body size relative to the size of the diaper, cari exhibit red markings about the waist area because of the tightness with which the waistband grips the wearer's body.

By providing at the inner, skin-facing areas of the waistband retention zones having a higher coefficient of static friction, the hoop stress of the waistband, and consequently the pressure it exerts against the skin, can be reduced. The higher friction surfaces that are provided permit the diaper to be retained in substantially its initial, as-applied position, without significant red marking, and even though the weight of the diaper may have been increased by the absorption of body waste materials.

The coefficient of static friction values given herein are based on a test procedure that utilizes a Heidon 14DR surface property tester. The testing was carried out at 25° C., 50% relative humidity, and a standard 400 file polish (JIS) steel plate was used as the substrate against which the material whose stapic coefficient of friction was to be tested was placed. The sample material was attached to a 30 mm×30 mm indenter so that it completely covered one of its major surfaces. If the material to be tested was stretchable, the test was conducted with the direction of stretchability arranged perpendicular to the direction of travel of the moving base of the Heidon 14DR tester. A single travel mode was employed with a travel speed of 600 mm/min. Various normal loads were applied and the coefficient of static friction was determined between the sample mounted on the indenter and the standard steel plate using the supplier-furnished analysis program.

An exemplary way in which a patch of material having an increased coefficient of static friction can be achieved is to provide a thermally bonded laminate of two distinct materials. One of the materials can have sufficient body for ease of handling, and the other of which might be more difficult to handle alone but that has a relatively high coefficient of static friction. Such a high coefficient of static friction material can be an elastomeric scrim in the form of an elastic netting material, such as that identified and described earlier herein as elastomeric scrim 124, the structure of which is illustrated in FIG. 6. Elastomeric scrims typically have a relatively high coefficient of static friction, of the order of about 3.0. One such elastomeric scrim material is available from Conwed Plastics Company, of Minneapolis, Minn., and is identified as XO2514. The Conwed elastomeric scrim material is a netting made from a styrene-butadiene-styrene triblock copolymer material. The scrim is in the form of a plurality of spaced, substantially parallel first strands, and a plurality of spaced, substantially parallel second strands, wherein the first and second strands are disposed at substantially right angles to each other. Further, the first strands and the second strands are joined together to define a coherent elastomeric web that includes a plurality of substantially rectangular open areas that are bounded and defined by respective interconnected first and second strands. The Conwed scrim has a thickness of from about 0.5 to about 1.5 mm, an open area of about 80%, a basis weight of about 120 gsm, and conforms with the extensibility properties hereinbefore described for side elastomeric material 124.

The elastomeric scrim is in the form of a thin, very flexible sheet that because of its flexibility is difficult to handle by itself under high-speed production conditions. Accordingly, the elastomeric scrim preferably is joined with a less flexible sheet of base material to provide a patch that is easy to handle, that has the desired elastic properties, and that has on one face thereof the desired high coefficient of static friction. A suitable base material should also be extensible, at least in one direction, so that it can stretch along with the elastomeric scrim with which it is joined, and thereby conform itself with the contour of the body surface about which the patch is adapted to be brought into contact. A suitable nonwoven material for use in the patch laminate is available from Nisseki Corp., of Japan, and is identified by the trade name "MD MIL1FE." The nonwoven MIL1FE material has a basis weight of 20 gsm and is made from polyester (PET) fibers using a spunbond process that provides a highly machine-direction-oriented fibrous web that has an ultimate elongation in the cross-machine direction of greater than 200%.

Figure 15:
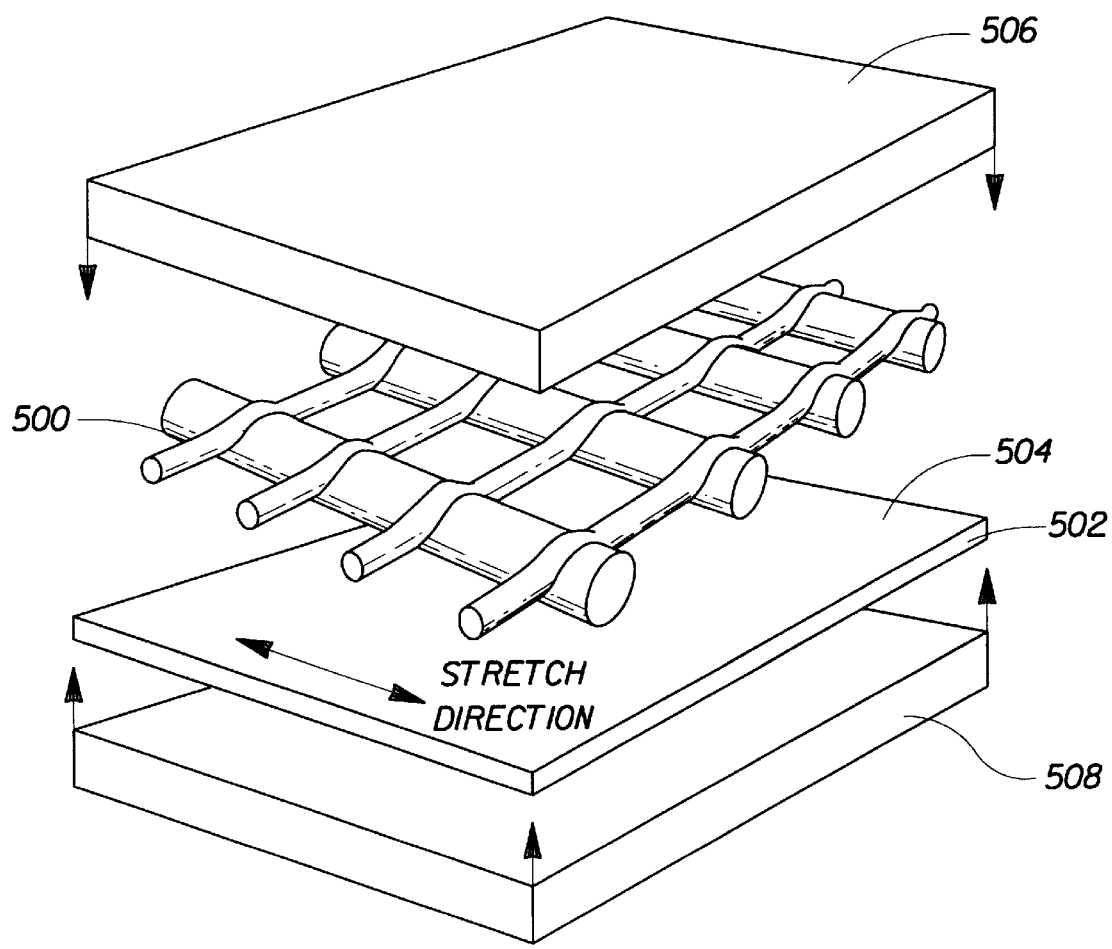
FIG. 15 is an exploded perspective view of materials and apparatus for making a high coefficient of static friction composite.

A high-static-coefficient-of-friction patch can be formed by joining together the scrim and the base nonwoven material by using apparatus such as that shown generally in FIG. 15. A scrim 500 is superposed over the surface of a nonwoven sheet 502, and the scrim and nonwoven are placed between a pair of opposed, flat, heated press plates 506, 508. Scrim 500 is caused to be pressed into and to be bonded to surface 504 of nonwoven sheet 502 by plates 506, 508, until the scrim is permanently attached to and embedded within the surface of the nonwoven.

Figure 16:
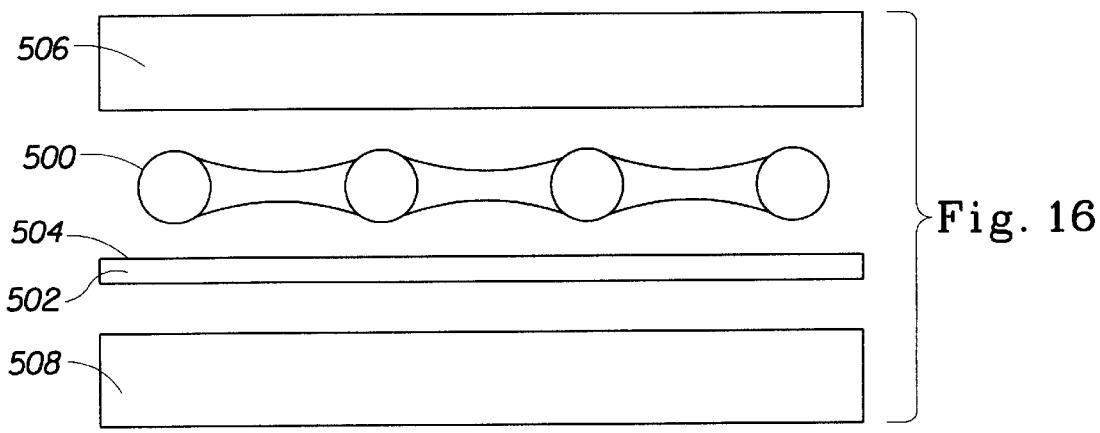
FIG. 16 is a side view of the materials and apparatus of FIG. 15 in position for commencement of a joining operation.
Figure 17:
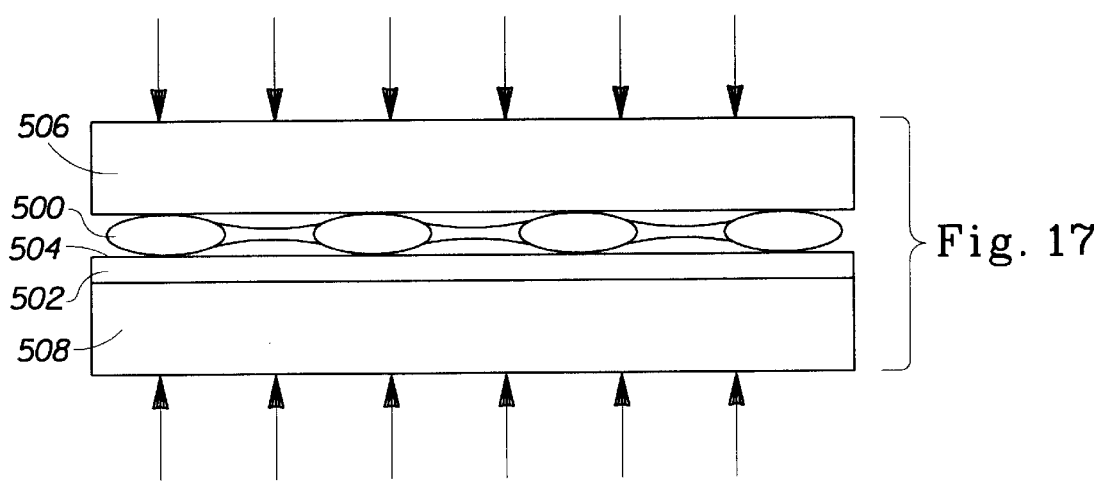
FIG. 17 is a side view of the materials and apparatus of FIG. 15 during the execution of a joining operation.
Figure 18:
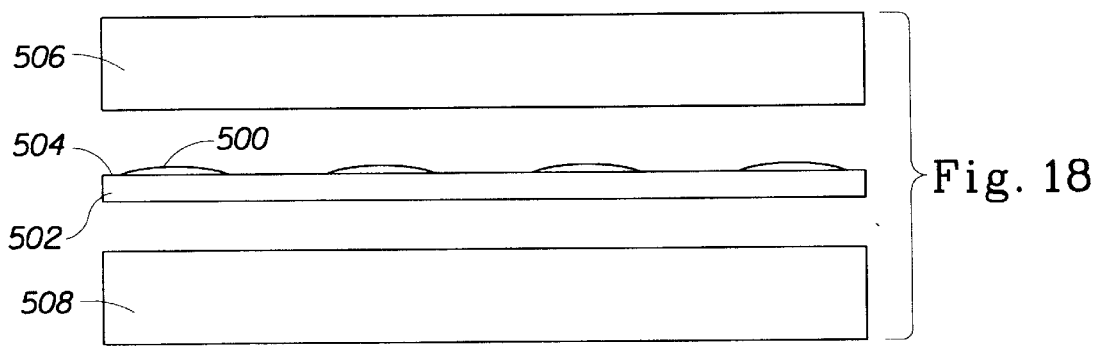
FIG. 18 is a side view of the materials and apparatus of FIG. 15 after the materials have been joined.

The several steps in the lamination process for forming the patch are shown in FIGS. 16 through 18. The opposed, flat surfaces of plates 506, 508 are initially spaced from each other, as shown in FIG. 16, and are heated to a temperature of the order of about 90 to about 100° C., which is sufficiently low so as not to melt the higher-melt-temperature PET fibers of nonwoven 502, but to maintain the fibers of the nonwoven in an intact state, and is sufficiently high to soften scrim 500 sufficiently to become tacky so that it can be pressed into the surface of and to adhere to the nonwoven. Scrim 500 and nonwoven 502 are placed between plates 506, 508 while in superposed relationship to each other.

As shown in FIG. 17, plates 506, 508 are brought toward each other to press scrim 500 and nonwoven 502 into closely contacting relationship. The contact pressure, the plate temperature, and the dwell time are selected to cause the scrim to soften sufficiently to be capable of being pressed into the surface of the nonwoven and to be at least partially embedded therein. Plates 506, 508 are then withdrawn, as shown in FIG. 18, and the laminated scrim and nonwoven composite 510 can be removed and allowed to cool for use. As shown in FIG. 18, one surface of composite 510 includes embedded scrim material, with a portion of the scrim component extending slightly above the surface of the nonwoven component. The coefficient of static friction of the surface of the composite 510 into which the scrim is embedded is from about 2.8 to about 3.0.

Composite 510 can be incorporated into a disposable, pull-on, absorbent pant article as waistband zone 37 shown as a part of disposable pant article 20 illustrated in FIG. 1. The composite imparts to article 20 the increased slip resistance that provides improved performance of the article in terms of greater retention of the article in the preferred wearing position on the body of a wearer.

Figure 19:
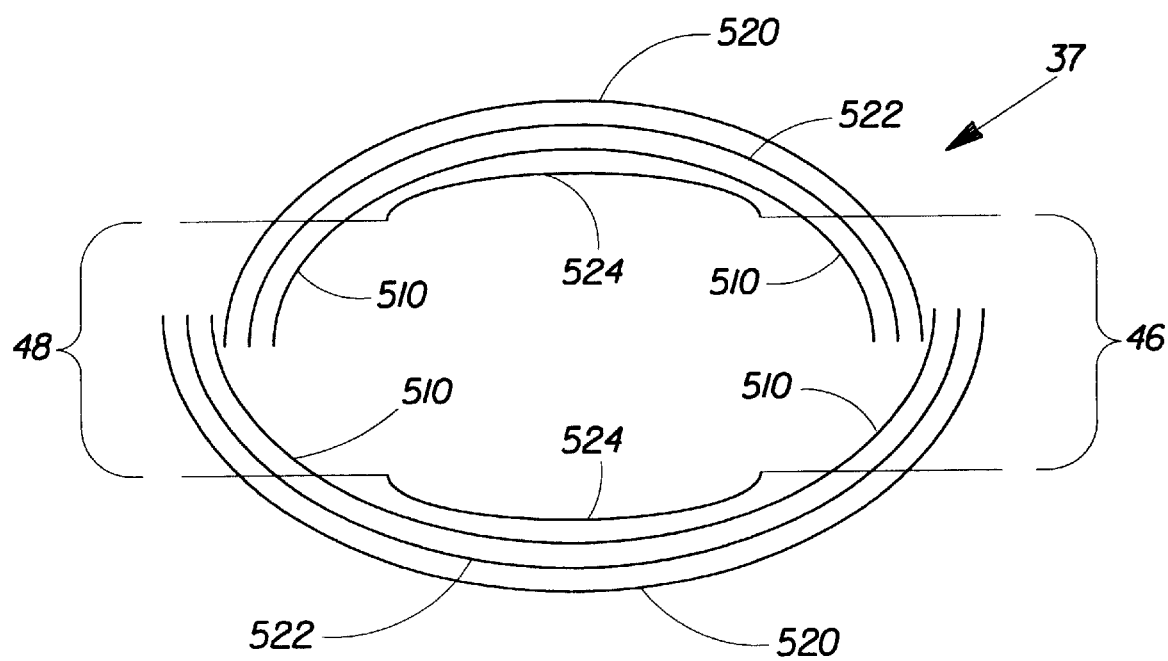
FIG. 19 is a top view of the waistband area of the article shown in FIG. 1 wherein the article includes waistband zones of increased static coefficient for friction.

FIG. 19 is a cross-sectional view taken through waistband zone 37 and shows a preferred structural arrangement thereof. The outermost layer of waistband zone 37 is defined by a backsheet layer 520 of nonwoven material (such as Fiberweb HEC nonwoven). Positioned inwardly of backsheet layer 520 is an intermediate layer 522 of nonwoven material (such as MILIFE nonwoven), and positioned inwardly of intermediate layer 522 is a belt-like layer of composite 510 that has its high-static-coefficient-of-friction surface facing the body of a wearer.

Selected body-facing portions of waistband 37 that contact the stomach and the back of a wearer, and that are positioned above the areas at which absorbent core 25 terminates, can be provided by a material having a relatively low coefficient of static friction. In that regard, rectangular layers 524 of consolidated nonwoven material (such as FiberWeb's DAPP) in strip form can be provided in overlying covering relationship to portions of composite layer 510 at the back and stomach portions of waistband 37. Layers 524 can be adhered to the waistband by suitable adhesives of the type hereinbefore described, in order to permit to be exposed to the skin of the wearer only those portions of waistband 37 that are positioned above the side panels of the article and that overlie the hips of the wearer. As a result, and as shown in FIG. 20, the hip-contacting portions of waistband 37 include composite layer 510 containing an exposed scrim material that has a higher coefficient of static friction to provide the desired resistance to slippage.

Figure 20:
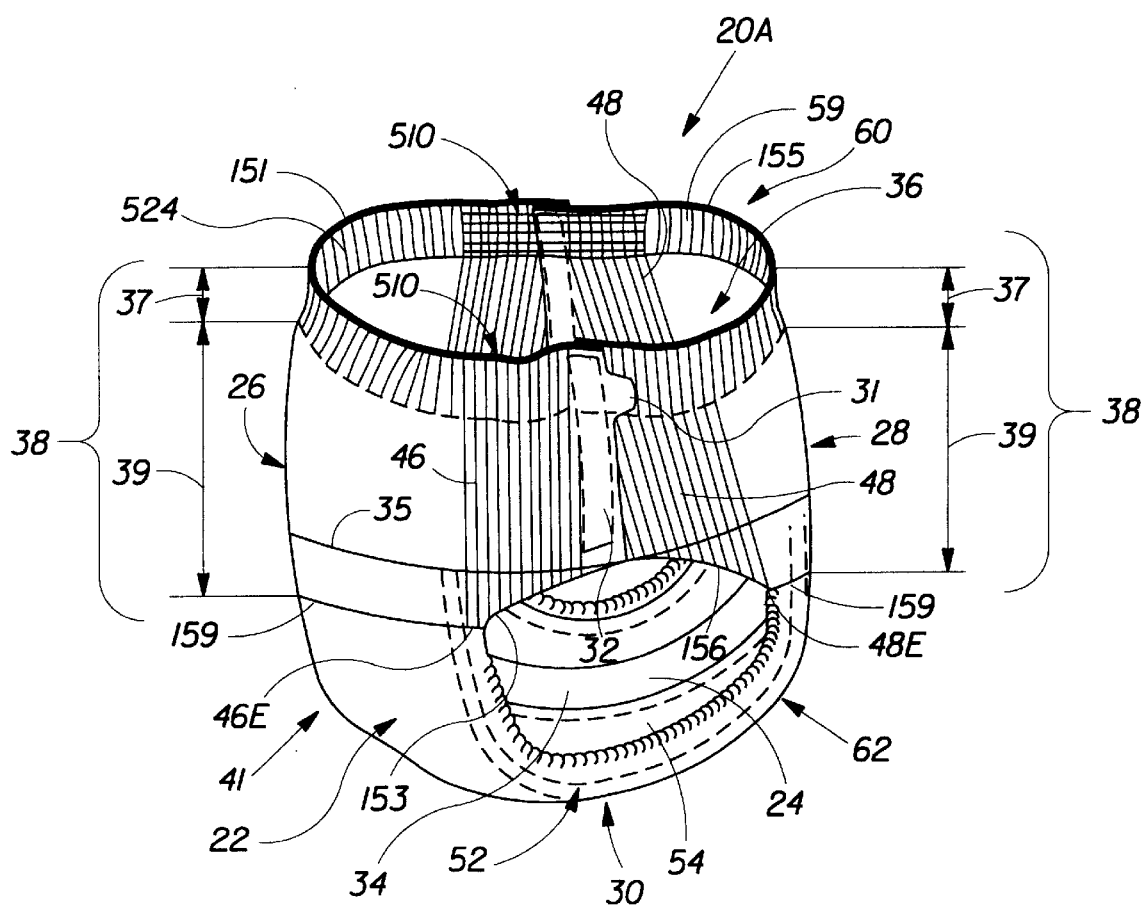
FIG. 20 is a perspective view of an absorbent, pull-on diaper incorporating waistband-positioned retention zones.

Use of the waistband structure shown in FIGS. 19 and 20 enables a reduction of the hoop stress that is normally generated within the waistband when the garment is worn. The increased slip resistance provided by the preferred waistband structure does not require the same degree of tension within the waistband to retain the absorbent article in its desired wearing position for most effective functioning. To provide the benefits of the present invention, the portions of the overall circumference of waistband 37 that include retention zones can be up to about 100%, preferably from about 10% to about 60% and most preferably from about 25% to about 35%, preferably at each hip-contacting portion of waistband 37. The foregoing percentages are for a waistband when it is in its relaxed, unextended condition before the garment is applied to the wearer.

If desired, in addition to or instead of providing retention zones in the waistband zone of a disposable absorbent article to improve article retention when worn, the ears or side panels of the structure can be provided with retention zones to provide increased resistance to slippage of the garment. In that connection, the same high coefficient of static friction laminate described above in the context of it use in the waistband zone of the garment can be employed to form at least a portion of the area of the ear or side panel elements. For, example, and referring to FIG. 20, the interior, skin-facing surfaces of ears 46, 48 on each side of the diaper illustrated can include one or more areas that are defined by a high-static-coefficient-of-friction composite 510 having the structure hereinbefore described. The larger skin contact area of those elements of the diaper structure provide larger-area retention zones, to assist in maintaining the diaper in its preferred wearing position and in reducing the tendency for the diaper to slip downwardly relative to the body of the wearer. In that regard, the aggregate skin contact area of such retention zones on ears 46, 48 on both sides of the diaper can be up to about 13 in$^2$, preferably from about 3.5 in$^2$ to about 11 in$^2$, and most preferably from about 5 in to about 6.5 in$^2$.

Because of the potentially greater skin contact area at the ears of the diaper, as compared with that at the waistband area, it is possible to use in the ear panels materials having a somewhat lower coefficient of static friction than that of composite material 510 hereinbefore described. In that regard, the coefficient of static friction can be selected based upon the areas of the retention zones—the larger the skin contact area the lower the coefficient of static friction of the material needed to obtain substantially the same retention force, or slip resistance. Thus, a panel can be provided having a somewhat lower coefficient of static friction than that of exposed elastomeric scrim. A base nonwoven material, such as HEC, a high elongation carded nonwoven available from FiberWeb Corp., of Simpsonville, S.C., is joined with a layer of a blend of EVA and Kraton melt-blown fibers, by thermal calendaring, for example. The surface defined by the fibers has a coefficient of static friction of about 0.7, which is in excess of twice that of commercially available nonwoven materials. Panels so formed can be employed as the skin-facing surfaces of the side panels of an absorbent article, such as ear panels 10, 11 of the article shown in FIG. 2. Preferably, the area of such high-coefficient-of-friction retention zones included in the side panels is up to about 13 in$^2$, more preferably from about 3.5 in$^2$ to about 11 in$^2$, and most preferably from about 5 in$^2$ to about 6.5 in$^2$.

Retention zones that provide a diaper-to-skin slip resistance of about 1500 gm will generally be effective to prevent excessive sagging or drooping of the diaper, while also minimizing the tendency for red marking of the wearer's skin. Preferably the slip resistance is at least about 1000 gm, more preferably at least about 1500 gm, and most preferably about 2100 gm.

The slip resistance of a disposable diaper can be measured by providing a mannequin-type waist profile having the cross section shown in FIG. 11, but without the leg members. The profile has a height of 110 mm and a circumference of 492 mm and is formed from styrofoam. A material is applied to the exterior surface of the mannequin to simulate human skin. The preferred material is a product called BIOSKIN, which is a polyurethane material that can be obtained from Beaulax Company, of Japan, and can be attached to the mannequin by an adhesive such as Cemedine EP002, available from Cemedine KK, Tokyo, Japan. The BIOSKIN material has the following physical properties:

| | |
|---|---|
| Dimensions | 195 mm × 130 mm × 5 mm |
| Rigidity | 0 ~ 5 Shore A @25° C. |
| Tow Strength | 18 ~ 20 kg/cm$^2$ @23° C. |
| Tear Strength | 3 ~ 5 kg/cm$^2$ or more @23° C. |
| Grow Range | 450 ~ 500% |
| Transform Temperature | 90° C. |

In carrying out the slip resistance test procedure, a hole was drilled through the center of the mannequin, which was then mounted on a stand and connected with one plate of an Instron tester. The diaper was then connected with the Instron load cell, and was then mounted in wearing position on the mannequin. The diaper was allowed to relax on the mannequin for a period of 5 minutes. The load cell was programmed to move upward axially relative to the mannequin at 20 cm per minute and the load (gmf) as a function of displacement (cm) was noted. The peak load (gmf) was determined for various commercially available diapers. The slip resistance is the peak load (gmf) for that diaper at that circumference. The product wearing force (for a waist circumference of 492 mm) for each of the products was determined, and the product wearing force and the slip resistance were used to determine the normalized product slip resistance.

In addition to providing retention zones having a significantly higher coefficient of static friction than the usual skin-contacting materials that are included in presently-commercially-available disposable absorbent articles, the present invention also contemplates the provision of slip zones having a lower coefficient of static friction at selected skin-contacting areas of such structures. Providing such slip zones, or reduced friction zones, having a coefficient of static friction of less than about 0.2 facilitates the application and removal of such articles from the body of a wearer. In that regard, and referring to FIG. 2, the zones of such articles that generally provide relatively high resistance to easy application and removal of the articles include leg edges 153, 156, and 158, front waistband area 6, and the interior surfaces of the garment adjacent the leg openings, such as leg flap panels 4. Reduction of the coefficient of static friction in those areas to a level of less than about 0.15 can significantly reduce the drag forces that are experienced at specific areas of the body of a wearer, such as the front waist area and the thigh areas enclosed by the diaper leg openings, where because of the elastic properties at the leg cuffs and at the leg openings a relatively high pressure of the diaper structure against the skin or high abrasion forces on the skin can be experienced during application and removal of such garments. Suitable materials to provide such a reduced coefficient of friction include materials in patch form, such as silk, and sheet materials including meltblown or spunbonded fibers made from polyethylene.

As a further benefit, in addition to facilitating the application and removal of a disposable absorbent article, the selective provision on skin-contacting surfaces of the article of relatively high and relatively low coefficient of static friction zones can also improve the comfort and the functionality of the article during the time it is worn. Thus, providing slip zones at skin-contacting areas of the article that move relative to the wearer's skin during the course of bodily movements of the wearer can reduce skin abrasion and resultant red marking. Such high relative motion zones include the front waist portion of the article, more specifically the area that overlies the stomach of the wearer, and also the edges of the leg cuffs, where it is advantageous to provide low coefficient of static friction surfaces. Higher coefficient of static friction surfaces can be provided at the low relative motion zones of the article, such as at the leg crease, the hip-contacting sides, and the crotch crease, to aid in retaining the article in position for optimum functionality. By strategically providing high coefficient of static friction surfaces at the low relative motion zones and low coefficient of static friction surfaces at the high relative motion zones, the article can, in effect, be made to be self adjusting, relative to the wearer's body during wearing, to maintain the article in its preferred position on the wearer's body, to minimize skin abrasion, and to provide a greater degree of control over both the fit of the article and the positioning during wearing of critical functional elements of the article, such as the absorbent core and the leg cuffs.

Figures 12, 13:
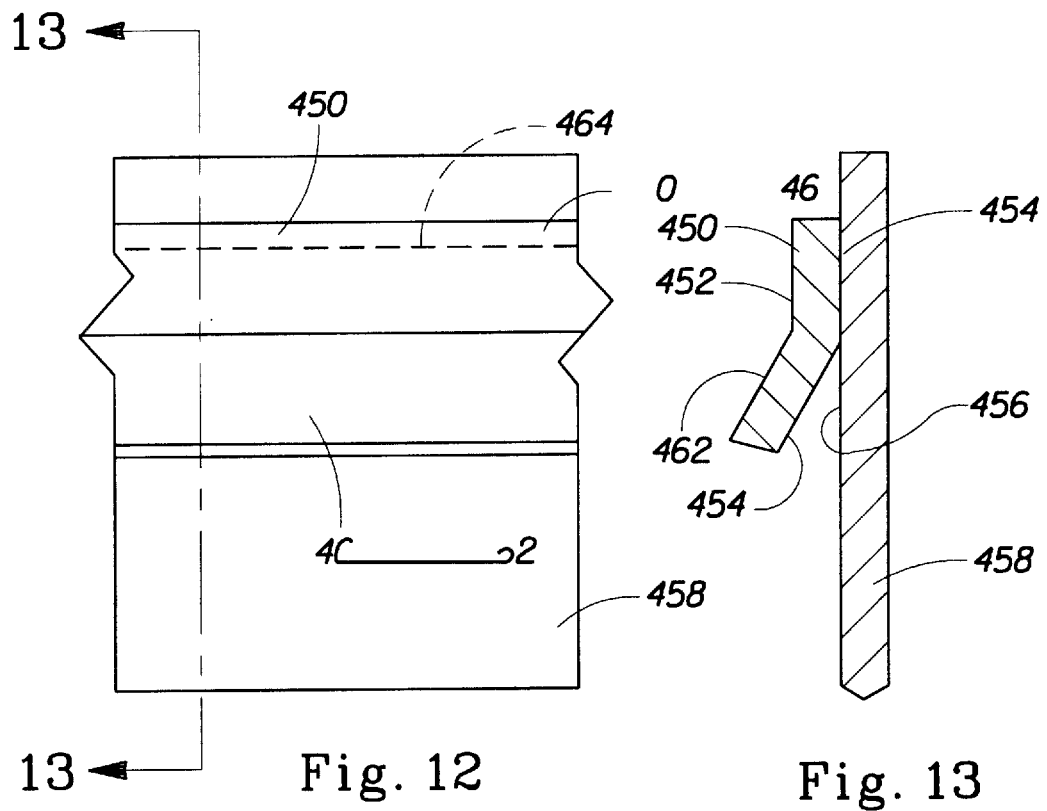
FIG. 12 is an enlarged, fragmentary view into the interior of the garment shown in FIG. 1, at the waist area, showing an inner flap member.
FIG. 13 is cross-sectional view taken along the line 13—13 of FIG. 12.
Figure 14:
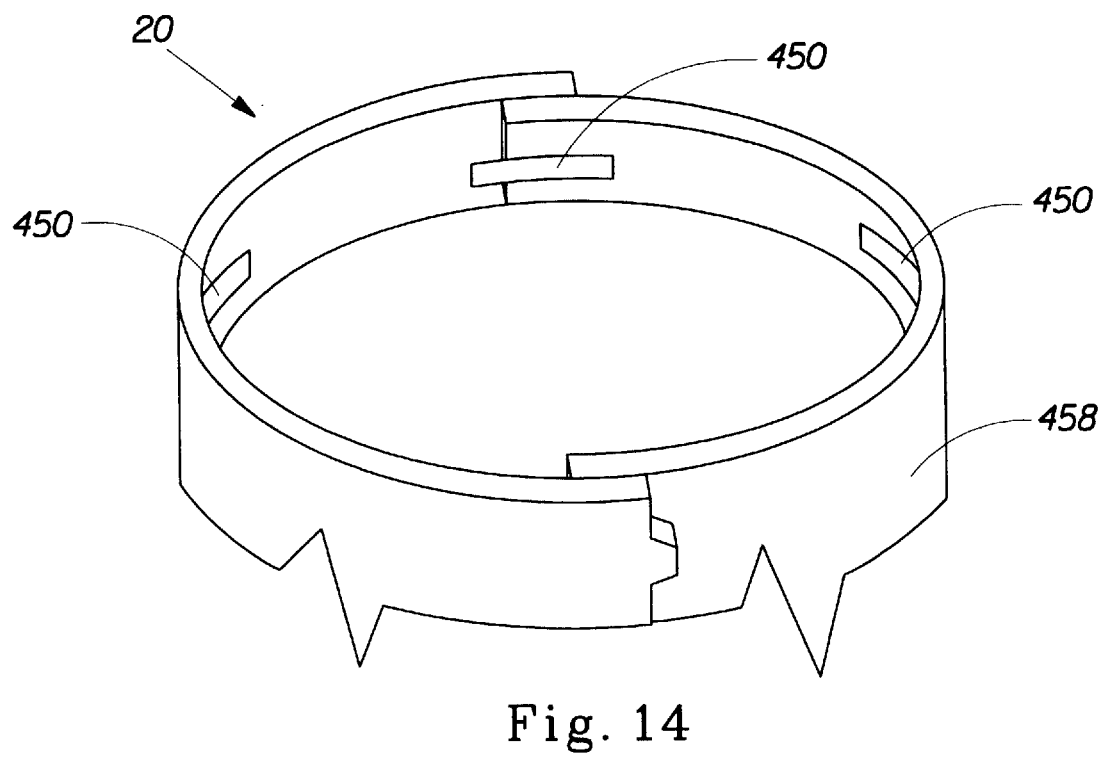
FIG. 14 is a fragmentary perspective view of the waist area of the garment of FIG. 1 including several inner flap members.

In addition to retention zones provided in the form of patches of materials having a relatively high coefficient of static friction, the present invention includes the provision of a retention zone in the form of an inner band 450 of retention material such as is shown in FIGS. 12 and 13. Band 450 can be an elongated, generally rectangular panel, as shown, having an outer face 452 adapted to face the wearer and to contact the wearer's skin, and an inner face 454 that faces toward the inner surface 456 of waistband 458. A portion of inner face 454 is secured to the interior surface of waistband 458 of the diaper along a seam area 460. The seam area can define a connection between band 450 and waistband 458 that can be effected by an adhesive, by heat sealing, or by other known connection means that are known to those skilled in the art.

Band 450 can be a thin, flexible sheet of soft, non-irritating material, such as a polymeric sheet, a nonwoven sheet, or the like. Preferably, the band material is made from the patch material previously described that includes a nonwoven base member and a scrim that is impressed into the surface of the nonwoven. The unattached portion of band 450 defines a flap 462 that can pivot about the lowermost edge 464 of seam area 460.

Outer face 452 of band 450 preferably has a relatively low coefficient of static friction, of the order of from about 0.2 to about 0.3, so that when the diaper is pulled over the legs of the wearer and onto his lower torso the low coefficient of friction enables application of the diaper to be effected without excessive resistance to sliding movement of the interior surface of the diaper waist relative to the wearer's skin. Such a relatively low coefficient of static friction can be obtained by appropriate selection of the band material, or it can be obtained by applying a suitable low friction surface over the outer face of the band. Examples of suitable low friction surfaces include silk, a layer of spunbonded polyethylene fibers, or a high elongation carded nonwoven such a HEC, available from FiberWeb corp., of Simpsonville, S.C.

Although outer face 452 has a relatively low coefficient of static friction, inner face 454 preferably has a relatively high coefficient of static friction. The relatively high coefficient of static friction is desirable because if the diaper slips downwardly relative to the body of the wearer, the limited frictional force resulting from the sliding movement of band 450 against the wearer's skin will cause flap 462 to pivot about edge 464, so that edge 464 will, in effect, as a hinge or a pivot axis. Accordingly, as the diaper begins to slip downwardly from its initial, as-applied position, the pivoting of flap 462 about edge 464 will cause inner face 454 of flap 462 to come into contact with the wearer's skin. Accordingly, a relatively high coefficient of static friction is provided on inner face 454 so that additional downward movement of the diaper from its initial position is impeded. In that regard, the preferred range of coefficient of static friction of inner face 454 is from about 0.3 to about 4.0, more preferably from about 0.4 to about 2.0, and most preferably from about 0.7 to about 1.5. The preferred coefficient of static friction of outer face 452 is less than about 0.2, more preferably less than about 0.15. It will thus be apparent that band 450 serves simultaneously as an aid to application of diaper 20 as well as an aid to retention of diaper 20 after it has been placed in its preferred wearing position.

The benefits of the present invention involving the provision of a stay-up disposable absorbent article, such as a disposable diaper, can also be achieved without the addition of special materials in patch or coating form. Thus, a disposable diaper having discrete areas of higher coefficient of static friction material can also be provided in a structural arrangement that is integral with the overall diaper structure, one that does not require the addition of special, separate and distinct higher-coefficient-of-static-friction materials. In that regard, the basic waistband structure hereinbefore described in the context of a disposable diaper can be modified so that elastic material that is positioned interiorly within the waistband of the diaper is selectively exposed. Elastic materials commonly included in such waistband structures typically have a higher coefficient of static friction than that of other materials defining the inner, body-facing surfaces of a diaper. The elastic material is caused to be exposed and to come into direct contact with the skin of the wearer at selected times, and when needed or desired to retain the diaper in its preferred wearing position.

One form of such a modified waistband structure is shown in FIG. 21. Waistband 600 is a continuous circumferential structure that has an outer surface layer 602 that faces away from the body of the wearer and an inner surface layer 604 that faces the body of the wearer. Layers 602 and 604 are separated from each other by and are bonded to at least one intermediate layer 606 that either constitutes or includes a layer of an elastic material having a higher static coefficient of friction than that of inner surface layer 604. The bonding together of the respective layers of the waistband structure can be effected by suitable adhesives that can be one of the adhesives hereinbefore described, or, alternatively, by thermal bonding or by other suitable bonding arrangements.

The modified waistband structure includes an inner surface layer 604 that has a plurality of substantially linear notches 608 that extend upwardly from the lowermost edge 610 of inner layer 604 and that terminate between lowermost edge 610 and uppermost edge 612. Notches 608 can be in the form of cuts or slits that extend completely through inner layer 604, and they can be located at predetermined circumferential positions around the inner circumference of waistband 600. The areas of inner layer 604 between pairs of adjacent notches 608 are not fully bonded to the elastic material of intermediate layer 606, but are instead permitted to hang loosely, as shown in exaggerated form in FIG. 22. Unbonded portions 613 of inner layer 604 between a pair of spaced notches 608 define respective pivotable cover flaps 614 that overlie and cover adjacent, underlying areas 615 of elastic material in intermediate layer 606 when the cover flaps are in the position shown in FIG. 22.

Cover flaps 614 can be caused to be pivoted or lifted to expose areas 615 of elastic material of intermediate layer 606 as the diaper begins to slip down from its initially-applied, preferred wearing position. The pivoting or lifting of the flaps relative to intermediate layer 606 is effected during downward movement of the waistband 600 relative to the body of the wearer, which results in a pulling force on cover flaps 614 that causes the flaps to pivot about a pivot line 616 that can be defined by the lowermost edge of the bonded area between inner layer 604 and intermediate layer 606.

After the diaper has moved downwardly along the body of the wearer a sufficient distance, cover flap 614 has pivoted about pivot line 616 to uncover area 615 of elastic material and to expose it to the skin of the wearer. The exposed elastic material, which either constitutes or forms a part of intermediate layer 606, has a significantly higher coefficient of static friction than that of the body-facing surface of inner layer 604, of the order of at least about 1.5, preferably about 2.0 or more. When the elastic material comes into contact with the skin of the wearer the frictional resistive force that results from the contact of the exposed area of elastic material with the skin of the wearer serves to resist further downward movement of the diaper and to retain the diaper in a position for effective functioning.

The unbonded areas in the form of cover flaps 614 can be positioned at the hip-contacting portions of the waistband to define hip-contacting cover flaps on one or both opposed inner surfaces at each side of the diaper structure. Further, one or more unbonded areas in the form of back-contacting cover flaps can be provided adjacent the portion of the diaper waistband structure that contacts the back of the wearer, either in addition to the hip-contacting cover flaps or instead of the hip-contacting cover flaps. The individual cover flaps can be a plurality of adjacent or spaced cover flaps each having a circumferential length of from about 0.5 in to about 12 in, preferably from about 1 in to about 2 in, or they can be relatively large, unitary circumferential cover flaps. In that regard, the cover flaps can encompass about 75% of the waistband inner circumference, preferably about 50%, and most preferably about 20%. If plural, relatively short circumferential length cover flaps are provided, preferably the individual flaps have a circumferential length of from about 0.1 in to about 5 in, more preferably from about 0.25 in to about 3 in, and most preferably from about 0.5 in to about 1 in.

The structure of a waistband incorporating one or more pivotable, discrete cover flaps can be as shown in FIGS. 21 and 22. Inner layer 604 and outer layer 602 of waistband material can each be a nonwoven material of the character of those hereinbefore described. The elastic material forming part of the intermediate layer 606 between the inner and outer layers 602, 604 can be an elastic scrim, such as the elastomeric scrims hereinbefore described and shown in FIGS. 6 and 15. Further, the elastic material can be in the form of a plurality of circumferentially-disposed bands. And instead of utilizing the elastic waistband material as the high coefficient of static friction material, the higher static coefficient of friction materials hereinbefore identified can be employed instead, if desired.

Instead of or in addition to one more unitary, circumferentially spaced pivotable flaps, a plurality of smaller flaps can be provided. As shown in FIG. 22a, inner surface layer 604 can include a plurality of flaps 618, wherein each of flaps 618 has a smaller flap dimension in the direction parallel to longitudinal centerline 100 of the diaper structure (see FIG. 3). The smaller flap structure shown in FIG. 22a provides diaper position retention benefits similar to those obtained with the unitary, larger flap shown in FIG. 22, but because of the smaller flap dimension it does so for smaller downward slippage of the diaper relative to the body of the wearer. Thus, by reducing flap dimension h shown in FIG. 22a, the retention feature comes into play more quickly when diaper downward slippage begins.

Figure 23:
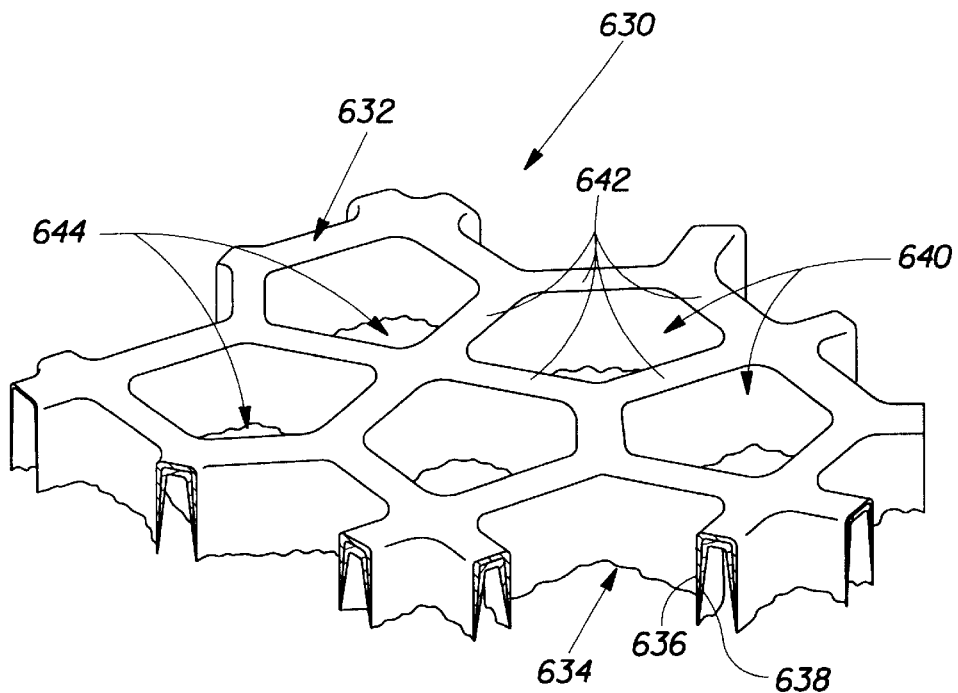
FIG. 23 is a fragmentary perspective view of a porous, elastomeric web.

As a further structural alternative, the elastic material in the diaper waistband can be in the form of a porous, macroscopically-expanded, three-dimensional elastomeric web 630 as shown in FIG. 23. Elastomeric web 630 has a discontinuous outer surface 632 and a discontinuous inner surface 634 that are spaced from each other to define the outwardly-facing surfaces of the web. Preferably, web 630 is a formed film, and it can include at least two polymeric layers, with at least one of the layers being an outer elastomeric layer 636 and at least one of the other layers being a substantially less elastomeric inner layer 638.

Elastomeric web 630 includes a multiplicity of apertures 640 in outer surface 632. Apertures 640 lie in the plane of outer surface 632 and are bounded by a continuous network of interconnecting members 642. Each interconnecting member 642 defines an inwardly-diverging cross-section along its length from outer surface 632 to inner surface 634. Interconnecting members 642 terminate at inner surface 634 to define inner apertures 644 that lie in the plane of inner surface 634 of web 630. The detail of such an elastomeric web structure and a method by which it can be manufactured is disclosed in U.S. patent application Ser. No. 08/816,106, filed Mar. 14, 1997, the disclosure of which is hereby incorporated by reference to the same extent as if fully rewritten. A preferred porous elastomeric material is available from Tredegar Industries, Inc., of Richmond, Va., under the designation X-25007.

The outer apertures 640 can have any desired shape. Preferably, however, outer apertures 640 have a shape that includes a major axis and a minor axis that are perpendicular to each other, such as an oval or elliptical shape. Preferably, the major axis is oriented generally orthogonal to strain induced stresses that are applied to the elastomeric web during the time the diaper is worn.

Figures 23A, 23B:
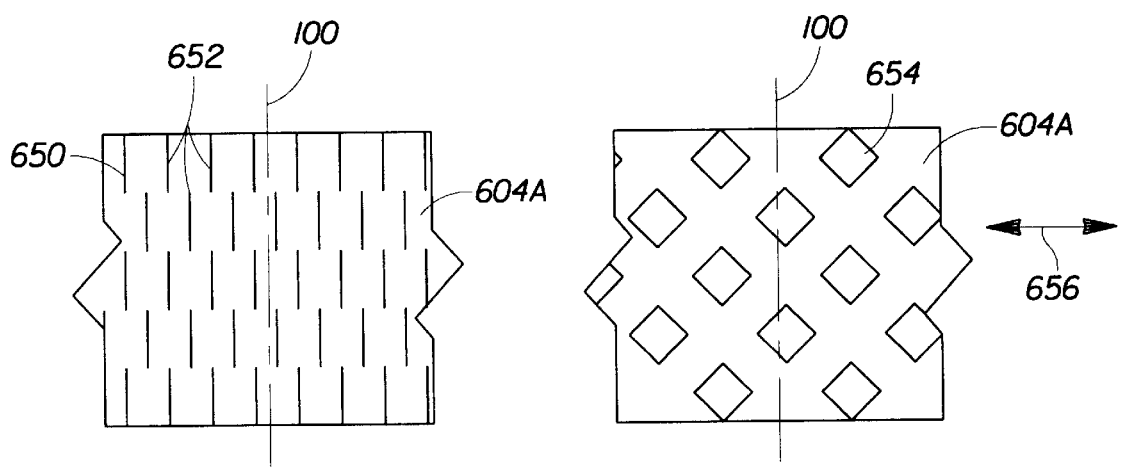
FIG. 23a is a fragmentary plan view of an inner, body-facing layer of waistband material that includes a plurality of spaced slits or cuts.
FIG. 23b is a fragmentary plan view of the material shown in FIG. 23a after it has been subjected to a tensile force.

A further variant of a diaper waistband structure in accordance with the present invention is shown in FIGS. 23a and 23b. Each of those drawing figures shows a modified waistband inner layer 604a that defines the body-facing surface of the waistband and that overlies a material having a relatively high coefficient of static friction. Layer 604a can be made from an extensible material, such as a nonwoven material of a type hereinbefore identified, but instead of a continuous, unbroken structure extensible layer 604a includes a plurality of relatively short, substantially linear cuts or slits 650 that are spaced from each other and that extend completely through the material defining layer 604a.

As shown in FIG. 23a, slots 650 extend in the direction of longitudinal centerline 100 (see FIG. 3) of the diaper structure. A plurality of spaced, substantially parallel rows 652 of generally aligned slits 650 are provided, with the slits in adjacent rows 652 longitudinally offset from each other. As a result, when layer 604a is placed under tension in a direction transverse to longitudinal centerline 100, which corresponds with the circumferential direction of the waistband on a diaper, the edges of slits 650 will separate from each other to define a plurality of spaced openings 654. Thus, when openings are formed in layer 604a the underlying layer of relatively high coefficient of static friction material will be partially exposed to the skin of the wearer, thereby providing the desired resistance to downward slippage of the diaper when it is worn. As shown in exaggerated form in FIG. 23b, openings 654 will assume substantially a diamond shape, with the area of each opening dependent upon the lengths of the slits, the extensibility of the material, and the tensile stress (represented by double-headed arrow 656) that is imposed on layer 604a. Slits 650 can have a length of from about 2 mm to about 5 mm, preferably from about 2 mm to about 3 mm, and a longitudinal spacing between adjacent slits in a given row of from about 2 mm to about 5 mm. Further, the lateral spacing between adjacent rows 652 of slits can be of the order of from about 2 mm to about 5 mm. The slits can be provide by passing a sheet of the material through a rotary cutter apparatus of a type known to those skilled in the art.

Layer 604a can be adhesively secured to an underlying layer of elastic material, such as an elastomeric scrim having a relatively high coefficient of static friction, that is exposed upon the formation of openings 654. Alternatively, a layer of adhesive that is utilized to secure layer 604a to an underlying structural layer of waistband material can also be the relatively high coefficient of static friction material, which when placed under tension will expose the adhesive material upon formation in layer 604a of openings 654. The adhesive can be sprayed on an underlying layer of material, or it can be applied in a pattern of adhesive-containing areas and non-adhesive-containing areas, such as a spiral pattern, or the like.

In addition to providing one or more discrete zones having one or more pivotable flaps to cover and uncover a scrim that defines a zone having a high coefficient of static friction, permanently exposed areas of scrim can also be provided, if desired. In that case one or more portions of the inner circumference of the waistband is covered by a suitable covering material, such as a nonwoven of the type described herein, with intervening areas of exposed scrim of substantially uniform coefficient of static friction that extend over predetermined areas of the skin-facing surface of the waistband.

If the high coefficient of static friction areas are provided by a material that overlies a base material, such as a nonwoven, that material can be applied in such a way as to vary the coefficient of static friction from a relatively high value to a lower value over a given area. Thus, material that is added to the interior surface of the diaper can be applied in a denser pattern at. predetermined areas to provide a high coefficient of static friction, and can the density of the applied material can diminish in a circumferential direction of the waistband, so that the coefficient of static friction varies over predetermined areas from a relatively high coefficient of static friction to a relatively low value. More specifically, when the coefficient of static friction of a portion of the interior surface of the diaper is increased by laying fibers of meltblown material, the density of the fiber application can be gradually varied from a high fiber density that provides a high coefficient of static friction, to a lower fiber density so that the coefficient of static friction diminishes substantially uniformly.

Figure 24:
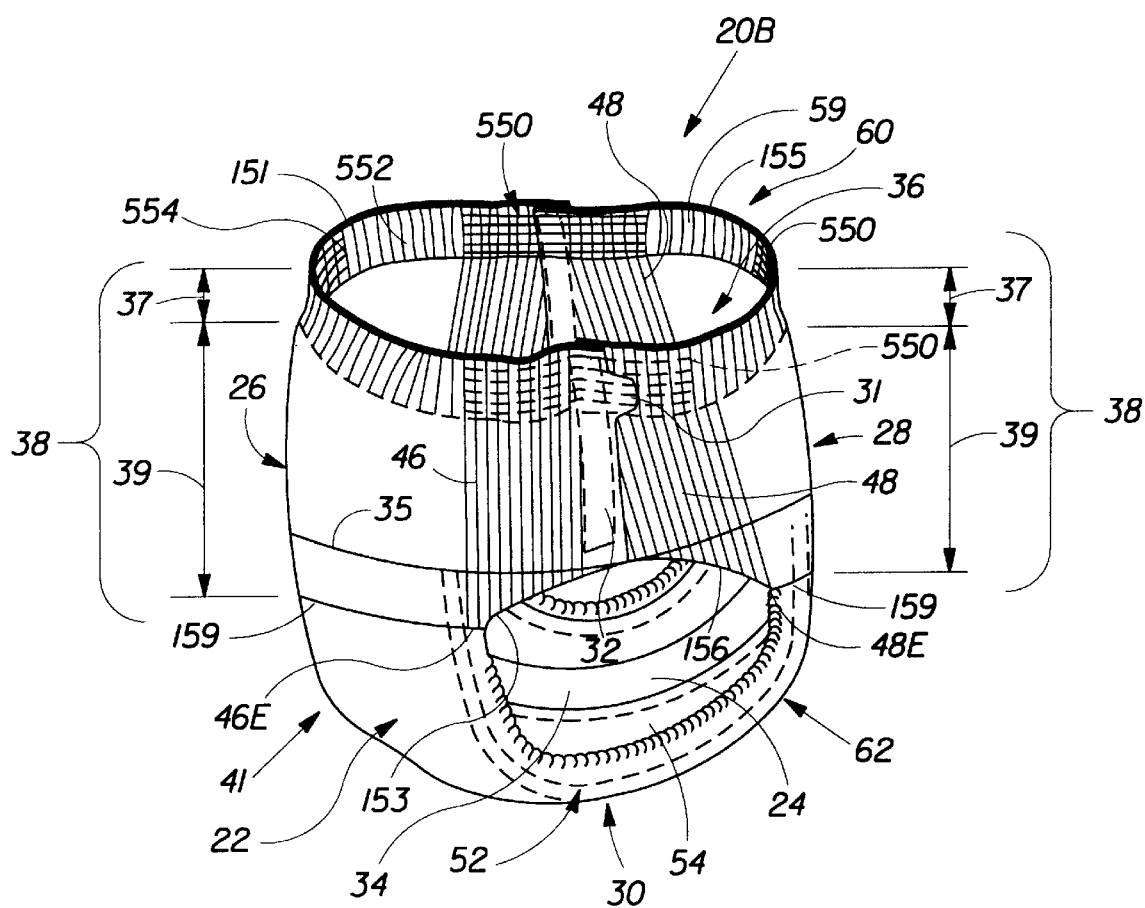
FIG. 24 is perspective view of another embodiment of a pull-on diaper in accordance with the present invention.

Alternatively, instead of a gradual variation of coefficient of static friction, the friction-increasing material can be applied at particular densities in discrete areas on the interior surface of the diaper to provide zones of high coefficient of static friction, intermediate coefficient of static friction, and low coefficient of static friction. Each of those areas can have a relatively uniform coefficient of static friction value within the area of a given zone, or the coefficient of static friction values can vary gradually. As shown in FIG. 24, waistband 37 of pull-on diaper 20b includes a high coefficient of static friction zone 550 at the opposed, hip-contacting areas of the waistband. Zones 550 have an area as hereinbefore defined and have a coefficient of static friction of from about 1.5 to about 3.0. Waistband 37 also includes one or more intermediate level coefficient of static friction zones 552 each having a area of from about 1 in$^2$ to about 4 in$^2$, and having a coefficient of static friction of from about 0.2 to about 1.5, and at least one low coefficient of static friction zone 554 having an area of from about 1 in² to about 4 in², and having a coefficient of static friction of from about 0.05 to about 0.20. As shown in FIG. 24, high coefficient of static friction zones 550 can be provided at each of the side, hip-contacting portions of waistband 37 of the diaper, and optionally also at the back-contacting portion of the waistband. Low coefficient of static friction zone 554 can advantageously be provided at the stomach-contacting portion of the waistband, which generally undergoes more relative movement over the wearer's skin than do the hip- and back-contacting areas. Intermediate coefficient of static friction zones 552 can be provided between high coefficient of static friction zones 550 at the hips and at the back, and also between high coefficient of static friction zones 550 at the hip-contacting areas and a low coefficient of static friction zone 554 at the stomach-contacting area. Thus, the interior surface of waistband 37 shown in FIG. 24 can have plural discrete zones that have different coefficients of static friction to provide a circumferential variation in waistband coefficient of static friction.

In addition to the circumferentially-distributed waistband zones having differing coefficients of static friction, the diaper can also have varying coefficient of static friction zones that are outside the inner waistband area. For example, and referring to FIG. 2, zones that vary in coefficient of friction can also be provided on the skin-facing surfaces of areas such as central panels 8 and 9 and ear panels 10 and 11 that extend between waistband 6, 7 and crotch region 30.

Figure 25:
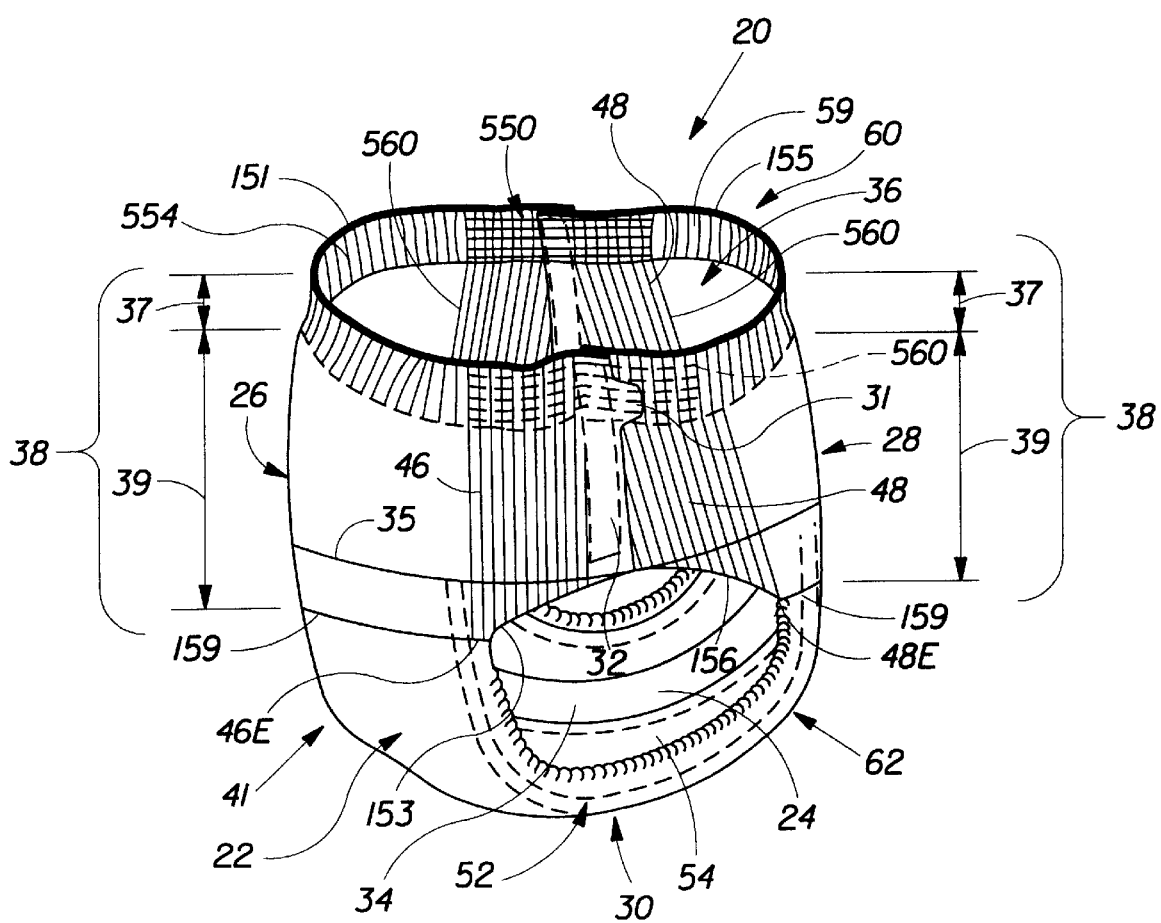
FIG. 25 is a perspective view of a still further embodiment of a pull-on diaper in accordance with the present invention.

Referring to FIG. 25, diaper 20c includes high coefficient of static friction hip-contacting zones 550 on each side of the diaper along the inner surfaces of waistband 37, and intermediate coefficient of static friction zones 560 on each side of high coefficient of static friction zones 550. Intermediate coefficient of static friction zones 560 extend from waistband 37 to leg edges 153 and 156. In that regard, the interior, body-contacting surfaces of panels 46 and 48 that define those intermediate coefficient of static friction areas can each be provided with an interior coating or a separately-applied material that provides an intermediate level of coefficient of static friction value of from about 0.2 to about 1.5. And the front and rear panels defined by the interior surface of topsheet 24 can include a low coefficient of static friction material, having a coefficient of static friction of from about 0.05 to about 0.20, because those areas undergo greater degrees of movement relative to the skin of the wearer as the wearer moves about, thereby contributing to greater wearer comfort and reduced skin irritation in those areas experiencing greater relative movement between the skin and the interior surface of the diaper.

The invention has been described herein principally in the context of a pre-assembled, pull-on diaper that is in ready-to-wear condition as received and that does not require attachment of particular structural element to each other by the person who applies the diaper to the body of a wearer. An example of such a pull-on diaper is the structure disclosed in U.S. Pat. No. 5,685,874, entitled "Disposable Pull-On Pant," which issued to Kenneth B. Buell et al., on Nov. 11, 1997.

Another form of diaper structure in which the present invention can be advantageously employed is the relatively flat diaper structure that is applied to the body of a wearer and that requires the person who applies the diaper to connect fastener elements to retain the diaper in wearing position on the body of the wearer, such as by the manipulation and attachment of tape-type fasteners. One such non-assembled diaper structure, one that is in substantially flat condition as received, is disclosed in U.S. Pat. No. 5,151,092, entitled "Absorbent Article with Dynamic Elastic Waist Feature Having a Predisposed Resilient Flexural Hinge," which issued to Kenneth B. Buell et al., on Sep. 29, 1992. The disclosures of each of the foregoing Buell et al. patents are hereby incorporated herein by reference to the same extent as if fully rewritten.

Although described hereinabove in the context of a pre-formed, pull-on diaper, the present invention involving the provision of selectively different areas of coefficient of static friction can also be utilized in other absorbent articles that are worn. In addition to the pull-on diaper and the flat diaper structures, the present invention can also be employed in disposable absorbent articles commonly referred to as "convertible diapers," or "convertible belted diapers." Such so-called convertible structures include a fastening system that provides different assembly and application and removal alternatives. Those alternatives allow the convertible structure to be used either in a pre-assembled, pull-on form, or in a non-pre-assembled, flat form, to enable the person applying and removing the diaper to select how the article is applied to and removed from the body of the wearer. For example, the convertible diaper can be applied and removed by pulling the diaper up or down along the legs of the wearer, or it can be applied by wrapping the diaper about the torso of the wearer and utilizing the fastening system to retain it in wearing position, and can be removed by releasing the fastening system and opening the diaper for removal from the wearer. The convertible diaper structures therefore include a fastening system that permits a choice between a pre-assembled, pull-on diaper, and a conventional, flat, non-pre-assembled diaper. The fastening system facilitates easy application and removal of the diaper, as well as easy opening of the diaper while it is worn, for inspection for soiling. One form of such a convertible diaper structure is disclosed in U.S. Statutory Invention Registration No. H1674, entitled "Convertible Belted Diaper," which names as inventors Kathleen Q. Ames et al., and which was published on Aug. 5, 1997, the disclosure of which is hereby incorporated herein by reference to the same extent as if fully rewritten.

Although particular embodiments of the present invention have been illustrated and described, it will be apparent to those skilled in the art that various changes and modifications can be made without departing from the spirit of the present invention. It is therefore intended to encompass within the appended claims all such changes and modifications that fall within the scope of the present invention.

What is claimed is:

1. A disposable garment adapted to be worn on the lower torso of a wearer, said garment comprising:

a. a chassis including a topsheet, a backsheet joined with the topsheet, and an absorbent core interposed between the topsheet and the backsheet, the chassis having a front region, a back region, and a crotch region positioned between the front region and the back region, the chassis including side edges and end edges and having body-facing surfaces and surfaces that face away from the body of a wearer;

b. a pair of side seams joining portions of the side edges of the chassis at the front region to other portions of the respective side edges of the chassis at the back region to define a pair of side panels adapted to overlie a hip area of a wearer and to form a garment having a pair of laterally spaced leg openings and a waistband defining a waist opening spaced from each of the leg openings and including a body-facing waistband inner surface, wherein the waistband and the side panels are elastically extensible; and c. at least one garment retention zone positioned interiorly of the garment at the waist opening, the garment retention zone having a surface slip resistance of at least about 1000 gm and having a coefficient of static friction that is at least about 200% greater than that of other body-contacting portions of the waistband, to assist in retention of the garment in a desired wearing position on the body of a wearer.

2. A disposable garment in accordance with claim 1 wherein the area of the retention zone is from about 0.25 in$^2$ to about 10 in$^2$.

3. A disposable garment in accordance with claim 1 wherein the coefficient of static friction in the retention zone is from about 0.5 to about 3.0.

4. A disposable garment in accordance with claim 1 wherein the garment includes plural retention zones.

5. A disposable garment in accordance with claim 4 wherein retention zones are positioned at areas of the garment that contact the hip areas of a wearer when the garment is worn.

6. A disposable garment in accordance with claim 4 wherein the garment includes a retention zone at a back-contacting area of the waistband of the garment.

7. A disposable garment in accordance with claim 1 wherein the retention zone is air permeable.

8. A disposable garment in accordance with claim 1 wherein the retention zone is a continuous area and has a substantially uniform coefficient of static friction over its area.

9. A disposable garment in accordance with claim 1 including a plurality of first retention zones each having a first coefficient of static friction, and intervening second retention zones between the first retention zones, the intervening retention zones having a second coefficient of static friction different from that of the first retention zones.

10. A disposable garment in accordance with claim 9 wherein the second coefficient of static friction is lower than the first coefficient of static friction.

11. A disposable garment in accordance with claim 1 wherein the retention zone is defined by a coating that overlies a portion of an interior, body-facing surface of the waistband.

12. A disposable garment in accordance with claim 11 wherein the coating is selected from the group consisting of polymeric materials, pressure-sensitive adhesive materials, rubber-based materials, and combinations thereof.

13. A disposable garment in accordance with claim 1 wherein the retention zone is defined by a thin polymeric film that is attached to an inner surface of the waistband.

14. A disposable garment in accordance with claim 1 wherein the retention zone extends along a side seam and the coefficient of static friction is greatest at the waistband and diminishes in value toward the leg opening.

15. A disposable garment in accordance with claim 1 including slip zones within the interior, body-facing surface of the garment, the slip zones having a coefficient of static friction that is less than about 0.20.

16. A disposable garment in accordance with claim 15 wherein slip zones are positioned on the interior surface of the garment adjacent the leg openings.

17. A disposable garment in accordance with claim 16 wherein slip zones are positioned on the inner surface of the waistband at points between the retention zones.

18. A disposable garment in accordance with claim 1 wherein the retention zone is defined by a nonwoven fibrous polymeric material.

19. A disposable garment in accordance with claim 18 wherein the nonwoven fibrous material includes meltblown polymeric fibers that are applied to a portion of the body-facing surface of the garment.

20. A disposable garment in accordance with claim 1 wherein the waistband includes retention zones that overlie from about 10% to about 100% of the waistband inner circumference when the waistband is in its relaxed, unextended condition.

21. A disposable garment in accordance with claim 1 wherein the waistband includes retention zones that overlie from about 25% to about 35% of the waistband inner circumference when the waistband is in its relaxed, unextended condition.

22. A disposable garment in accordance with claim 1 wherein the waistband inner surface includes a pivotable flap that covers the retention zone so that pivoting of the flap exposes the retention zone.

23. A disposable garment in accordance with claim 22 wherein the retention zone includes an elastomeric material forming part of the waistband of the garment and facing and underlying the pivotable flap when the flap is in its unpivoted position.

24. A disposable garment in accordance with claim 22 wherein the retention zone is carried on an inner surface of the pivotable flap.

25. A disposable garment in accordance with claim 22 wherein the flap includes a first, body-facing surface having a first coefficient of static friction and a second surface that initially faces away from the body of the wearer and that has a second coefficient of static friction different from that of the first surface.

26. A disposable garment in accordance with claim 25 wherein the first coefficient of static friction is less than the second coefficient of static friction.

27. A disposable garment in accordance with claim 26 wherein the first coefficient of static friction is less than about 0.2 and the second coefficient of static friction is at least about 0.5.

28. A disposable garment in accordance with claim 1 wherein the retention zone has a surface slip resistance of at least about 2100 gm.

29. A disposable garment in accordance with claim 1 wherein the retention zone has a surface slip resistance of at least about 1500 gm.

30. A disposable garment in accordance with claim 1 wherein the retention zone has an outer, skin-facing surface defined by an elastomeric material.

31. A disposable garment in accordance with claim 30 wherein the elastomeric material has a coefficient of static friction of about 3.0.

32. A disposable garment in accordance with claim 1 wherein the waistband includes:

a. an extensible outer layer of nonwoven material that has a soft, cloth-like feel and appearance;

b. an extensible inner layer of nonwoven material that has a soft, cloth-like feel and appearance;

c. an extensible intermediate layer including a material having a higher coefficient of static friction than the inner layer positioned between each of the inner and outer nonwoven layers to define the waistband, wherein the intermediate layer is bonded to at least portions of the inner layer to provide bonded areas and unbonded areas, wherein the higher coefficient of static friction material is elastically extensible in a circumferential direction of the waistband; and d. a plurality of spaced cuts extending through the inner layer from a lower edge thereof to a point between the lower edge and an upper edge thereof to define at least one circumferential flap member, the flap member overlying an unbonded area between the inner layer and the intermediate layer so that the flap member is pivotable about a circumferential pivot line interconnecting a pair of consecutive spaced cuts to expose the higher coefficient of static friction material when the waistband structure is moved over the skin of the user in a direction that is substantially parallel to an inner surface of the inner layer and substantially perpendicular to a circumferential stretch direction of the waistband.

33. A disposable garment in accordance with claim 17, including intermediate coefficient of static friction zones positioned between the retention zones and the slip zones.

34. A disposable garment in accordance with claim 33 wherein the intermediate coefficient of static friction zones have a coefficient of static friction of from about 0.20 to about 1.5.

35. A disposable garment in accordance with claim 34 wherein the retention zones have a coefficient of static friction of from about 0.5 to about 3.0.

36. A disposable garment in accordance with claim 1 wherein the garment includes ear panels that extend between the waistband and the leg openings, the ear panels having inner, skin-facing surfaces that have a coefficient of static friction that varies from about 1.5 to about 3.0 adjacent the waistband to from about 0.05 to about 0.20 adjacent the leg openings.

37. A disposable garment in accordance with claim 1 wherein the waistband includes:

a. an extensible outer layer of nonwoven material that has a soft, cloth-like feel and appearance;
   b. an extensible inner layer of nonwoven material that has a soft, cloth-like feel and appearance; and
   c. an extensible intermediate layer including a material having a higher coefficient of static friction than the inner layer positioned between each of the inner and outer nonwoven layers to define the waistband, wherein the intermediate layer is bonded to at least portions of the inner layer to provide bonded areas and unbonded areas, wherein the higher coefficient of static friction material is elastically extensible in a circumferential direction of the waistband;
   d. the extensible inner layer including a plurality of pivotable, circumferentially extending flaps overlying respective unbonded areas, wherein the flaps are pivotable about respective pivot axes that extend in a circumferential direction relative to the waistband to expose the higher coefficient of static friction material.

38. A disposable garment in accordance with claim 32 wherein the higher coefficient of static friction material is an elastomeric scrim.

39. A disposable garment in accordance with claim 1 wherein the waistband includes:

a. an extensible outer layer of nonwoven material that has a soft, cloth-like feel and appearance;
   b. an extensible inner layer of nonwoven material that has a soft, cloth-like feel and appearance; and
   c. an extensible intermediate layer including a material having a higher coefficient of static friction than the inner layer positioned between each of the inner and outer nonwoven layers to define the waistband, wherein the intermediate layer is bonded to at least portions of the inner layer to provide bonded areas and unbonded areas, wherein the higher coefficient of static friction material is elastically extensible in a circumferential direction of the waistband;
   d. wherein the inner layer includes a plurality of spaced slits extending through the inner layer and extending transversely relative to a circumferential dimension of the waistband, so that upon circumferential extension of the waistband the slits open to expose the higher coefficient of static friction material.

40. A disposable garment in accordance with claim 39 wherein the higher coefficient of static friction material is elastomeric.

41. A disposable garment in accordance with claim 40 wherein the higher coefficient of static friction material is a scrim.

42. A disposable garment in accordance with claim 39 wherein the slits are aligned in a plurality of side-by-side columns in which laterally adjacent slits are offset from each other in a longitudinal direction of the columns.

* * * * *

UNITED STATES PATENT AND TRADEMARK OFFICE
CERTIFICATE OF CORRECTION

PATENT NO. : 6,626,879 B1
DATED : September 30, 2003
INVENTOR(S) : Gregory Ashton et al.

It is certified that error appears in the above-identified patent and that said Letters Patent is hereby corrected as shown below:

Title page,
Item [75], Inventors, delete the name "Vijay Rajagopalan, Kobe (IN)".
Item [56], References Cited, U.S. PATENT DOCUMENTS, delete "*" after "5,246,433 A"; delete "*" after "5,782,819 A"; and delete "*" after "5,858,013".
FOREIGN PATENT DOCUMENTS, delete "*" after "EP 0 641 552 A1"; and add
-- EP 0873739 A1 10/28/98
   WO 00/72791 A1 12/7/00 --.

Column 1,
Line 64, delete "worm" and insert therefor -- worn --.

Column 2,
Line 22, delete "wearers" and insert therefor -- wearer's --.
Line 37, delete the second "No."
Line 39, delete "Intemational" and insert therefor -- International --.

Signed and Sealed this

Twenty-eighth Day of December, 2004

JON W. DUDAS
*Director of the United States Patent and Trademark Office*